US010994147B2

(12) United States Patent
Scott et al.

(10) Patent No.: US 10,994,147 B2
(45) Date of Patent: May 4, 2021

(54) IMPLANTABLE MEDICAL DEVICE STRUCTURES

(71) Applicant: Medtronic, Inc., Minneapolis, MN (US)

(72) Inventors: Erik R. Scott, Maple Grove, MN (US); Darren A. Janzig, Center City, MN (US); John E. Kast, Hugo, MN (US); Randy S. Roles, Elk River, MN (US); Don A. Rutledge, Corcoran, MN (US); Nicholas R. Whitehead, Lake Elmo, MN (US); Phillip C. Falkner, Minneapolis, MN (US); Venkat R. Gaddam, Plymouth, MN (US); Connor T. Gunsbury, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 161 days.

(21) Appl. No.: 16/115,170

(22) Filed: Aug. 28, 2018

(65) Prior Publication Data
US 2019/0060656 A1 Feb. 28, 2019

Related U.S. Application Data

(60) Provisional application No. 62/552,936, filed on Aug. 31, 2017, provisional application No. 62/645,989, filed on Mar. 21, 2018.

(51) Int. Cl.
A61N 1/375 (2006.01)
A61N 1/05 (2006.01)
(Continued)

(52) U.S. Cl.
CPC ....... A61N 1/37514 (2017.08); A61N 1/0531 (2013.01); A61N 1/375 (2013.01);
(Continued)

(58) Field of Classification Search
CPC .. A61N 1/37514; A61N 1/0531; A61N 1/375; A61N 1/3752; A61N 1/37518
See application file for complete search history.

(56) References Cited

U.S. PATENT DOCUMENTS 5,906,634 A 5/1999 Flynn et al.
6,026,089 A 2/2000 Hawkins et al.
(Continued)

FOREIGN PATENT DOCUMENTS

EP 2498871 A1 9/2012

OTHER PUBLICATIONS

International Search Report and Written Opinion of International Application No. PCT/US2018/049047, dated Jan. 28, 2019, 17 pp.
(Continued)

Primary Examiner — Joseph M Dietrich
(74) Attorney, Agent, or Firm — Shumaker & Sieffert, P.A.

(57) ABSTRACT

An implantable medical device (IMD) includes a housing that is configured to enclose internal components including at least a processor and a power source. The housing defines two major surfaces that are generally parallel to each other and one or more channels that are each configured to receive a lead and electrically couple the respective lead to the internal components, where each of the channels extend substantially straight in to the housing along an axis generally parallel to the two major surfaces. The housing may be configured to be mounted to a cranium of a patient such that at least one of the two major surfaces approximates a curvature of the cranium. The IMD may include one or more funneling walls that define a rounded and smooth transition from a sidewall of the housing to a surface that defines one or more mouths to the channels.

28 Claims, 25 Drawing Sheets

(51) Int. Cl.
　　　*A61N 1/36*　　　(2006.01)
　　　*A61N 1/372*　　　(2006.01)
(52) U.S. Cl.
　　　CPC .......... *A61N 1/3752* (2013.01); *A61N 1/0534*
　　　　　(2013.01); *A61N 1/0551* (2013.01); *A61N*
　　　　*1/36064* (2013.01); *A61N 1/36071* (2013.01);
　　　　　*A61N 1/36096* (2013.01); *A61N 1/37211*
　　　　　　　(2013.01); *A61N 1/37518* (2017.08)

(56) References Cited

U.S. PATENT DOCUMENTS

| | | | |
|---|---|---|---|
| 2004/0176818 A1* | 9/2004 | Wahlstrand | A61N 1/3605 |
| | | | 607/45 |
| 2011/0112612 A1 | 5/2011 | Rahmn | |
| 2011/0184479 A1 | 7/2011 | Kast et al. | |
| 2017/0056656 A1 | 3/2017 | Meskens et al. | |
| 2017/0281936 A1 | 10/2017 | Aghassian et al. | |
| 2019/0290911 A1 | 9/2019 | Whitehead et al. | |

OTHER PUBLICATIONS

Invitation to Pay Additional Fees from International Application No. PCT/US2018/049047, dated Dec. 4, 2018, 11 pp.
International Preliminary Report on Patentability from International Application No. PCT/US2018/049047, dated Mar. 12, 2020, 10 pp.

* cited by examiner

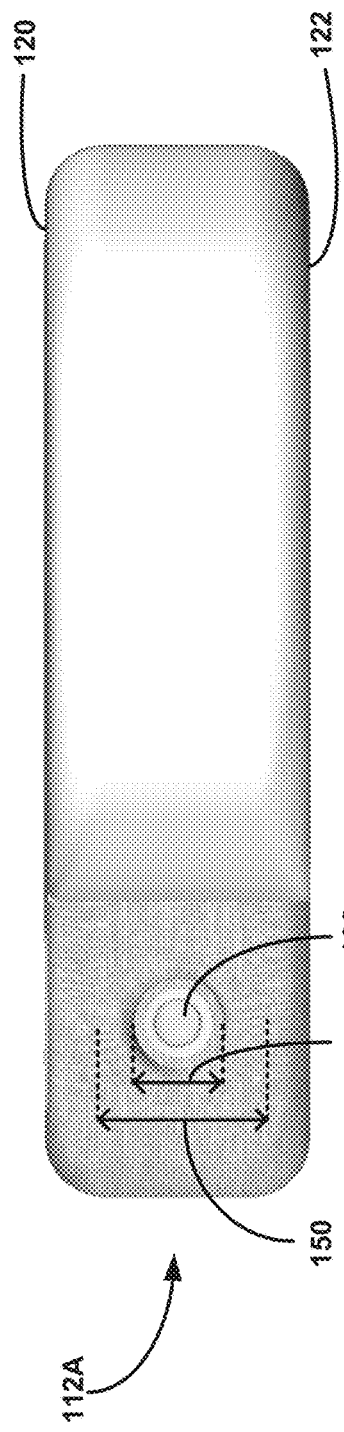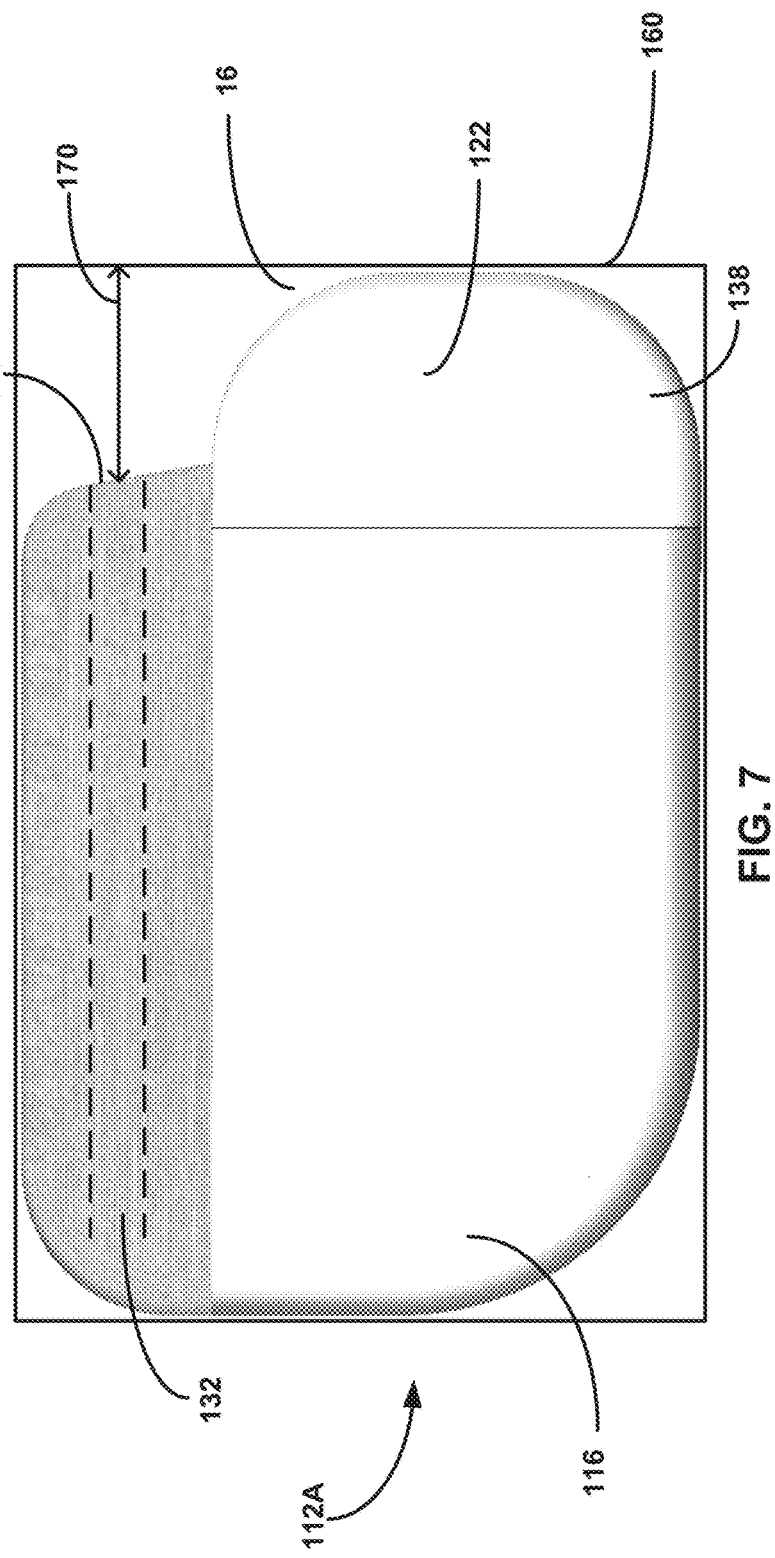

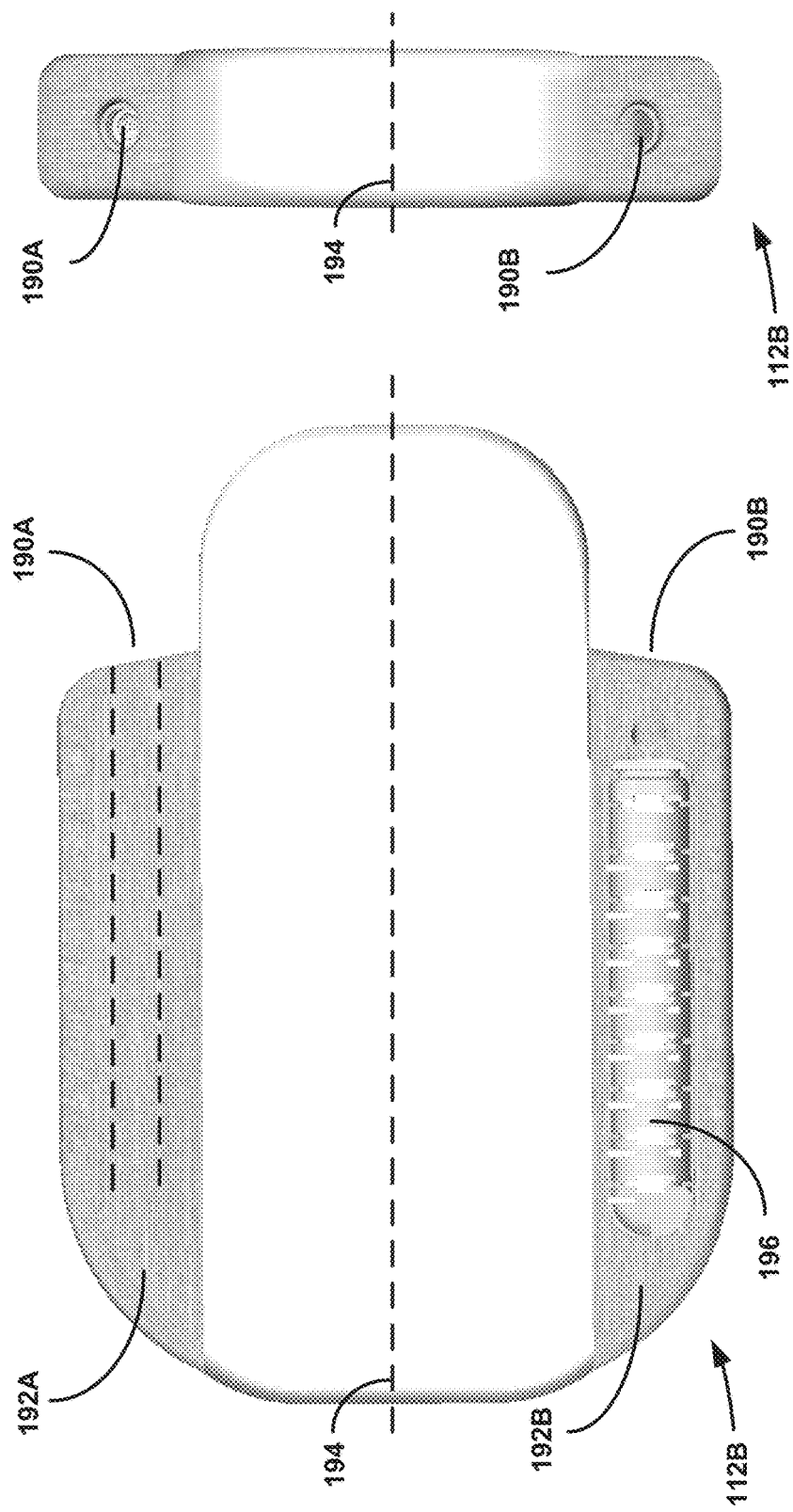

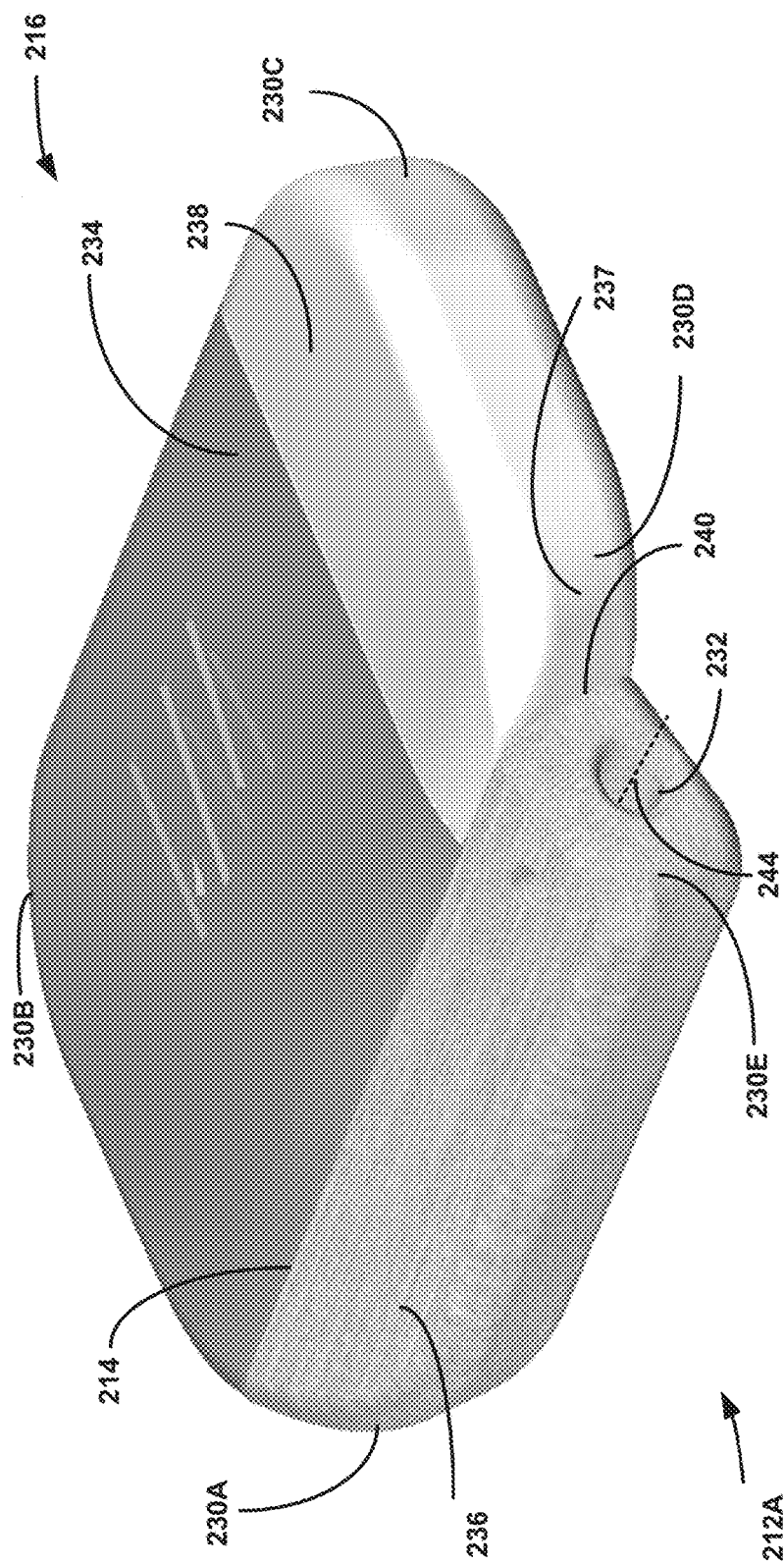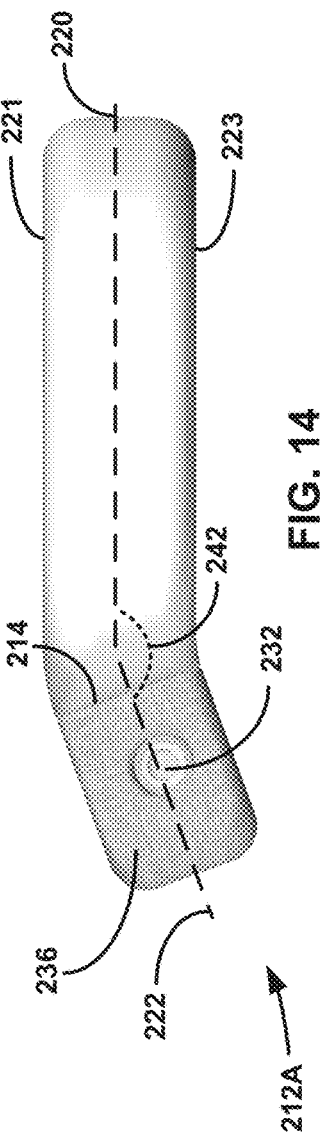

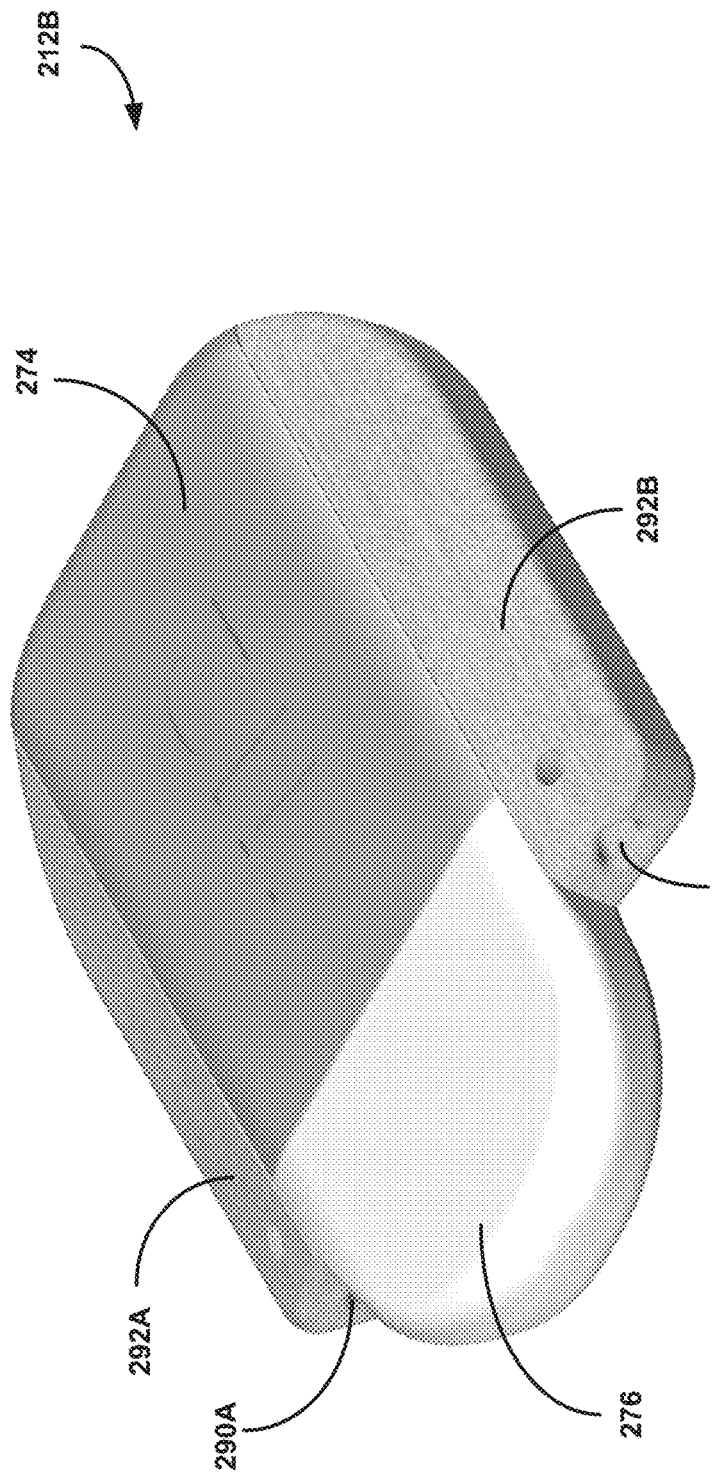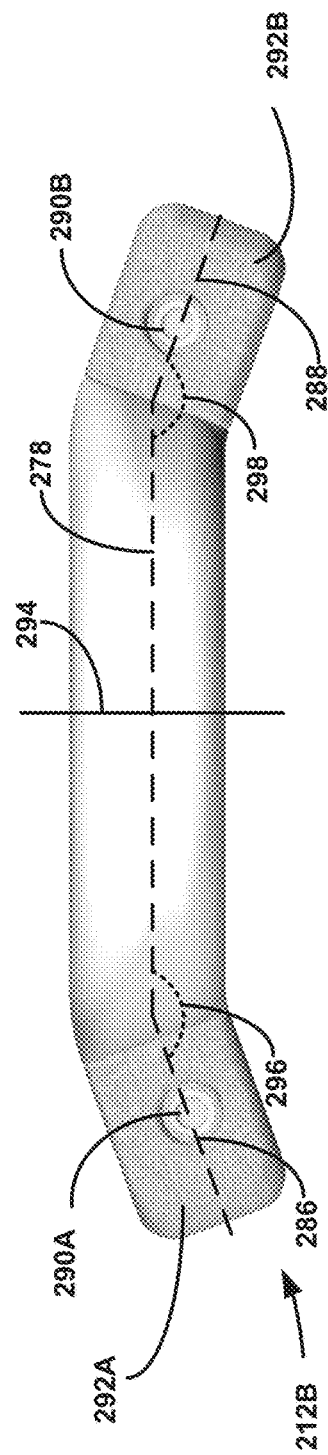
FIG. 17
FIG. 18

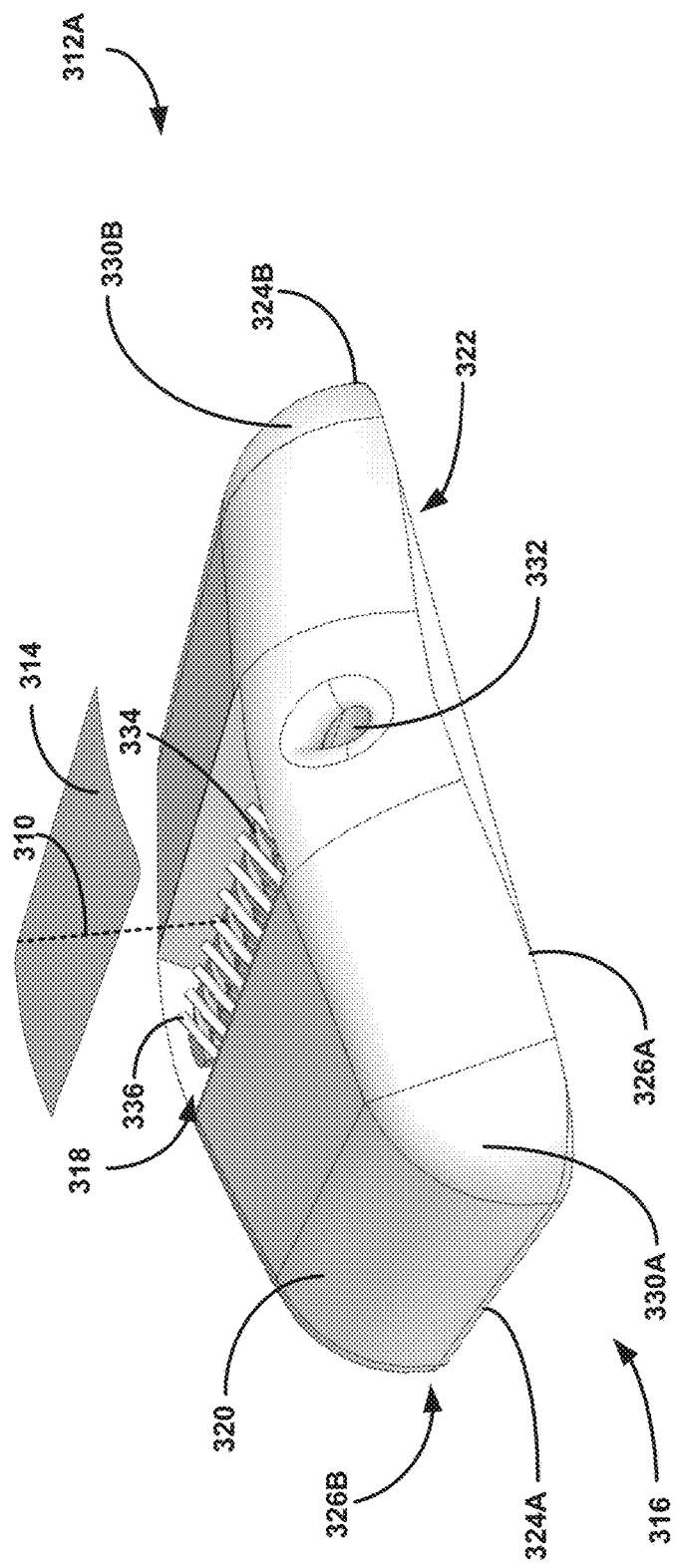
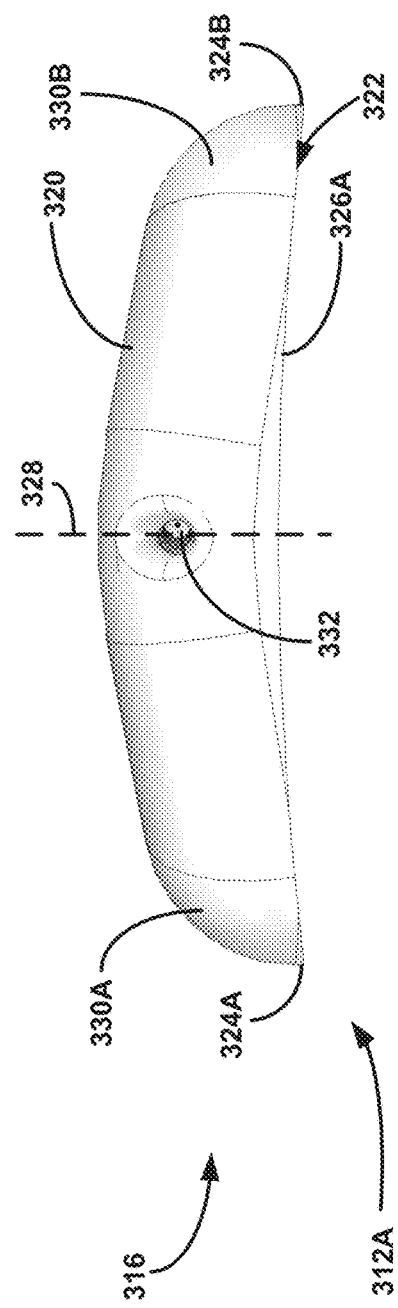
FIG. 19
FIG. 20

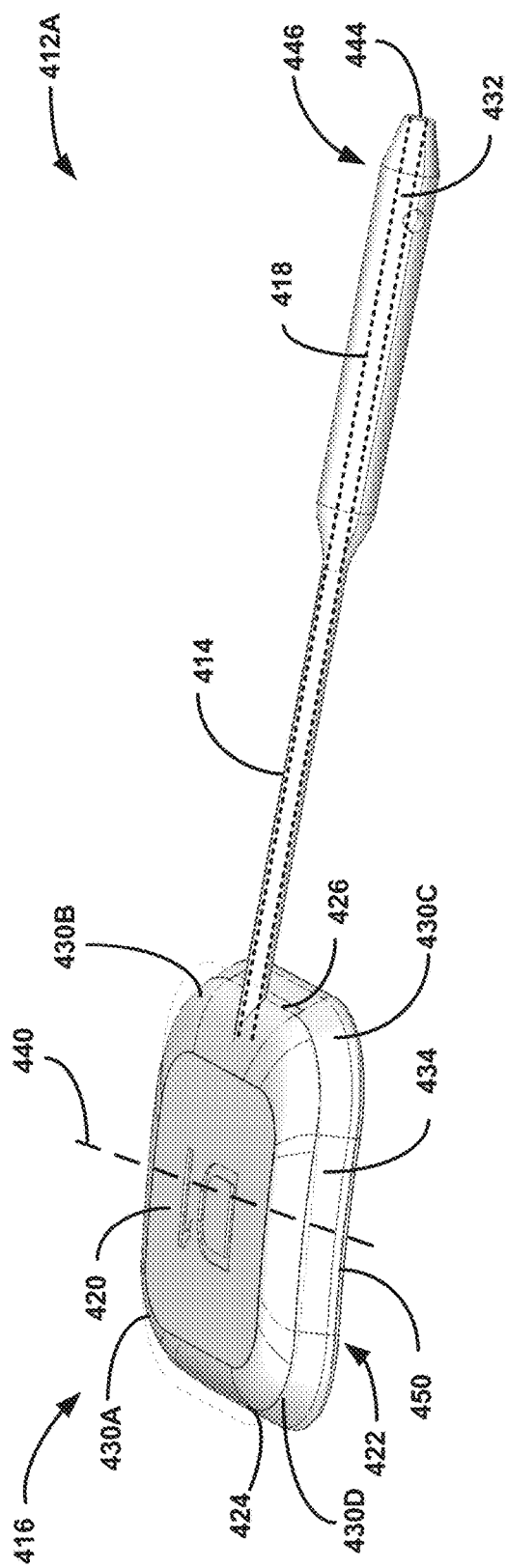
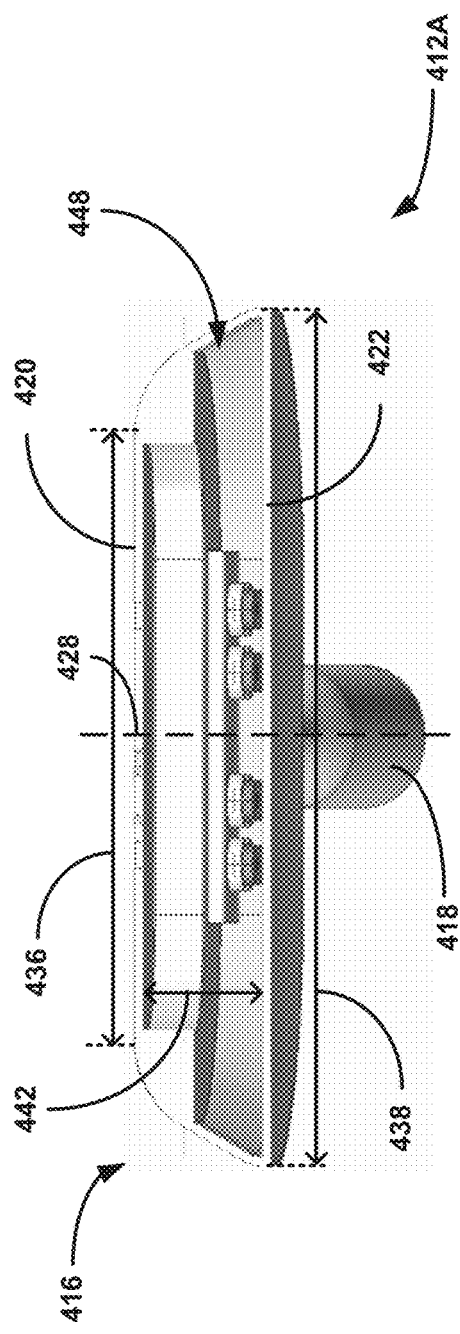
FIG. 25
FIG. 26

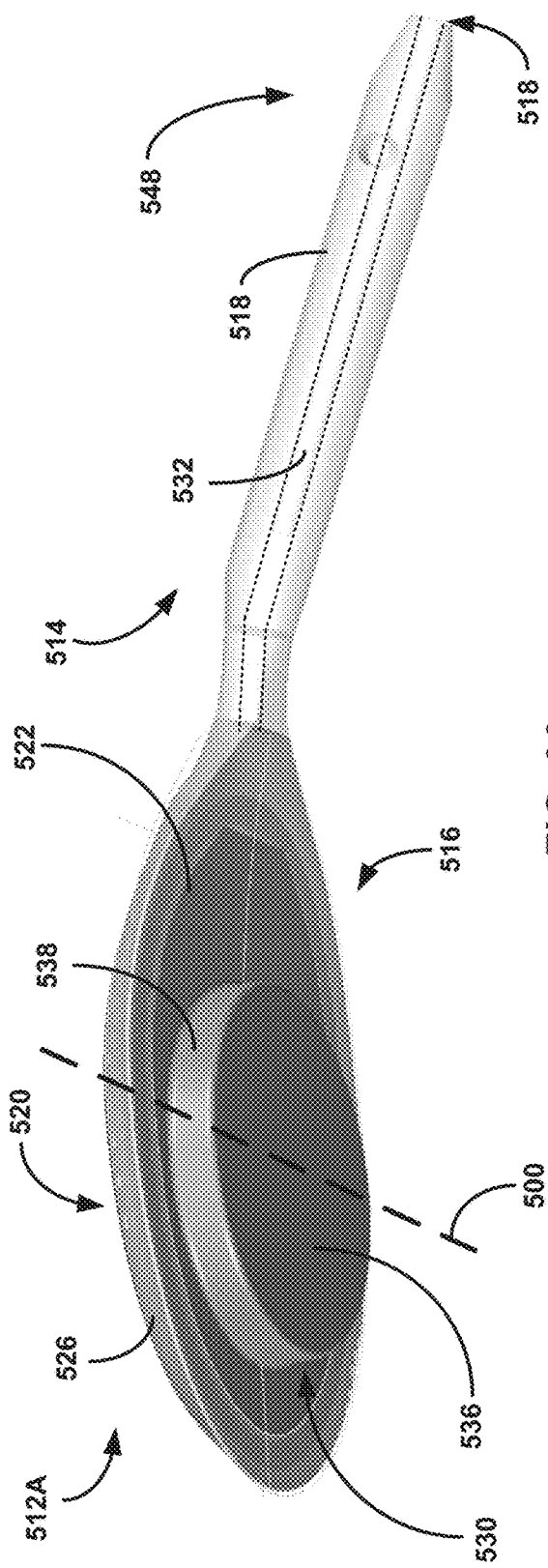
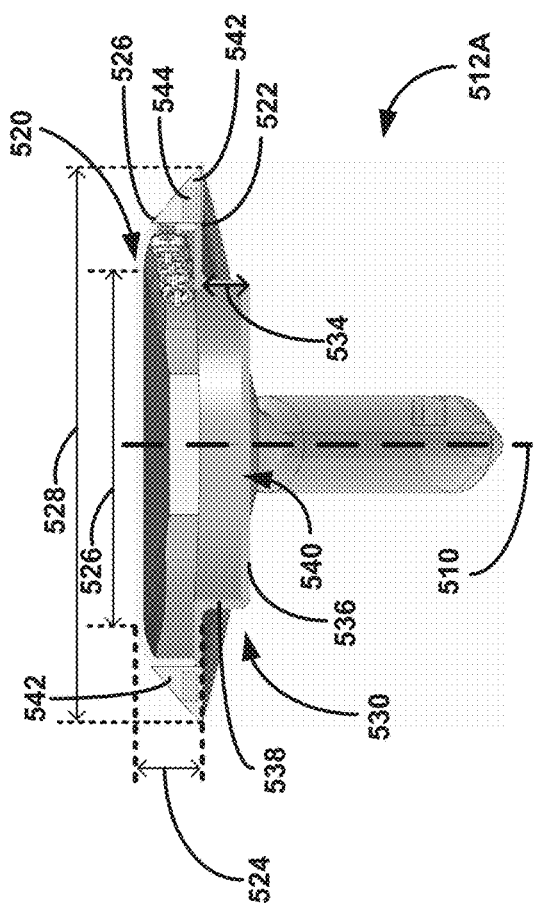
FIG. 33
FIG. 34

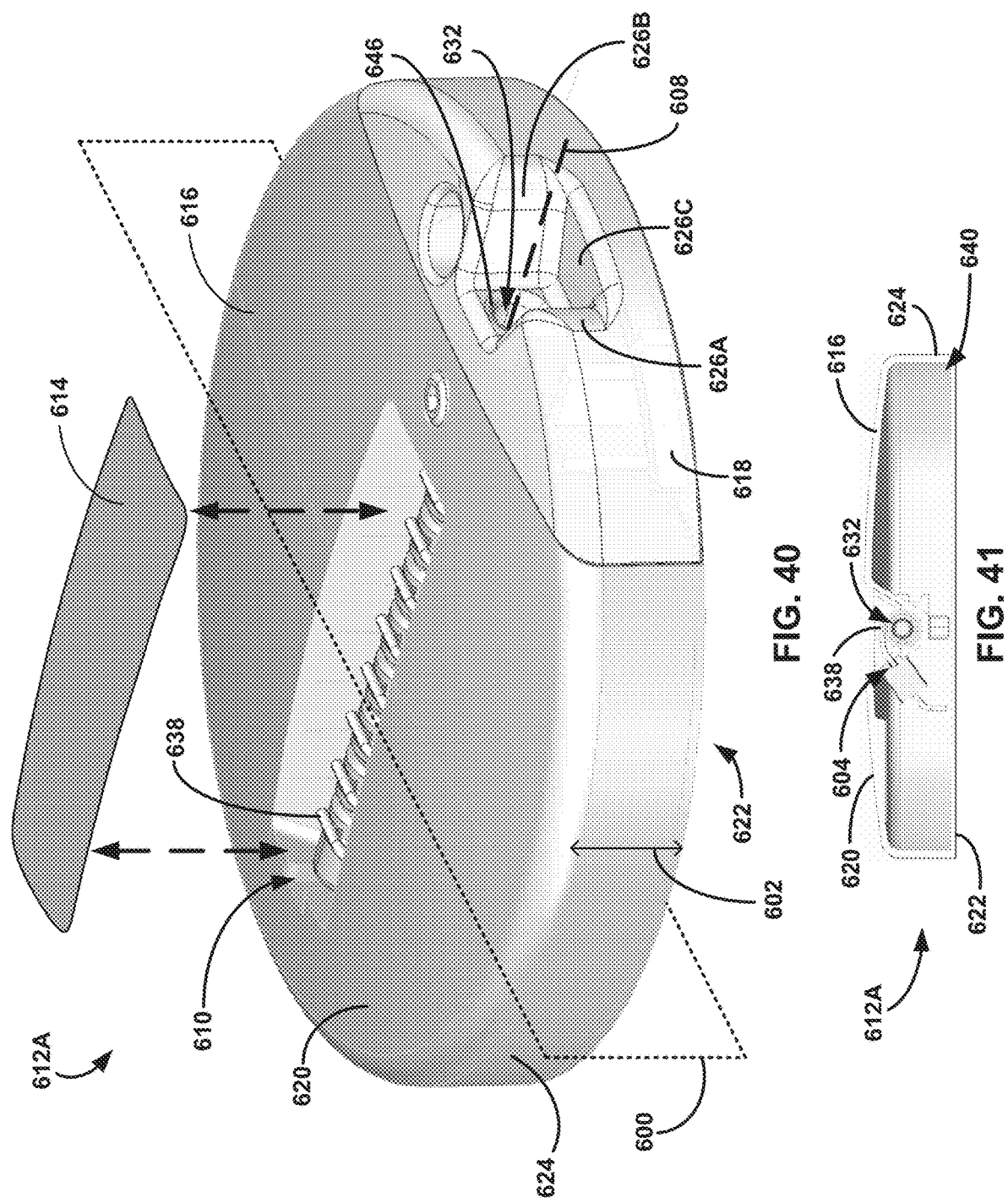

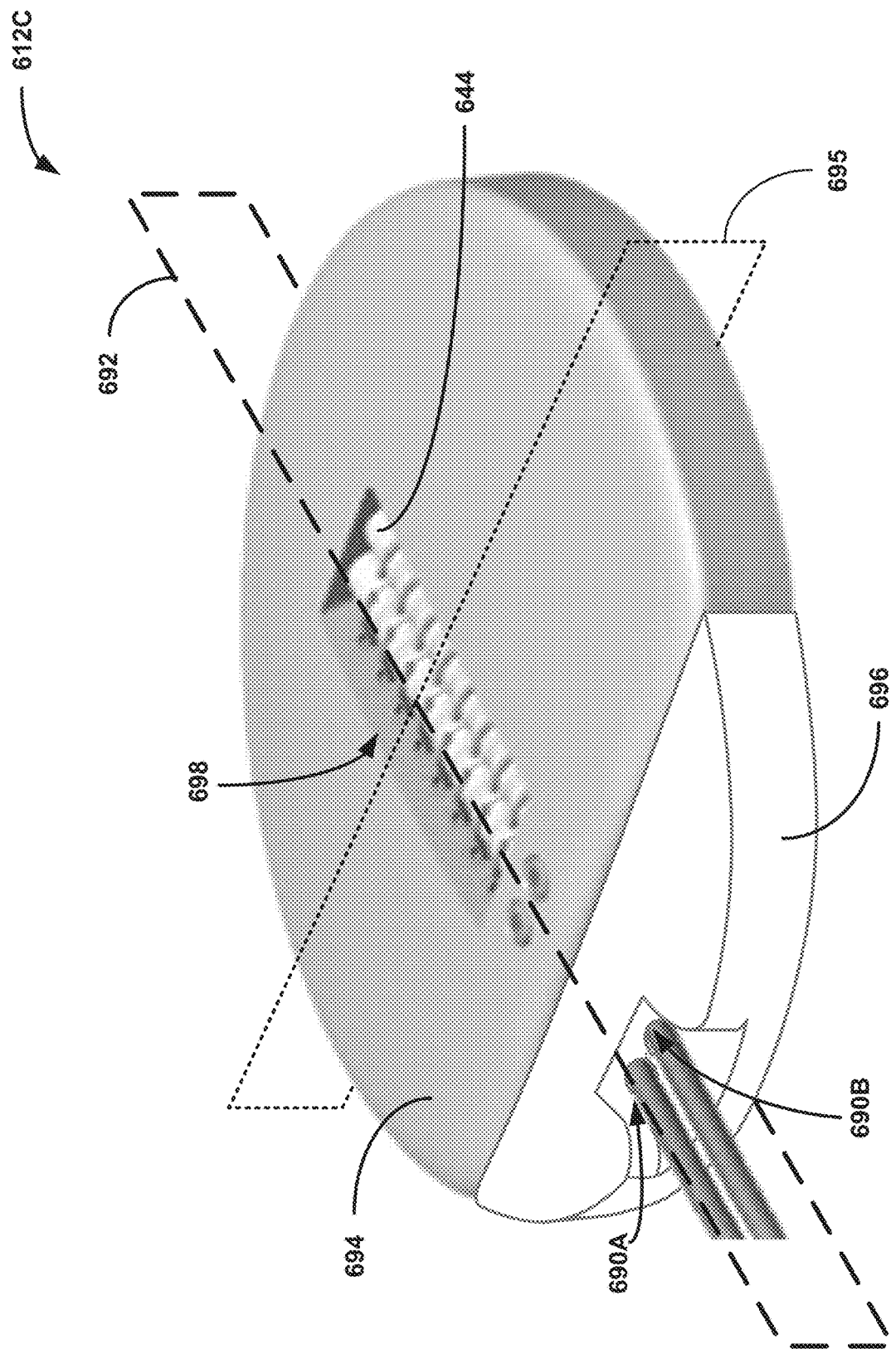

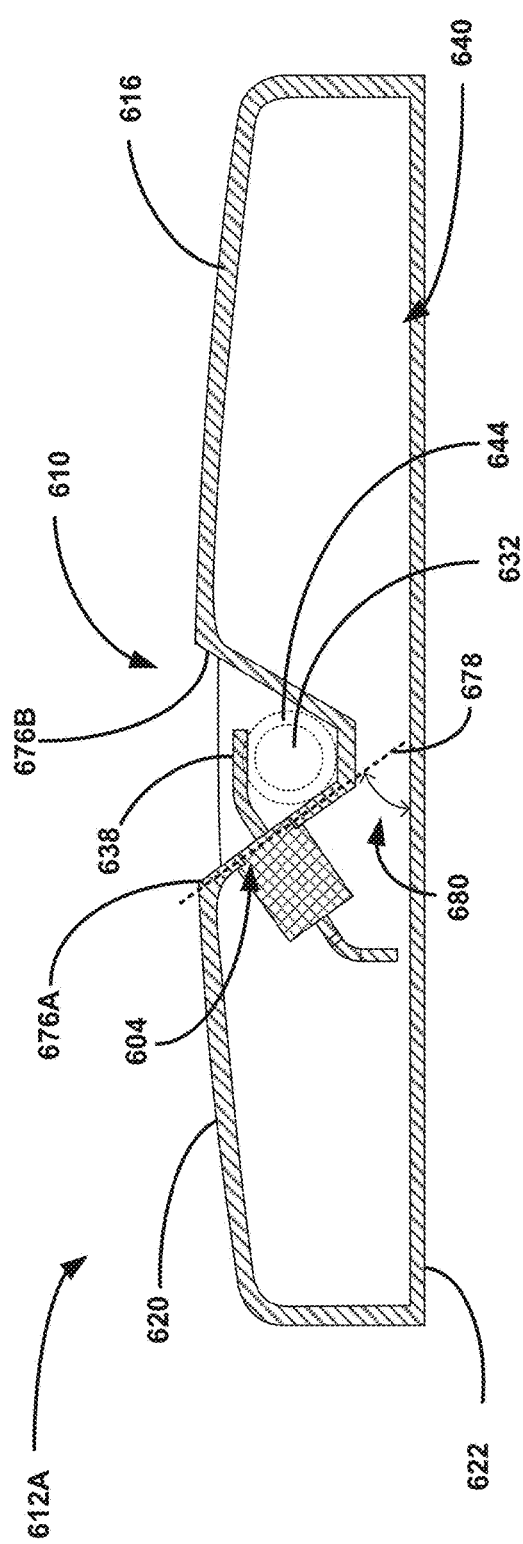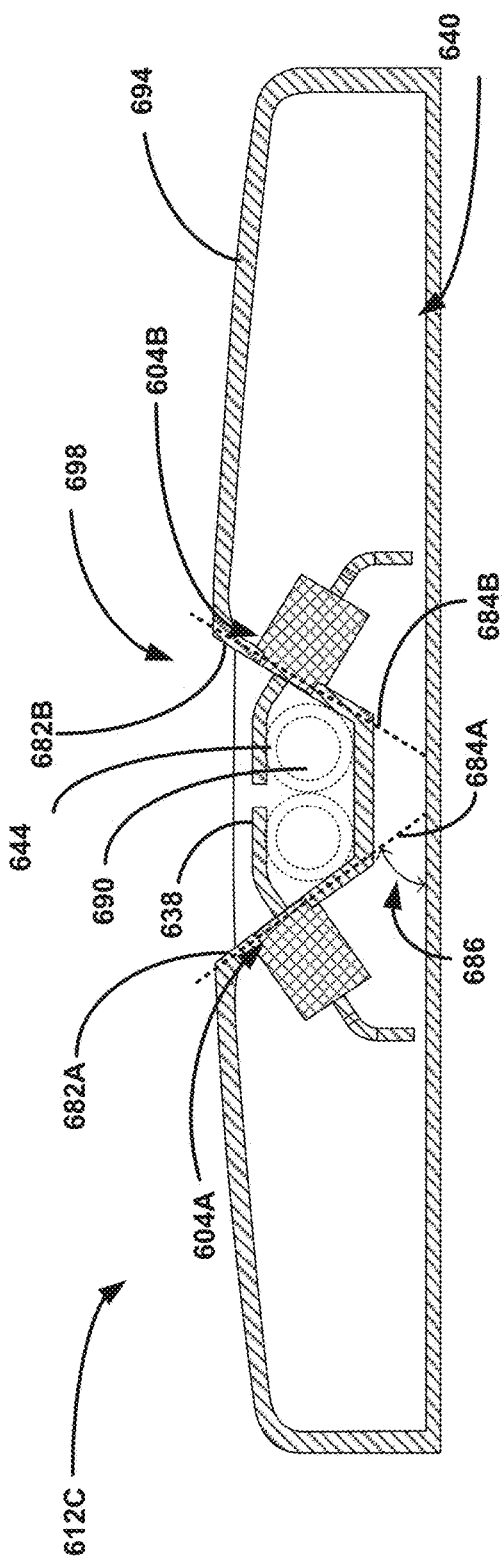

IMPLANTABLE MEDICAL DEVICE STRUCTURES

This application claims the benefit of U.S. Provisional Application Ser. No. 62/552,936, filed on Aug. 31, 2017, and U.S. Provisional Application Ser. No. 62/645,989, filed on Mar. 21, 2018, the entire content of each is incorporated herein by reference.

TECHNICAL FIELD

The disclosure relates to implantable medical devices, e.g., implantable medical device configured to be cranially mounted in a patient.

BACKGROUND

Medical devices may be external or implanted, and may be used to monitor a patient condition and/or deliver therapy to the patient. Delivering therapy to a patient may include delivering electrical stimulation therapy to patients to various tissue sites to treat a variety of symptoms or conditions such as chronic pain, tremors, Parkinson's disease, epilepsy, urinary or fecal incontinence, sexual dysfunction, obesity, or gastroparesis. Medical device may monitor a patient condition and/or delivery therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. Some examples of IMD components include a battery, a telemetry coil, and a circuit board that carries digital circuits. The circuit board may include integrated circuit chips and/or a microprocessor as well as analog circuit components.

SUMMARY

Aspects of the disclosure are directed to structures of implantable medical devices (IMDs). In some examples, an IMD may include one or more channels configured to receive a lead such that the received lead is electrically coupled to components (e.g., circuitry) within the IMD. The IMD may be configured to be implanted adjacent to the cranium of a patient, such as directly to an unbroken surface (e.g., a surface substantially without man-made deformations) of the cranium or in a recess carved or drilled into the cranium. The IMD may be configured to receive a lead such that, once electrically coupled to the IMD, the lead extends from the IMD with clearance between itself and the cranium. A first surface of the IMD that is configured to contact the cranium when the IMD is implanted may be configured to approximate the curvature of the cranium of the patient. Similarly, a second surface that is opposite the first surface of the IMD may be configured to approximate the curvature of the cranium of the patient. In some examples, the IMD may include one or more funneling walls that define a rounded and smooth transition from a sidewall of the housing to a surface that defines a mouth to the channels.

Aspects of this disclosure relate to an implantable medical device that includes a hermetically sealed housing that is configured to enclose internal components including at least processing circuitry configured to deliver deep brain stimulation, telemetry circuitry, a rechargeable power source, and a recharge coil configured to recharge the rechargeable power source. The housing defines two major surfaces that are generally parallel to each other. The housing defines one or more channels each configured to receive a lead and electrically couple the received lead to the internal components, each of the one or more channels extending substantially straight in to the housing along an axis generally parallel to the two major surfaces. The housing is configured to mount to a cranium of a patient such that at least one of the two major surfaces approximates a curvature of the cranium.

Other aspects of the disclosure relate to an implantable medical device include a hermetically sealed housing that is configured to enclose internal components including at least a processor and telemetry circuitry and a rechargeable power source that the implantable medical device is configured to recharge. The housing defines two major surfaces and a sidewall that extends between the two major surface. The two major surface are generally parallel to each other and define generally similar shapes. The housing defines one or more channels each configured to receive a lead and electrically couple the respective received lead to the internal components. Each of the one or more channels extend substantially straight in to the housing along an axis generally parallel to the two major surfaces, the housing configured to be mounted to a cranium of a patient. The implantable medical device also includes a mouth defined by the implantable medical device that provides access to the channel. The implantable medical device also includes one or more funneling walls that define a rounded and smooth transition from the sidewall to a surface that defines the mouth.

Other aspects of the disclosure relate to an implantable medical device that includes a housing that is configured to enclose internal components including at least a processor and a power source inside a hermetically sealed cavity, wherein one or more channels that extend through the housing are each configured to receive a lead and electrically couple the received lead to the internal components. The implantable medical device also includes a funneling section that is configured to be securely attached to the housing and defines a mouth to the one or more channels, wherein the housing and funneling section together define a first and a second major surface and a sidewall that extends between the first and the second major surface. The first major surface defines a substantially flat circle and the sidewall extends substantially perpendicular from the first major surface to the second major surface. The second major surface domes away from the first major surface as the second major surface extends radially in towards a center of the implantable medical device. The funneling section defines the mouth at a location that is radially recessed from the sidewall. The funneling section defines one or more funneling walls that define a rounded and smooth transition from the sidewall to the surface of funneling section that defines the mouth.

The details of one or more example are set forth in the accompanying drawings and the description below. Other features, objects, and advantages will be apparent from the description and drawings, and from the claims.

BRIEF DESCRIPTION OF DRAWINGS

FIGS. 6 and 7 are conceptual and schematic diagrams illustrating a side and top view of the IMD of FIG. 5.

FIGS. 10-12 are conceptual and schematic diagrams illustrating a top, side, and front view, respectively, of an example IMD with two channels for receiving two leads that is otherwise substantially similar to the IMD of FIG. 5.

FIGS. 13 and 14 are conceptual and schematic diagrams illustrating an isometric and front view, respectively, of an example IMD with one channel for receiving a lead.

FIGS. 17 and 18 are conceptual and schematic diagrams illustrating an isometric and front view, respectively, of an example IMD with two channels for receiving two leads that is otherwise substantially similar to the example IMD of FIGS. 13 and 14.

FIGS. 19 and 20 are conceptual and schematic diagrams illustrating an isometric and front view, respectively, of an example IMD with one channel for receiving a lead.

FIGS. 25 and 26 are conceptual and schematic diagrams illustrating an isometric and cross-sectional view, respectively, of an example IMD with one channel for receiving a lead.

FIGS. 33 and 34 are conceptual and schematic diagrams illustrating an isometric and front view, respectively, of an example IMD with one channel for receiving a lead.

FIGS. 40 and 41 are conceptual and schematic diagrams illustrating an isometric view and cross-sectional view, respectively, of an example IMD with one channel for receiving a lead.

FIG. 47 is a conceptual and schematic diagram illustrating an isometric view of an example IMD with two channels for receiving two leads that is otherwise similar to the IMDs of FIG. 40 and FIG. 44.

FIG. 48 is a conceptual diagram illustrating a cross-sectional view of the IMD of FIG. 40.

FIG. 49 is a conceptual diagram illustrating a cross-sectional view of the IMD of FIG. 47.

DETAILED DESCRIPTION

This disclosure is generally directed to implantable medical devices (IMDs) configured to be implanted into or adjacent to the cranium of a patient. IMDs may be implanted within a patient. Internal components (e.g., circuitry, memory, power sources, or the like) may be configured to deliver a therapy to the patient and/or monitor a parameter of the patient. The IMD may be configured to receive one or more leads such that the one or more leads are electrically coupled to the internal components. The one or more leads may be implanted at a target site within a patient to deliver a therapy to the patient and/or monitor a parameter of the patient via one or more electrodes. The IMD may be configured to receive the lead such that, once received, the lead extends from the IMD with at least the threshold amount of clearance with the cranium of the patient. The lead may extend straight out from the channel of the IMD (e.g., substantially parallel with a surface of the IMD that contacts the cranium of the patient) with at least the threshold amount of clearance between itself and the cranium of the patient. In some examples, the IMD may approximate the curvature of the cranium of the patient as secured to the cranium of the patient. The IMD may approximate the curvature of the cranium of the patient by defining one or more curved surfaces of the housing of the IMD, where the curvature of the curved surfaces approximates the curvature of the cranium. Alternatively, and/or additionally, the IMD may approximate the curvature of the cranium of the patient by defining one or more angles at which relatively flat surfaces of the housing intersect, where the angles of intersection approximate the curvature of the cranium.

Figure 1:
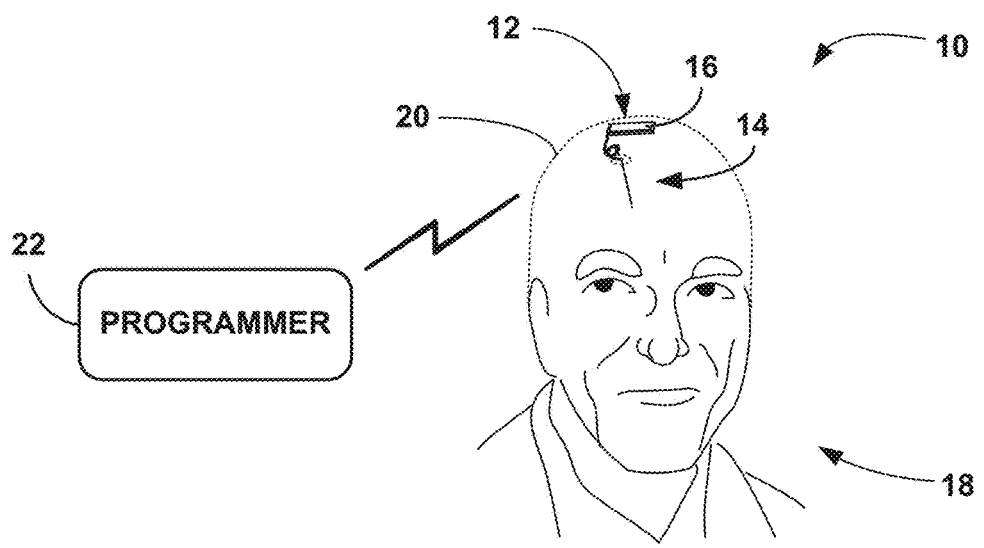
FIG. 1 is a conceptual and schematic diagram illustrating an example system that includes an implantable medical device (IMD) and a lead implanted into a brain of a patient.

FIG. 1 is a conceptual diagram illustrating an example system 10 that includes implantable medical device (IMD)

12 and lead 14. Techniques of this disclosure generally relate to housing 16 of IMD 12. Although the techniques described in this disclosure are generally applicable to a variety of medical devices including medical devices such as patient monitors, electrical stimulators, or drug delivery devices, this disclosure generally discusses techniques in the context of implantable neurostimulators for purposes of illustration. More particularly, the disclosure will refer to an implantable neurostimulation system for use in deep brain stimulation (DBS) therapy, but applies without limitation to other types of medical devices. For example, IMD 12 may be employed with leads 14 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, IMD 12 is not limited to implantation on cranium 20. Indeed, IMD 12 may be implanted anywhere within patient 18 (e.g., near the upper buttock, near the abdominal region, or near the pectoral region).

As shown in FIG. 1, system 10 includes IMD 12 in conjunction with patient 18, who is ordinarily a human patient. In some examples, IMD 12 may be a chronic electrical stimulator that remains implanted within patient 18 for weeks, months, or years. In the example of FIG. 1, lead 14 is received by IMD 12 and similarly implanted within patient 18. Lead 14 tunnels through tissue of the brain of patient 18 to a target spot in the brain of patient 18. IMD 12 and lead 14 may be directed to delivering DBS therapy, e.g., by sensing bioelectrical brain signals of the patient and/or delivering electrical stimulation to the brain of patient 18. In other examples, IMD 12 may be a temporary, or trial, stimulator used to screen or evaluate the efficacy of electrical stimulation for chronic therapy, or IMD 12 may be a device for local field potential (LFP) sensing to improve medical diagnostics or detection.

In the illustrated example, lead 14 received by IMD 12 extends through a hole within cranium 20 to access the brain of patient 18. In some examples, one or more leads 14 of system 10 may include a lead extension or other segments that may aid in implantation or positioning of lead 14. Lead 14 may include a plurality of electrodes, and IMD 12 may deliver stimulation to the brain of patient 18 via the electrodes. IMD 12 may receive any number of leads 14. A proximal end of lead(s) 14 may include a connector (not shown) that electrically couples to a header of IMD 12. In some examples, IMD 12 may receive two leads 14 that extend through a single hole in cranium 20 or extend through two separate holes in cranium 20 (e.g., to access separate hemispheres of the brain of patient 18). Alternatively, system 10 may include two IMDs 12 that each receive a single lead 14 that extends through a respective hole in cranium 20 to a respective hemisphere of the brain of patient 18. Alternatively, in certain examples IMD 12 may not receive any leads 14 (not depicted).

IMD 12 may be implanted adjacent to the outer surface of cranium 20, such that a surface of IMD 12 is configured to be secured to cranium 20. As a result of IMD 12 being configured to be implanted adjacent to cranium 20 of patient 18, system 10 may include relatively shorter leads 14 than if IMD 12 were implanted at a relatively more remote location. For example, in some situations one or more IMDs may be implanted at a location that is relatively more remote from the brain of patient 18, such as within a subclavicular region of patient 18. As a result of such a relatively more remote implantation site, it may be necessary to use a relatively longer lead than lead 14 to enable the remotely implanted IMD(s) to access the brain. As a result of IMD 12 being configured to be implanted adjacent to cranium 20 of patient 18, some problems associated with the use of long leads may be reduced or eliminated. These problems include the requirement of tunneling under the scalp and the skin of the neck, increased surgery and recovery time, an additional procedure under general anesthesia, risk of infection or skin erosion along the track through which the leads are tunneled, or risk of lead fracture due to torsional and other forces caused by normal head and neck movements. Further, relatively shorter leads 14 may advantageously improve the accuracy of any sensors gathering information or electrodes providing therapy by reducing noise attributable to leads 14. Shorter leads 14 may also advantageously reduce the negative effects of imaging techniques such as magnetic resonance imaging "MRI" on a person implanted with IMD 12.

As discussed above, lead 14 may include one or more electrodes that are implanted or otherwise placed adjacent to the target tissue. One or more electrodes may be disposed at a distal tip of lead 14 and/or at other positions at intermediate points along lead 14. Electrodes of lead 14 may transfer electrical stimulation (e.g., as generated by an electrical stimulation generator in IMD 12) to tissue of patient 18. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 14 will be described for purposes of illustration.

Using such electrodes of lead 14, IMD 12 may delivery electrical stimulation energy (e.g., current or voltage-based pulses) to the one or more targeted locations within patient 18 according to one or more therapy/stimulation program. The parameters for a therapy program that controls delivery of stimulation energy by IMD 12 may include information identifying a set of electrodes that have been selected for delivery of stimulation, the polarities of the selected electrodes, voltage or current amplitude, pulse rate, pulse shape, pulse width, or the like. Electrical stimulation may be delivered in the form of stimulation pulses or continuous waveforms. In this way IMD 12 may deliver stimulation to the brain of patient 18 to, for example, provide deep brain stimulation (DBS) therapy, or to stimulate the cortex of the brain. Cortical stimulation may involve stimulation of the motor cortex. IMD 12 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

Although lead 14 is described as generally delivering or transmitting electrical stimulation signals, lead 14 may additionally or alternatively transmit electrical signals from patient 18 to IMD 12 for monitoring. For example, IMD 12 may additionally or alternatively monitor one or more physiological parameters and/or the activity of patient 18, and may include sensors for these purposes. The one or more sensors may be provided in addition to, or in place of, therapy delivery by lead 14. Using these sensors, IMD 12 may utilize detected nerve impulses to diagnose the condition of patient 18 or adjust the delivered stimulation therapy. For example, IMD 12 may additionally or alternatively monitor one or more physiological parameters and/or the activity of patient 18. Where a therapy is delivered, IMD 12 may operate in an open loop mode (also referred to as non-responsive operation), or in a closed loop mode (also referred to as responsive). IMD 12 may also provide warnings based on the monitoring.

Alternatively, or additionally, lead 14 and IMD 12 may be configured to provide other types of therapy through the delivery of a therapeutic agent to the target tissue of patient 18. For example, IMD 12 can additionally or alternatively deliver a therapeutic agent such as a pharmaceutical, biological, or genetic agent. In these examples, lead 14 may function as a catheter or IMD 12 may be otherwise mechanically attached to a catheter. Further, IMD 12 may include a pump to deliver the therapeutic agent via the catheter.

A user, such as a clinician or patient 18, may interact with a user interface of an external programmer 22 to program IMD 12. Programming of IMD 12 may refer generally to the generation and transfer of commands, programs, or other information to control the operation of IMD 12. For example, programmer 22 may transmit programs, parameter adjustments, program selections, group selections, or other information to control the operation of IMD 12, e.g., by wireless telemetry or wired connection. In some cases, programmer 22 may be characterized as a physician or clinician programmer if it is primarily intended for use by a physician or clinician, respectively. Programmer 22 may be characterized as a patient programmer if it is primarily intended for use by a patient. A patient programmer is generally accessible to patient 18 and, in many cases, may be a portable device that may accompany the patient throughout the patient's daily routine. In general, a physician or clinician programmer 22 may support selection and generation of programs by a clinician for use by IMD 12, whereas a patient programmer may support adjustment and selection of such programs by a patient during ordinary use. In this manner, a user may program and charge IMD 12 using one device, or multiple devices.

IMD 12 may be constructed of any polymer, metal, or composite material sufficient to house the components of IMD 12 (e.g., components illustrated in FIG. 3) within patient 18. In this example, IMD 12 may be constructed with a biocompatible housing, such as titanium (e.g., titanium grade 23, grade 5, grade 9, or commercially pure titanium) or stainless steel, or a polymeric material such as silicone or polyurethane, or a combination thereof. In some examples, IMD 12 may include housing 16 that is made out of relatively rigid biocompatible material (e.g., titanium or stainless steel) and a tether component that is made out of a relatively flexible biocompatible material (e.g., silicone or low-density polyethylene (LDPE)) and receives lead 14. The housing (and tether, where applicable) of IMD 12 may be configured to provide a hermetic seal for components. In addition, the housing of IMD 12 may be selected of a material that facilitates receiving energy (e.g., harnessing current from an electro-magnetic field) to charge an internal power source. Materials and construction of IMDs 12 of this disclosure may selected such that IMDs 12 are MRI compatible, such that a patient that has IMD 12 secured to her may undergo an MRI with substantially no damage to either IMD 12 or the MRI device.

Figure 2:
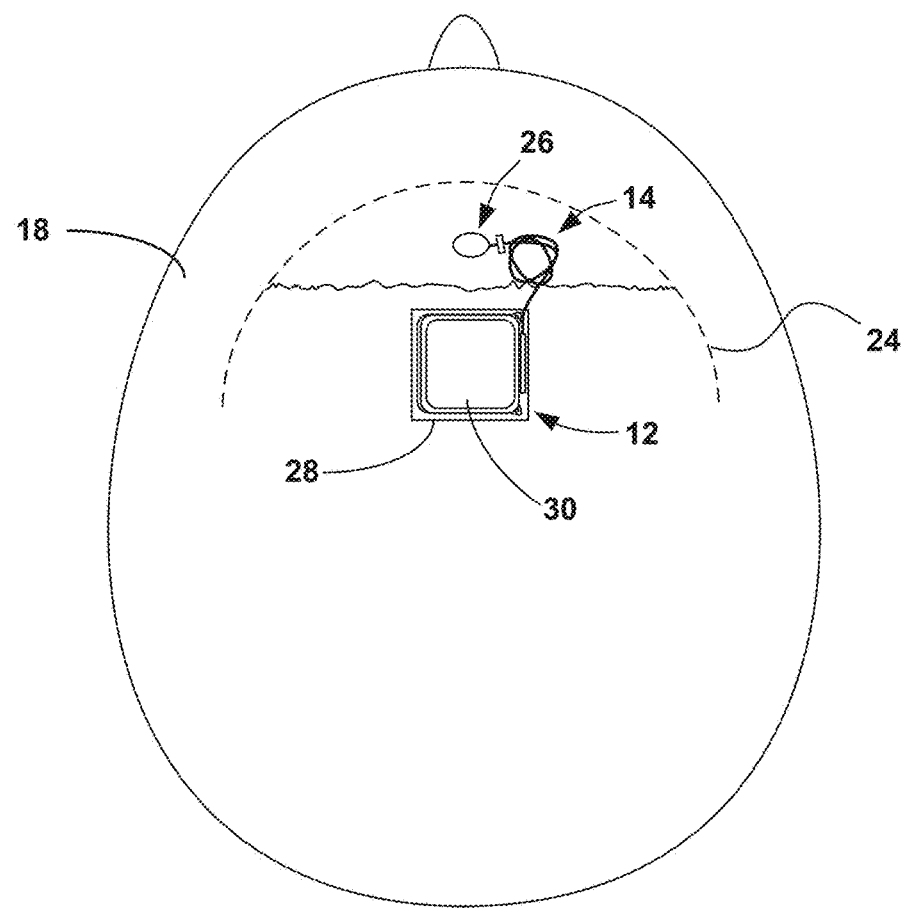
FIG. 2 is a conceptual and schematic diagram of a recess in the cranium of a patient for receiving the IMD of FIG. 1.

FIG. 2 is a top-view diagram further illustrating IMD 12 implanted on cranium 20 of the patient 18. The location on cranium 20 at which IMD 12 is illustrated as implanted in FIG. 2 is depicted for purposes of illustration only, as IMD 12 can be implanted anywhere on the surface of cranium 20. In order to implant IMD 12 on cranium 20, a clinician may make an incision 24 through the scalp of patient 18, and pull back a resulting flap of skin to expose the desired area of cranium 20. The incision may, as shown in FIG. 2, be generally shaped like a "C." Such an incision is commonly referred to as a "C-flap" incision. When system 10 includes more than one IMD 12, a clinician may locate both IMDs 12 under the same region of cranium 20 under the flap of skin.

Burr hole 26 may be drilled through cranium 20, after which lead 14 may be inserted through burr hole 26 and into the brain of patient 18. As discussed above, in examples where system 10 includes more than one lead 14, more than one burr hole 26 may be drilled through cranium 20. In some examples caps may be placed over burr holes 26. One or more leads 14 may be connected to IMD 12, either directly or via a lead extension, and IMD 12 may be placed at least partially within a pocket formed using a hand or a tool beneath the scalp adjacent burr hole(s) 26. In some examples, IMD 12 is placed entirely or partially within a recess 28 drilled partially into cranium 20. Recess 28 may allow housing 16 of IMD 12 to sit closer to an outside surface of cranium 20, reducing a profile of IMD 12 relative to the outside surface of cranium 20. The shape and size of housing 16 may dictate the shape and size of recess 28. In some examples, IMD 12 may include a curved or angled housing 16 to approximate the curvature of cranium 20. Configuring housing 16 to approximate the curvature of cranium 20 may further reduce the profile of IMD 12 and/or increase how securely IMD 12 may be attached to cranium 20.

The depicted direction and manner of how lead 14 extends from IMD 12 is depicted for purposes of illustration only, as lead 14 may extend from IMD 12 according to any manner that is consistent with the techniques described herein. IMD 12 may include a channel which receives lead 14, such that lead 14 extends from this channel. IMD 12 may define such a channel such that lead 14 extends from the channel with at least a threshold amount of clearance between lead 14 and cranium 20. Further, in some examples IMD 12 may include a flexible tether that defines the channel(s) that receive lead(s) 14, enabling lead 14 to flex towards burr hole 26 while coupling with IMD 12.

In some examples, once positioned as desired on (or partially submerged into) cranium 20 within the pocket, IMD 12 may then be fixed to cranium 20 using an attachment mechanism such as bone screws, suturing directly to the surrounding tissue, suturing to mechanical components (e.g., anchors) that are secured (screwed) into the cranium, securing with various types of straps (e.g., nonmetallic straps) that are screwed down, or the like. The skin flap may be closed over IMD 12, and the incision may be stapled or sutured.

Figure 3:
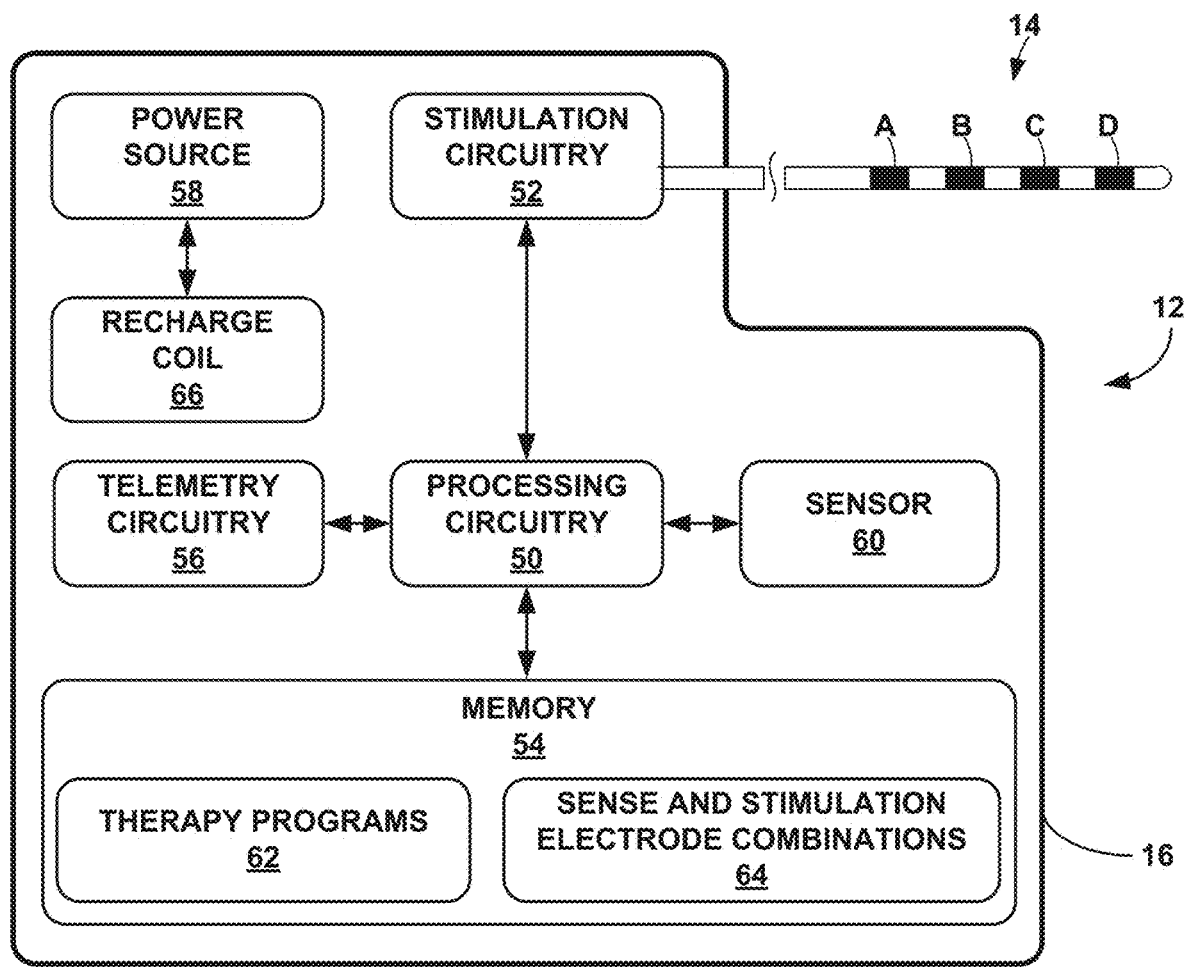
FIG. 3 is a conceptual and schematic block diagram of the IMD of FIG. 1.

FIG. 3 is a block diagram illustrating example components of IMD 12. In the example of FIG. 3, IMD 12 includes processing circuitry 50, stimulation circuitry 52, memory 54, telemetry circuitry 56, power source 58, sensor 60, and recharge coil 66. In other examples, IMD 12 may include a greater or fewer number of components. For one example, in some instances IMD 12 may not include sensor 60. While in FIG. 3 most components of IMD 12 are depicted as contained within in a single substantially contiguous compartment of housing 16, in other examples components of IMD 12 may be contained within IMD 12 in other configurations. For example, in some instances components of IMD may be contained within a plurality of housings of IMD 12, or some components may be secured partially or fully outside of an internal hermetically sealed compartment of housing 16 and electrically coupled to other components within a compartment of housing 16 as described herein.

In general, IMD 12 may comprise any suitable arrangement of hardware, alone or in combination with software and/or firmware, to perform the various techniques described herein attributed to IMD 12 and processing circuitry 50. In various examples, IMD 12 may include one or more processing circuits 50, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 12 also, in various examples, may include memory 54, such as random-access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Memory 54 may store therapy programs 62, sense or stimulation electrode combinations 64, or other instructions that specify therapy parameter values for the therapy provided by stimulation circuitry 52 and IMD 12. Moreover, although processing circuitry 50, stimulation circuitry 52, and telemetry circuitry 56 are described as separate portions of circuitry, in some examples processing circuitry 50, stimulation circuitry 52, and/or telemetry circuitry 56 may be fully or partially integrated with each other. In some examples, processing circuitry 50, stimulation circuitry 52, and/or telemetry circuitry 56 correspond to individual hardware units, such as ASICs, DSPs, FPGAs, or other hardware units.

Stimulation circuitry 52 may generate and deliver electrical stimulation under the control of processing circuitry 50. In some examples, processing circuitry 50 controls stimulation circuitry 52 by accessing memory 54 to selectively access and load at least one of the therapy programs 62 to stimulation circuitry 52. For example, in operation, processing circuitry 50 may access memory 54 to load one of the therapy programs 62 to stimulation circuitry 52. In such examples, relevant stimulation parameters may include a voltage amplitude, a current amplitude, a pulse rate, a pulse width, a duty cycle, or the combination of electrodes 14A, 14B, 14C, and 14D as stored in stimulation electrode combinations 64 that stimulation circuitry 52 uses to deliver the electrical stimulation signal. Although stimulation circuitry 52 may be configured to generate and deliver electrical stimulation therapy via one or more of electrodes 14A, 14B, 14C, and 14D of lead 14, stimulation circuitry 52 may be configured to provide different therapy to patient 18. For example, stimulation circuitry 52 may be configured to deliver drug delivery therapy via a catheter. These and other therapies may be provided by IMD 12.

Power source 58 may be rechargeable through the use of recharge coil 66. Recharge coil 66, which may be a coil of wire or other device capable of inductive coupling with a primary coil disposed external to patient 18. Recharge coil 66 may include a winding of wire configured such that an electrical current can be induced within the from a magnetic field. The induced electrical current may then be used to recharge power source 58. In this manner, the electrical current may be induced in recharge coil 66 associated with power source 58. The induction may be caused by electrical current generated in the primary coil of an external charging device and based on the selected power level. The coupling between recharge coil 66 and the external charging coil may be dependent upon the alignment of the two coils. In some examples, the coupling efficiency increases when the two coils share a common axis and are in close proximity to each other. The external charging device and/or IMD 12 may provide one or more audible tones or visual indications of the alignment.

Although inductive coupling is generally described as the method for recharging rechargeable power source 58, other wireless energy transfer techniques may alternatively be used. Any of these techniques may generate heat in IMD 12 such that the charging process can be controlled using the calculated cumulative thermal dose as feedback.

IMD 12 may include one or more circuits that filter and/or transform the electrical signal induced in recharge coil 66 to an electrical signal capable of recharging power source 58. For example, in alternating current induction, IMD 12 may include a half-wave rectifier circuit and/or a full-wave rectifier circuit configured to convert alternating current from the induction to a direct current for power source 58. The full-wave rectifier circuit may be more efficient at converting the induced energy for power source 58. However, a half-wave rectifier circuit may be used to store energy in power source 58 at a slower rate. In some examples, IMD 12 may include both a full-wave rectifier circuit and a half-wave rectifier circuit such that IMD 12 may switch between each circuit to control the charging rate of power source 58 and temperature of IMD 12.

In some examples, IMD 12 may include a measurement circuit configured to measure the current and/or voltage induced during inductive coupling. This measurement may be used to measure or calculate the power transmitted to IMD 12 from an external charging device. In some examples, the transmitted power may be used to approximate the temperature of IMD 12 and that of the surrounding tissue. This method may be used to indirectly measure the temperature of tissue in contact with the housing of IMD 12. In other examples, IMD 12 may estimate the transmitted power using the measured voltage or current.

Power source 58 may include one or more capacitors, batteries, or other energy storage devices. Power source 58 may then deliver operating power to the components of IMD 12. In some examples, power source 58 may include a power generation circuit to produce the operating power. Power source 58 may be configured to operate through hundreds or thousands of discharge and recharge cycles. Power source 58 may also be configured to provide operational power to IMD 12 during the recharge process. In some examples, power source 58 may be constructed with materials to reduce the amount of heat generated during charging. In other examples, IMD 12 may be constructed of materials that may help dissipate generated heat at power source 58 and/or recharge coil 66 over a larger surface area of the housing of IMD 12.

Although power source 58 and recharge coil 66 are shown as contained within housing 16 of IMD 12, at least one of these components may be disposed outside of the housing 16. For example, recharge coil 66 may be disposed outside of housing 16 of IMD 12 (e.g., in an overmolding of the house) to facilitate better coupling between recharge coil 66 and a charging coil of an external charging device. Alternatively, recharge coil 66 may be located within a tether external to housing 16 of IMD 12. Locating recharge coil 66 outside of housing 16 may improve an ability of recharge coil 66 to receive signals without being blocked by materials of housing 16. Further, locating recharge coil 66 relatively further away from housing 16 may increase the available bandwidth of frequencies with which power source 58 may be recharged. Put differently, these different configurations of IMD 12 components may allow IMD 12 to be implanted in different anatomical spaces or facilitate better inductive coupling alignment between recharge coil 66 and the external charging coil.

IMD 12 include one or more sensors 60. Sensor 60 may include one or more sensing elements that sense values of a respective patient or IMD 12 parameter. For example, sensor 60 may include one or more accelerometers, optical sensors, chemical sensors, temperature sensors, pressure sensors, or any other types of sensors. IMD 12 may include additional sensors that are enclosed within the housing of IMD 12 and/or are located outside of the housing of IMD 12 and electrically coupled to components within the housing via one of leads 14 or other leads. For example, IMD 12 may receive sensor signals wirelessly from remote sensors via telemetry circuitry 56. In some examples, one or more of these remote sensors may be external to patient (e.g., carried on the external surface of the skin, attached to clothing, or otherwise positioned external to the patient). Sensor 60 may output patient or IMD parameter values that may be used as feedback to control delivery of therapy or to otherwise manage IMD.

For example, sensor 60 may be a temperature sensor that sensing temperatures during recharging. As a temperature sensor, sensor 60 may include one or more temperature sensors (e.g., thermocouples or thermistors) configured to measure the temperature of IMD 12. Temperature sensor 60 may be disposed internal of the housing of IMD 12, contacting the housing, formed as a part of housing 16, or disposed external of housing 16. As described herein, temperature sensor 60 may be used to directly measure the temperature of IMD 12 and/or tissue surrounding and/or contacting the housing of IMD 12. Processing circuitry 50 (or an external charging device) may use this temperature measurement as the tissue temperature feedback to determine the cumulative thermal dose provided to tissue during charging of power source 58. Although a single temperature sensor may be adequate, multiple temperature sensors may provide a better temperature gradient or average temperature of IMD 12. The various temperatures of IMD 12 may also be modeled and provided to determine the cumulative thermal dose. Although processing circuitry 50 may continually measure temperature using sensor 60, processing circuitry 50 may conserve energy by only measuring temperature during recharge sessions. Further, temperature may be sampled at a rate necessary to calculate the cumulative thermal dose, but the sampling rate may be reduced to conserve power as appropriate.

Processing circuitry 50 may also control the exchange of information with an external charging device and/or an external programmer using telemetry circuitry 56. Telemetry circuitry 56 may be configured for wireless communication using radio frequency protocols or inductive communication protocols. Telemetry circuitry 56 may include one or more antennas configured to communicate with the programmer, for example. Processing circuitry 50 may transmit operational information and receive therapy programs 62 or therapy parameter adjustments via telemetry circuitry 56. Also, in some examples, IMD 12 may communicate with other implanted devices, such as stimulators, control devices, or sensors, via telemetry circuitry 56. In addition, telemetry circuitry 56 may be configured to transmit the measured values from sensor 60. In other examples, processing circuitry 50 may transmit additional information to an external charging device related to the operation of power source 58. For example, processing circuitry 50 may use telemetry circuitry 56 to transmit indications that power source 58 is completely charged, power source 58 is fully discharged, or any other charge status of power source 58. Processing circuitry 50 may also transmit information to the external charging device that indicates any problems or errors with power source 58 that may prevent power source 58 from providing operational power to the components of IMD 12.

Examples of local wireless communication techniques that may be employed to facilitate communication between an external device and IMD 12 include RF communication according to the 802.11 or Bluetooth specification sets or other standard or proprietary telemetry protocols. In this manner, other external devices may be capable of communicating with an external charging device without needing to establish a secure wireless connection. As described herein, telemetry circuitry 56 may be configured to receive a measured tissue temperature from IMD 12. The tissue temperature may be measured adjacent to rechargeable power source 58, such as near the housing of IMD 12 or external of the housing. Although IMD 12 may measure the tissue temperature, one or more different implantable temperature sensors (e.g., standalone implantable temperature sensing devices) may independently measure the tissue temperature at different positions and transmit the temperature to an external charging device. In some examples, multiple temperature readings by IMD 12 may be averaged or otherwise used to produce a single temperature value that is transmitted to an external charging device. The temperature may be sampled and/or transmitted at different rates, e.g., on the order of microseconds, milliseconds, seconds, minutes, or even hours. Processing circuitry 50 may then use the received tissue temperature to calculate the cumulative thermal dose.

Figure 4:
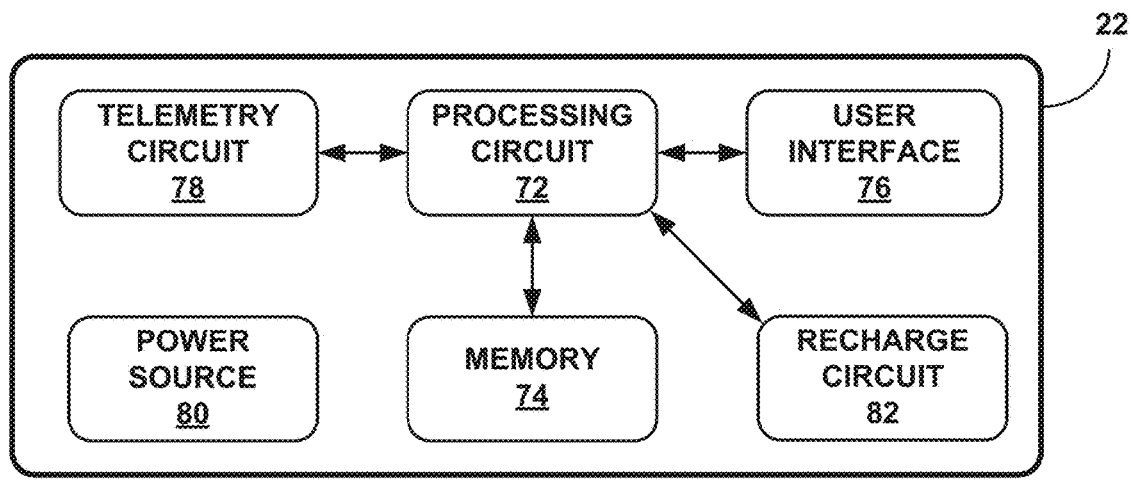
FIG. 4 is a conceptual and schematic block diagram of the example external programmer of FIG. 1.

FIG. 4 is a block diagram of external programmer 22 of FIG. 1. Programmer 22 may be a clinician programmer or a patient programmer. Although programmer 22 may generally be described as a hand-held device, programmer 22 may be a larger portable device or a more stationary device. In addition, programmer 22 may be included as part of an external charging device or include the functionality of an external charging device. As illustrated in FIG. 4, programmer 22 may include processing circuit 72, memory 74, user interface 76, telemetry circuit 78, power source 80, and recharge circuit 82. Memory 74 may store instructions that, when executed by processing circuit 72, cause processing circuit 72 and programmer 22 to provide the functionality ascribed to programmer 22 throughout this disclosure. Each of these components, or circuitry, may include electrical circuitry that is configured to perform some or all of the functionality described herein. For example, processing circuit 72 may include one or more processors configured to perform the processes discussed with respect to processing circuit 72.

As shown, programmer 22 may include any suitable arrangement of hardware, alone or in combination with software and/or firmware, to perform the techniques attributed to programmer 22, and processing circuit 72, user interface 76, telemetry circuit 78, and recharge circuit 82 of programmer 22. In various examples, programmer 22 may include one or more processors, such as one or more microprocessors, DSPs, ASICs, FPGAs, or any other equivalent integrated or discrete logic circuitry, as well as any combinations of such components. Programmer 22 also, in various examples, may include a memory 74, such as RAM, ROM, PROM, EPROM, EEPROM, flash memory, a hard disk, a CD-ROM, comprising executable instructions for causing the one or more processors to perform the actions attributed to them. Moreover, although processing circuit 72, telemetry circuit 78, and recharge circuit 82 are described as separate circuits, in some examples, processing circuit 72, telemetry circuit 78, and/or recharge circuit 82 may be functionally integrated. In some examples, processing circuit 72 telemetry circuit 78, and/or recharge circuit 82 correspond to individual hardware units, such as ASICs, DSPs, FPGAs, or other hardware units.

Memory 74 (e.g., a storage device) may store instructions that, when executed by processing circuit 72, cause processing circuit 72 and programmer 22 to provide the functionality ascribed to programmer 22 throughout this disclosure. For example, memory 74 may include instructions that cause processing circuit 72 to obtain one or more parameters from memory, or receive a user input and send a corresponding command to IMD 12, or instructions for any other functionality. In addition, memory 74 may include a plurality of therapy programs 62, where each program includes one or more parameters that defines stimulation therapy.

User interface 76 may include a button or keypad, lights, a speaker for voice commands, a display, such as a liquid crystal (LCD), light-emitting diode (LED), or organic light-emitting diode (OLED). In some examples, the display may be a touch screen. User interface 76 may be configured to display any information related to the delivery of stimulation therapy, identified patient behaviors, sensed patient parameter values, patient behavior criteria, or any other such information. User interface 76 may also receive user input via user interface 76. The input may be, for example, in the form of pressing a button on a keypad or selecting an icon from a touch screen. The input may request starting or stopping electrical stimulation, or the input may request some other change to the delivery of electrical stimulation.

Telemetry circuit 78 may support wireless communication between IMD 12 and programmer 22 under the control of processing circuit 72. Telemetry circuit 78 may also be configured to communicate with another computing device via wireless communication techniques, or direct communication through a wired connection. In some examples, telemetry circuit 78 provides wireless communication via an RF or proximal inductive medium. In some examples, telemetry circuit 78 includes an antenna, which may take on a variety of forms, such as an internal or external antenna.

Examples of local wireless communication techniques that may be employed to facilitate communication between programmer 22 and IMD 12 include RF communication according to the 802.11 or Bluetooth specification sets or other standard or proprietary telemetry protocols. In this manner, other external devices may be capable of communicating with programmer 22 without needing to establish a secure wireless connection. As described herein, telemetry circuit 78 may be configured to transmit a spatial electrode movement pattern or other stimulation parameter values to IMD 12 for delivery of stimulation therapy.

In some examples, selection of therapy parameters or therapy programs may be transmitted to a medical device (e.g., IMD 12) for delivery to patient 18. In other examples, the therapy may include medication, activities, or other instructions that patient 18 must perform themselves or a caregiver perform for patient 18. In some examples, programmer 22 may provide visual, audible, and/or tactile notifications that indicate there are new instructions. Programmer 22 may require receiving user input acknowledging that the instructions have been completed in some examples.

Recharge circuit 82 may control or provide recharging power for IMD 12. For example, recharge circuit 82 may be configured to create an electromagnetic field for IMD 12. Recharge coil 66 of IMD 12 may be exposed to the electromagnetic field as created by recharge circuit 82 and may therein use this electromagnetic field to recharge power source 58 of IMD 12. Recharge circuit 82 may use power source 80 and one or more coils (not depicted) of programmer 22 to create the electromagnetic field. In some examples, processing circuit 72 may cause recharge circuit 82 to create the recharging electromagnetic field, such as in response to an input received from user interface 76. Recharge circuit 82 may use telemetry circuit 78 to receive feedback from IMD 12 during charging to modify an electromagnetic field created by recharge circuit 82. For example, recharge circuit 82 may increase or decrease a magnitude of a created recharge electromagnetic field for charging power source 58 in response to receiving notification(s) through telemetry circuit 78 and from telemetry circuitry 56 that IMD 12 is below or above one or more temperature thresholds, for example.

Figure 5:
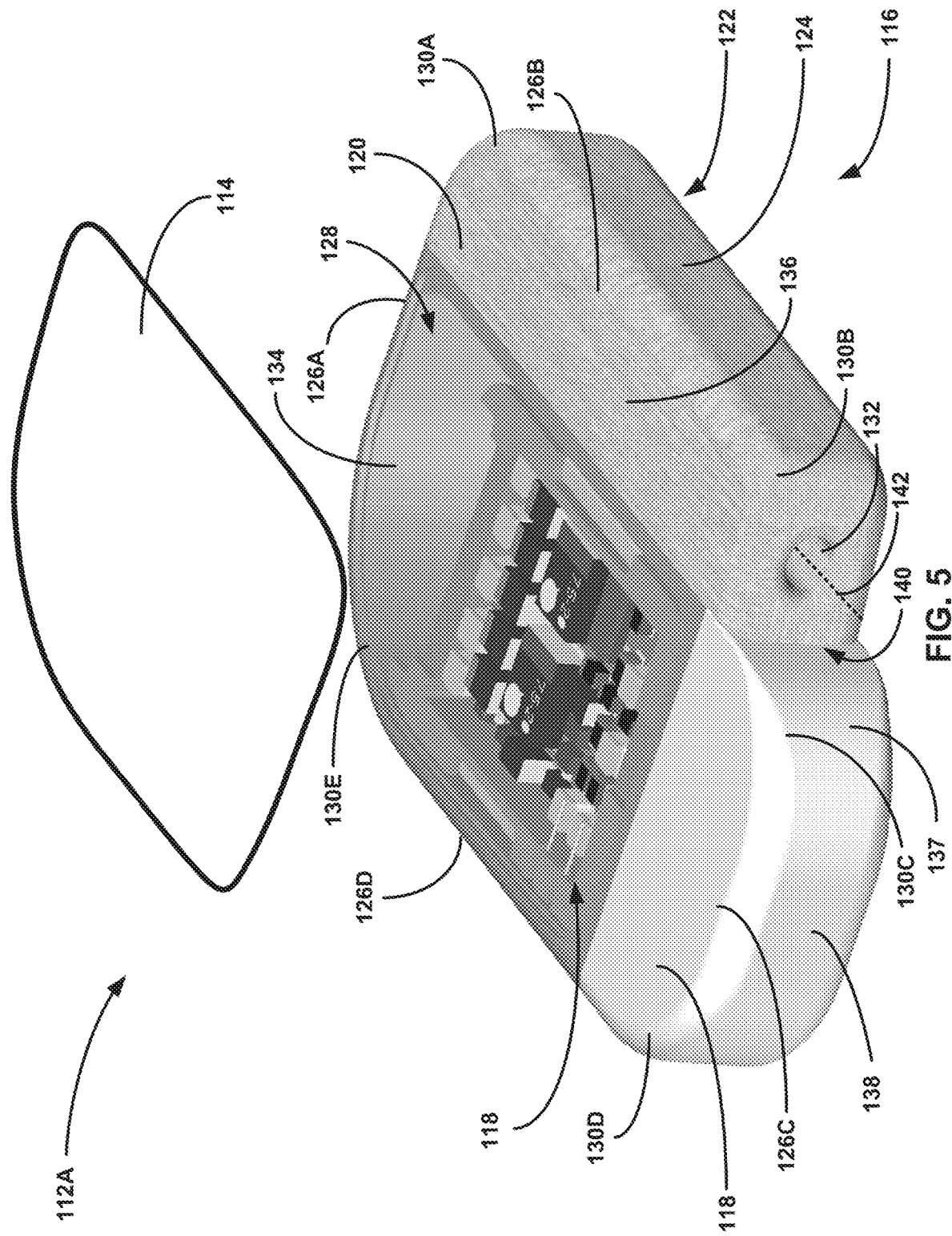
FIG. 5 is a conceptual and schematic diagram illustrating an isometric view of an example IMD with one channel for receiving a lead.

FIG. 5 is a conceptual and schematic diagram illustrating an example IMD 112A. IMD 112A may be substantially similar to IMD 12 except for any differences described herein. IMD 112A includes cover 114, housing 116, and internal components 118. IMD 112A is depicted with cover 114 of housing 116 removed from IMD 112A to depict internal components 118. Housing 116 may be configured to receive cover 114. Though cover 114 is depicted as a discrete separate piece (e.g., a titanium lid welded in place, or a glass or ceramic component such as sapphire to be secured in place), in some examples cover may be an overmold (e.g., overmolded with liquid silicone rubber) created over housing 116 to seal housing 116. In examples where cover 114 is a discrete component, housing 116 may receive cover 114 in a secure manner, such as with screws, glue, mechanical fits (e.g., an interference fit), a combination of these, or the like. Where cover 114 is a discrete component cover 114 may be removably received by housing 116, such that housing 116 may securely receive cover 114 repeatedly without notable damage to cover 114 or housing 116. Housing 116 may receive cover 114 or cover 114 may otherwise be configured to be securely attached to housing 116 such that internal components 118 are hermetically sealed within housing 116. Internal components 118 may include processing circuitry 50, stimulation circuitry 52, memory 54, telemetry circuitry 56, power source 58, sensor 60, and/or recharge coil 66 as discussed above.

Housing 116 may define a relatively flat external profile. For example, housing 116 may be approximately 3.61 centimeters long by 2.30 centimeters wide by 0.51 centimeters tall. Other dimensions are also possible.

Housing 116 may define two major surfaces 120, 122. Major surfaces 120, 122 may be substantially parallel. Major surfaces 120, 122 may define substantially similar shapes, such that outer wall 124 of housing 116 extending substantially straight between major surfaces 120, 122 is substantially perpendicular to both major surfaces 120, 122. Further, outer edges 126A-D (collectively "outer edges 126") of major surfaces 120, 122 may run substantially parallel or perpendicular to each other. By configuring housing 116 to define two substantially parallel major surfaces 120, 122 with substantially parallel or perpendicular outer edges 126 that are connected with outer wall 124 that is substantially perpendicular to major surfaces 120, 122, housing 116 may define a generally cuboid (e.g., substantially orthogonal) main cavity 128. Housing 116 may receive some, most, or all internal components 118 in main cavity 128. In some example, housing 116 may receive substantially all of processing circuitry 50, stimulation circuitry 52, and telemetry circuitry 56 in main cavity 128. In some examples, internal components 118 may themselves be generally cuboid in shape, such that configuring housing 116 to define a cuboid main cavity 128 may enable housing 116 to receive internal components 118 in a relatively volumetrically efficient fashion.

Major surfaces 120, 122 of housing 116 may define a plurality of corners 130A-E (collectively "corners 130"). Corners 130 may be substantially rounded, such that adjacent outer edges 126 generally do not meet at a right angle even where they run substantially perpendicular to each other. Configuring corners 130 to be substantially rounded may promote the comfort of IMD 112A and reduce a chance of housing 116 catching, tearing, or otherwise damaging tissue surrounding IMD 112A following implantation of IMD 112A (e.g., as a result of a theoretical sharp/right angle corner/acute corner).

IMD 112A may define channel 132 for coupling lead 14 to IMD 112A. Channel 132 may be a substantially straight bore or hole that extends into housing 116. Channel 132 may be substantially parallel major surfaces 120, 122. In some examples, channel 132 may be substantially parallel with one or more outer edges 126. For example, as depicted in FIG. 5, channel 132 is substantially parallel with outer edge 126B and 126D. In other examples, housing 116 may define a substantially circular cross-section, such that channel 132 is not substantially parallel with an outer edge of housing 116. In some examples, a coil may coil around channel 132. The coil may be an antenna that is part of telemetry circuitry 56 or recharge coil 66 for power source 58.

Channel 132 may be configured to receive lead 14. Channel 132 may be configured to receive lead 14 such that lead 14 is electrically coupled to internal components 118 within IMD 112A in response to channel 132 receiving lead 14. Channel 132 may electrically couple lead 14 to internal components 118 as a result of one or more connectors that contact and electrically couple to terminal connection points of lead 14 once lead 14 is fully received by channel 132 (e.g., once lead 14 has been pushed into the full depth of channel 132). IMD 112A may include a separate connector for each electrode of lead 14. It is to be understood that IMD 112A may include any number of spatial configurations of connectors that electrically couple internal components 118 to lead 14 depending upon, e.g., the proximal terminal of lead 14 and the number of electrodes of lead 14. In some examples, a diameter of channel 132 along outer wall 124 may be greater than a diameter of channel 132 within housing 116 as a result of a taper facilitating the reception of lead 14 by channel 132. An angle of a taper of channel 132 relative to the inner and outer diameter of channel 132 may be fixed or varied.

In some examples, lead 14 may be secured to IMD 112A as a result of lead 14 being inserted to a full depth within channel 132. In other examples, IMD 112A may include one or more securing features that are configured to secure lead 14 within channel 132. For example, housing 116 may define one or more securing bores that extend from an outer surface of housing 116 at least partially into channel 132. Securing bores may be configured to receive one or more securing elements that are configured to secure lead 14 within channel 132. For example, a surface of securing bores may define threads and a securing element may include a bolt, such that the bolt may be threaded into the securing bore and engage lead 14 to hold lead 14 within channel 132. In other examples, the securing element may be an adhesive that is configured to be injected or inserted into the securing bore and adhere lead 14 to channel 132 once channel 132 receives lead 14. Other examples of securing bores and securing elements are also possible.

Housing 116 may be a single unitary component or housing 116 may be a plurality of components that are securely connected. For example, housing 116 may include main chassis 134, connector header 136, and battery compartment 138. Connector header 136 may define channel 132 and battery compartment 138 may be configured to house power source 58 as discussed herein. For example, battery compartment 138 may include power source 58 D-shaped lithium ion battery. In some examples, battery compartment 138 may substantially be power source 58 with an overmold configured to be secured to chassis 134 and connector header 136. In some examples, connector header 136 and/or battery compartment 138 may be titanium components that are welded to chassis 134, though in other examples connector header 136 and/or battery compartment 138 may be plastic components that are configured to be mechanically secured attached (e.g., glued, chemically bonded, received with interlocking parts, received with an interference fit) to chassis 134.

Connector header 136 and battery compartment 138 may be configured to be securely attachable to chassis 134. For example, corners 130C, 130D of battery compartment 138 may be rounded to an extent that creates a gap that provides weldable interface 140 between battery compartment 138 and connector header 136. Put differently, rounded corner 130C nearest connector header 136 may extend up to chassis 134 at an acute angle, such that battery compartment 138 does not substantially contact connector header 136, enabling a weld between connector header 136 and battery compartments 138. The weld may be a triple point weld with high weld overlap. Welding the battery compartment 138 to the connector header 136 with a triple point weld with high weld overlap may reduce the chance of pinholes forming in the housing 116 and therein impairing or destroying a hermetic seal of the IMD 112A.

In some examples, when securely connected to chassis 134 and connector header 136, battery compartment 138 may extend out from chassis 134 adjacent to a mouth of channel 132, therein creating a "shoulder" next to the mouth of channel 132. The shoulder of battery compartment 138 may extend from chassis 134 in a direction that is substantially parallel to axis 142 of channel 132. Battery compartment 138 may extend from chassis 134 at least a distance that is sufficient to enable lead 14 extending from channel 132 to flex up and out of a potential recess 28 in cranium 20 in which IMD 112A is located without straining lead 14.

This shoulder may define funneling wall 137. Funneling wall 137 may be an outer surface of IMD 112A that provides a substantially smooth and rounded transition from a surface that is removed from the mouth of channel 132 to a surface that defines this mouth. Lead 14 extending out of channel 132 may contact funneling wall 137 as lead 14 extends away from channel 132. Funneling wall 137 may define a radius that reduces or eliminates the possibility of lead 14 kinking if lead 14 contacts the funneling wall shoulder substantially continuously as lead 14 extends away from the mouth of channel 132. In this way, upon implantation of IMD 112A, a clinician may wrap lead 14 around funneling wall 137 to promote the integrity of lead 14.

FIG. 6 is a conceptual and schematic side view of IMD 112A. FIG. 6 depicts outer diameter 150 and inner diameter 152 of channel 132 as discussed above. The depicted size of outer diameter 150 and inner diameter 152 are for purposes of illustration only; in other examples, IMD 112A may include different relative diameters to accommodate different leads 14 and create different tapers.

In some examples, channel 132 may be substantially centered between major surfaces 120, 122 of IMD 112A as depicted. In other examples, channel 132 may be relatively closer to one major surface 120, 122 compared to the other major surface 122, 120. For example, if major surface 120 is to be located contacting cranium 20 and a planned recess 28 in cranium 20 is relatively deep, channel 132 may be relatively closer to major surface 122 to enable lead 14 to extend from channel 132 and flex out of recess 28 to avoid straining lead 14.

FIG. 7 is a conceptual and schematic top view of IMD 112A as received by recess 160 of cranium 20. Recess 160 may be substantially similar to recess 28 as described herein. As depicted, recess 160 may be generally rectangular, even when housing 116 of IMD 112A is not substantially rectangular. As depicted, IMD 112A is located in recess 160 with major surface 122 "up" (relatively further away from cranium 20) and major surface 120 contacting or directly adjacent cranium 20 within recess 160. In some examples, IMD 112A is flippable within recess 160, such that IMD 112A operates in substantially the same way with either major surface 120 or major surface 122 closer to cranium 20. In this way, a clinician may orient/flip IMD 112A as desired to orient channel 132 in a desired direction. In other examples, IMD 112A is configured to operate with only one of the two major surfaces 120, 122 relatively closer to cranium 20. For example, housing 116 of IMD 112A may include fixtures through which screws may be inserted and therein screwed into cranium 20. These fixtures (not depicted) may extend from one of the two major surfaces 120, 122, such that the respective major surface 120, 122 that includes the fixtures must be placed "face-down" contacting cranium 20 in order for these fixtures to be used.

FIG. 7 also depicts length 170 which battery compartment 138 extends past mouth 172 of channel 132. Is it to be understood that length 170 of FIG. 7 is for purposes of illustration only, as in other examples length 170 can be greater or smaller. In some examples, length 170 can be a function of a depth of recess 160 and/or a spacing of channel 132 between major surfaces 120, 122 of IMD 112A.

Figure 8:
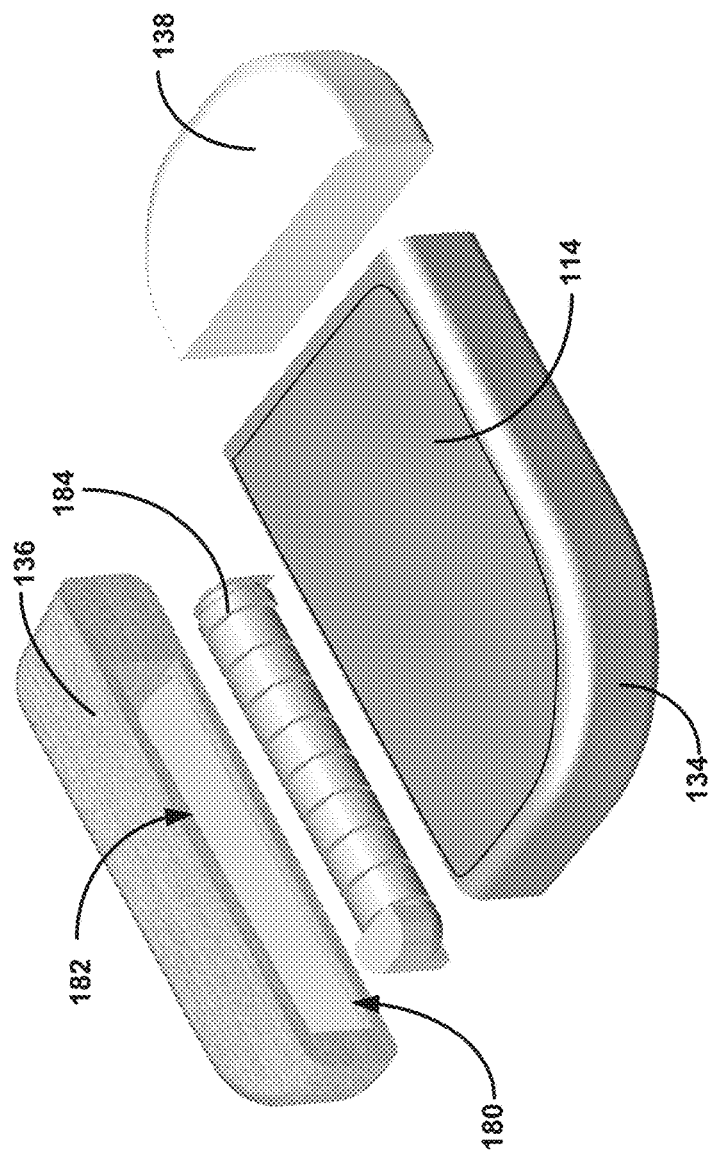
FIGS. 8 and 9 are conceptual and schematic diagrams illustrating an exploded view of the IMD of FIG. 5 and a view of the main chassis of FIG. 5, respectively.

FIG. 8 is a conceptual and schematic exploded view of IMD 112A, with connector header 136 and battery compartment 138 spaced apart from chassis 134. As depicted in FIG. 8, chassis 134 has received cover 114. As noted above, in some examples, cover 114 may not be a discrete component of housing 116, but instead cover 114 may be a part of an overmold that covers some or all of housing 116.

Connector header 136 defines cavity 180 as seen through window 182. Cavity 180 of connector header 136 may receive some internal components 118. For example, cavity 180 may receive a telemetry coil of telemetry circuit 78 and/or recharge coil 66. It is to be understood that the specific size and configuration of cavity 180 is for purposes of illustration only, as IMD 112A may be of various sizes to receive include coils of many sizes and configurations.

Cavity 180 may further receive connector stack 184 that includes electrical contacts and isolation seals. Connector stack 184 may be configured to electrically couple to lead 14 once lead 14 is received by channel 132. Connector stack 184 may include a plurality of electrically conductive elements that are each separated from adjacent electrically conductive elements by one of a plurality of electrically insulative elements, such that the electrically conductive elements and electrically insulative elements are at least partially "stacked" along a longitudinal axis of connector stack 184. Connector stack 184 may electrically couple lead 14 to internal components 118 of IMD 112A.

When connector header 136 is securely attached to chassis 134, window 182 of connector header 136 may align with one or more complementary windows of chassis. When received by channel 132, connector stack 184 may electrically couple lead 14 with internal components 118 of IMD through window 182 of connector header 136 and one or more windows of chassis. For example, lead 14 may be electrically coupled with internal components 118 via elongated conductors of connector stack 184 that contact lead 14 and contact internal components 118 within housing 116. Internal components 118 of housing 116 may be located on a printed circuit board (PCB), and elongated conductors may electrically couple lead 14 to this PCB.

Figure 9:
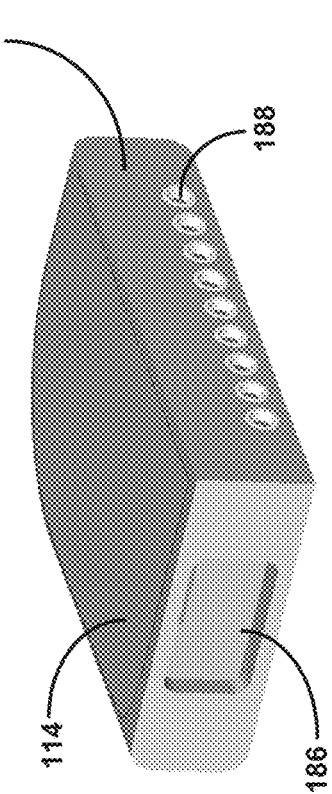

Similarly, though FIG. 8 depicts battery compartment 138 as solid for purposes of illustration, battery compartment 138 may contain power source 58 as described herein. Power source 58 may be electrically coupled to and therein provide power to internal components 118 of IMD 112A through a complementary window of chassis 134. For example, FIG. 9 is a conceptual and schematic view of chassis 134 that includes both an example window 186 through which power source 58 of battery compartment 138 electrically couples to internal components 118 of IMD 112A. Further, FIG. 9 depicts a plurality of windows 188 through which connector stack 184 electrically couples lead 14 to internal components 118 of IMD 112A as described above. The shape and number of location of windows 186, 188 is purely for purposes of illustration only, as a different number of windows 186 188 of different shapes and in different locations are also possible.

FIGS. 10-12 are conceptual and schematic top, front, and side views, respectively, of example IMD 112B. IMD 112B may be substantially similar to IMD 112A with the exception of any differences described herein. IMD 112B defines two channels 190A, 190B in two connector headers 192A, 192B of IMD 112B. IMD 112B may be substantially mirrored across central plane 194 of IMD 112B.

As a result of having two channels 190A, 190B, IMD 112B may be configured to simultaneously provide therapy to and/or monitor patient 18 through two separate leads 14. In some examples, as a result of utilizing two leads 14 received by IMD 112B through two channels 190A, 190B, more (or otherwise different) internal components 118 may be necessary. For example, power source 58 may need relatively more power to supply a sufficient amount of power to both leads 14 within both channels 190A, 190B. Similarly, stimulation circuitry 52 may need to be more robust to provide potentially different electrical signals to both leads 14. However, some internal components 118 of IMD 112B may be substantially similar to respective internal components 118 of IMD 112A. For example, IMD 112B may include sensor 60 to detect heat of IMD 112B, and sensor 60 of IMD 112B may be substantially similar to sensor 60 of IMD 112A.

FIGS. 13 and 14 are conceptual and schematic diagrams illustrating an isometric and front view of an example IMD 212A. IMD 212A may be substantially similar to IMD 12 and 112A except for any differences described herein. IMD 212A includes housing 216 and internal components (not depicted). Internal components of IMD 212A may include processing circuitry 50, stimulation circuitry 52, memory 54, telemetry circuitry 56, sensor 60, and/or recharge coil 66 as discussed above. Housing 216 may be hermetically sealed.

In some examples, housing 216 may be a single unitary structure. In other examples, housing 216 may include two or more separate structures. For example, housing 216 may include main chassis 134, connector header 136, and battery compartment 238, each of which are a separate structure. Chassis 234, connector header 236, and battery compartment 238 may be secured together into housing 216 (e.g., welded or glued or mechanically fastened).

Chassis 234, connector header 236, and battery compartment 238 may be generally flat compartments, such that each substantially defines a flat plane. Further, when assembled together into housing 216, chassis 234 and battery compartment 238 may be centered along first plane 220 and connector header 236 may be centered along second plane 222, where second plane 222 is at angle 242 to first plane 220. Angle 242 may approximate curvature of cranium 20 at the implantation site. As depicted, chassis 234 and connector header 236 may further define top major surface 221 and bottom surface 223, where bottom major surface 223 is configured to contact cranium 20 when IMD 212A is secured to the patient. Top major surface 221 and bottom major surface 223 may be generally parallel with each other and may both define angle 242, such that both top major surface 221 and bottom major surface 223 approximate a curvature of cranium 20 of patient. By configuring connector header 236 to assemble/attach to chassis 234 and/or battery compartment 238 at angle 242 such that bottom surface 223 approximates the curvature of cranium 20, IMD 212A may be better suited to sit flush against cranium 20 without a possibility for "rocking" back and forth. It is to be understood that the depicted angle 242 is for purposes of illustration, and relatively greater or smaller angles can be used in other examples.

Connector header 236 may attach to chassis 234 and/or battery compartment 238 along a single edge 214. In some examples, edge 214 is substantially perpendicular to second plane 222, such that connector header 236 is substantially entirely centered along second plane 222 (while battery compartment 238 and/or chassis 234 are only centered along first plane 220 for a portion of battery compartment 238 and/or chassis 234). In other examples, edge 214 is substantially perpendicular to first plane 220, such that battery compartment 238 and chassis are substantially entirely centered along first plane 220. In yet other examples, edge 214 is substantially perpendicular to neither first plane 220 nor second plane 222, such that none of connector header 236, chassis 234, or battery compartment 238 are centered on second plane 222 or first plane 220, respectively, along the junction between connector header 238, chassis 234, and battery compartment 238.

Chassis 234 of housing 216 may define a main cavity (not depicted) to receive internal components of IMD 212A. In some examples, the main cavity of chassis 234 may store most internal components of IMD 212A. The main cavity of chassis 234 may be substantially cuboid in shape. Configuring chassis 234 to define a substantially cuboid main cavity may enable chassis 234 to receive internal components 218 in a relatively volumetrically efficient fashion (e.g., as most internal components 218 may be themselves substantially cuboid in shape). Similarly, battery compartment 238 may include or receive power source 58. Power source 58 may be a D-shaped lithium ion battery.

Housing 216 may define a plurality of corners 230A-E (collectively "corners 230"). Corners 230 may be substantially rounded, such that adjacent outer walls generally do not meet at a right angle (e.g., even where these adjacent outer walls run substantially perpendicular to each other). Configuring corners 230 to be substantially rounded may promote the comfort of IMD 212A and reduce chances of housing 216 catching, tearing, or otherwise damaging surrounded tissue following implantation of IMD 212A (e.g., as a result of a theoretical sharp/right angle corner/acute corner).

IMD 212A may include channel 232 for coupling lead 14 to IMD 212A. Channel 232 may be a substantially straight hole or bore that extends into housing 216. Axis 244 of channel 232 may be substantially parallel with second plane 222. In some examples, an antenna that is part of telemetry circuitry 56 and/or recharge coil 66 may coil around longitudinal axis 244 of channel 232 within connector header 236.

Channel 232 may be configured to receive lead 14. Channel 232 may be configured to receive lead 14 such that IMD 212A immediately electrically couples internal components of IMD 212A with lead 14 in response to channel 232 receiving lead 14. In some examples, channel 232 may taper from an outer diameter to an internal diameter similar to channel 232. The taper may facilitate the act of inserting lead 14 into channel 232. An angle of a taper of channel 232 relative to the inner and outer diameter of channel 232 may be fixed or varied. Further, similar to IMD 112A as described above, IMD 212A may define one or more securing bores and may include one or more securing elements configured to secure lead 14 within channel 232 once lead 14 is received by channel 232.

Connector header 236 and battery compartment 238 may be configured to be securely attachable to chassis 234. For example, corner 230D of battery compartment 238 may be rounded to an extent that creates a gap that provides weldable interface 240 between battery compartment 238 and connector header 236. Put differently, rounded corner 230D nearest connector header 236 may extend up to chassis 234 at an acute angle, such that battery compartment 238 defines a gap (e.g., battery compartment 238 is not flush) with connector header 236, enabling a weld between connector header 236 and battery compartment 238. The weld may be a triple point weld with high weld overlap. Welding the battery compartment 238 to the connector header 236 with a triple point weld with high weld overlap may reduce the chance of pinholes forming in the housing 216 and therein impairing or destroying a hermetic seal of the IMD 212A.

Similar to IMD 112A above, corner 230D may provide a shoulder that defines funneling wall 237. Funneling wall 237 may be a surface of shoulder that provides a substantially smooth and rounded transition from a surface that is removed from the mouth of channel 232 to a surface that defines this mouth. Lead 14 extending out of channel 232 may contact this funneling wall 237 as lead extends away from channel 232. Funneling wall 237 may define a radius that reduces or eliminates the possibility of lead 14 kinking if lead 14 contacts funneling wall 237 substantially continuously as lead 14 extends away from the mouth of channel 232. In this way, upon implantation of IMD 212A, a clinician may wrap lead 14 around funneling wall 237 to promote the integrity of lead 14.

In some examples, when securely connected to chassis 234 and connector header 236, battery compartment 238 may extend out from chassis 234 adjacent to a mouth of channel 232. Battery compartment 238 may extend from chassis 234 in a direction that is substantially parallel to longitudinal axis 144 of channel 232. Battery compartment 238 may extend from chassis 234 at least a distance that is sufficient to enable lead 14 extending from channel 232 to flex up and out of a potential recess 28 in cranium 20 in which IMD 212A is located.

Figure 15:
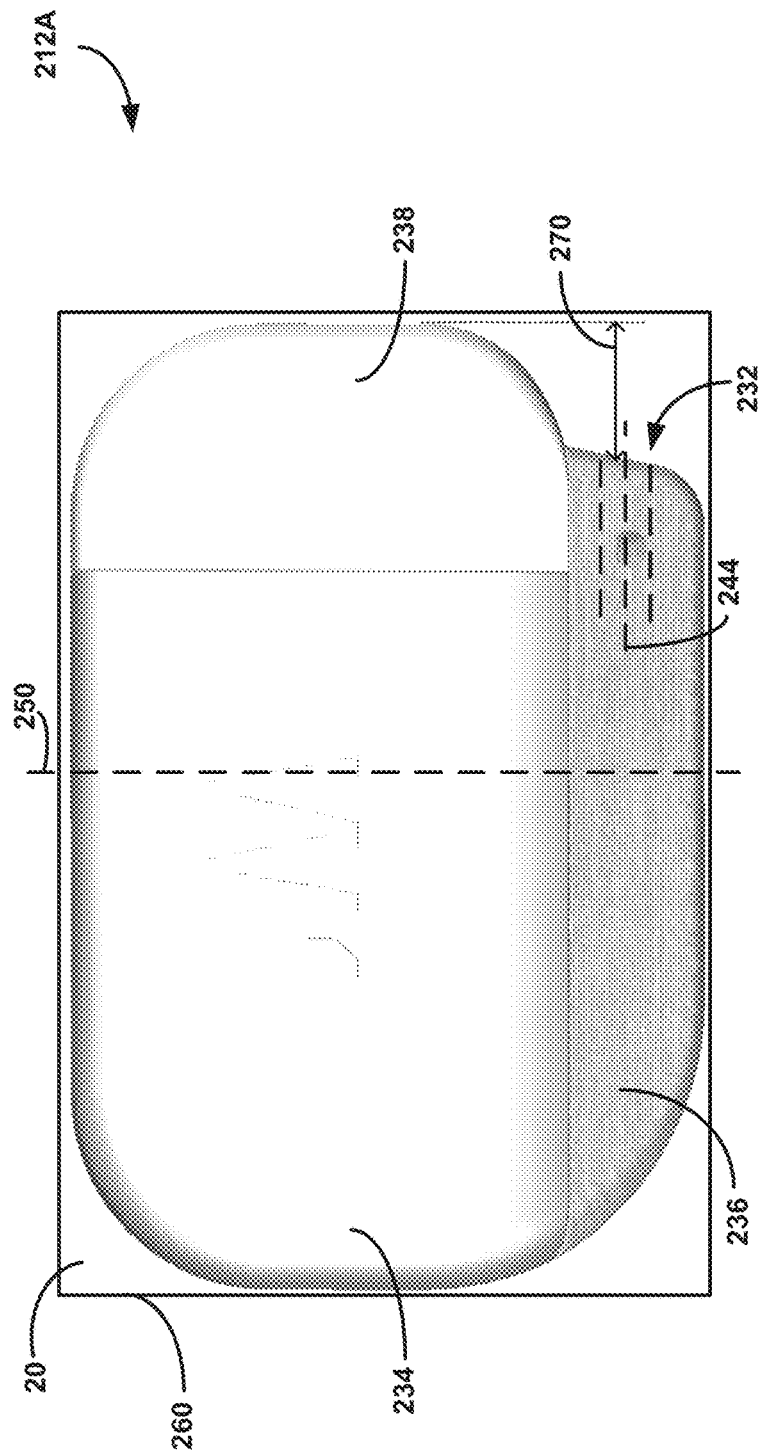
FIGS. 15 and 16 are conceptual and schematic diagrams illustrating a top and cross-sectional view, respectively, of the IMD of FIGS. 13 and 14.

FIG. 15 is a conceptual and schematic top view of IMD 212A as received by recess 260 of cranium 20. Recess 260 may be substantially similar to recess 28 and 160 as described herein. As depicted, recess 260 may be generally rectangular, even when housing 216 of IMD 212A is not substantially rectangular. Further, a curvature of recess 260 may match a curvature of cranium 20. Put differently, in creating recess 260, a clinician may carve out an amount of cranium 20 without working to flattening recess 260, such that recess 260 is substantially a depressed portion of cranium 20.

As depicted, a clinician may place IMD 212A in recess 260. A clinician may place IMD 212A in recess 260 such that the curvature of IMD 212A (e.g., as a result of relative angle between connector header 236 and chassis 234/battery compartment 238) aligns with the curvature of cranium 20 and recess 260. Once placed in recess 260, a clinician may fasten IMD 212A to cranium 20. For example, housing 216 of IMD 212A may include fixtures through which screws may be inserted and therein screwed into cranium 20. These fixtures (not depicted) may extend from surface(s) of housing 216 that are configured to contact cranium 20 (e.g., a "bottom" surface of housing 216 that is nearest to cranium 20

FIG. 15 also depicts length 270 which battery compartment 238 extends past a mouth of channel 132. Length 270 may be measured along longitudinal axis 244 of channel 232. Is it to be understood that length 270 of FIG. 15 is for purposes of illustration only, as in other examples length 270 can be greater or smaller. In some examples, length 270 can be a function of a depth of recess 260 and/or a location of channel 232 within connector header 236 (e.g., whether channel 232 is relatively close or far from cranium 20 within connector header 236 when IMD 212A is placed in recess 260.

FIG. 15 also depicts cross-sectional cut-plane 250. Cross-sectional cut-plane 250 may be substantially perpendicular to first plane 220 and second plane 222. Cross-sectional cut-plane 250 may generally bisect IMD 212A.

Figure 16:
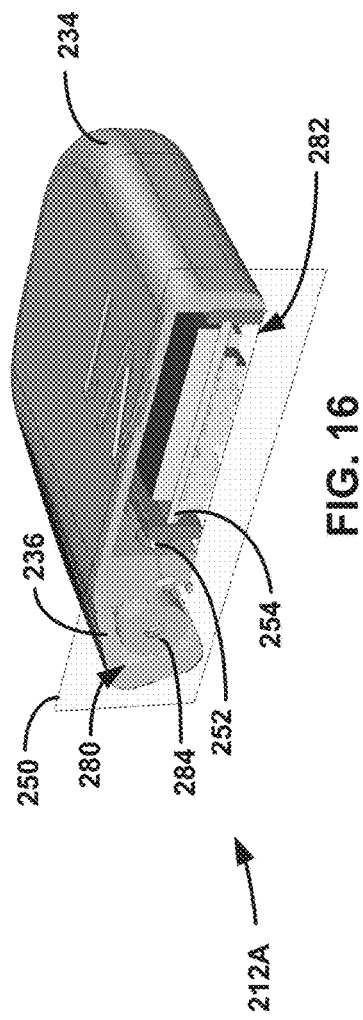

FIG. 16 is a conceptual and schematic cross-sectional view of IMD 212A taken along cross-sectional cut plane 250. Connector header 236 defines cavity 280. Cavity 280 of connector header 236 may receive some internal components of IMD 212A. For example, cavity 280 includes coil 284. Coil 284 may be an antenna of telemetry circuit 78 and/or coil 284 may be recharge coil 66.

When connector header 236 is securely attached to chassis 234, one or more windows of connector header 236 (e.g., one or more windows similar to window 182 of connector header 136) may align with one or more complementary windows of chassis 234 (e.g., complementary windows similar to windows 188 of chassis 134). When received by channel 232, lead 14 may be electrically coupled to internal components of IMD through one or more windows of connector header 236 and chassis 234. For example, one or more integrated connectors 252 may extend through windows to electrically couple lead 14 to a PCB 254 within housing 216. Similarly, though not depicted, power source 58 of battery compartment 238 may electrically couple and provide power to internal components of IMD 212A through a complementary window of chassis 234 (e.g., complementary windows similar to windows 186 of chassis 134).

FIGS. 17 and 18 are conceptual and schematic isometric and front views, respectively, of example IMD 212B. IMD 212B may be substantially similar to IMD 212A with the exception of any differences described herein. IMD 212B defines two channels 290A, 290B (collectively "channels 290") in two connector headers 292A, 292B (collectively "connector headers 292") of IMD 212B. IMD 212B may be substantially mirrored across central plane 294 of IMD 212B. Similar to IMD 212A, battery compartment 276, chassis 274, and connector headers 292 of IMD 212B may be generally flat. Further battery compartment 276 and chassis 274 may be generally aligned (e.g., parallel) with first plane 278, while connector header 292A is generally aligned (e.g., parallel) with second plane 286, and connector header 292B is generally aligned (e.g., parallel) with third plane 288. In some examples (not depicted), either second plane 286 or third plane 288 is generally parallel with first plane 278. In other examples, neither second plane 286 nor third plane 288 may be parallel with first plane 278. Instead, second plane 286 may be at angle 296 with first plane 278 while third plane 288 is at angle 298 with first plane 278. In some examples, angle 296 and angle 298 may be substantially similar, while in other examples angle 296 and angle 298 may be different. By configuring connector headers 292 to be IMD 212B to be at two different or substantially similar angles 296, 298 with chassis 274, and battery compartment 276, IMD 212B may be able to generally align with the curvature of cranium 20.

As a result of having two channels 290, IMD 212B may be configured to simultaneously provide therapy to and/or monitor patient 18 through two separate leads 14. In some examples, as a result of utilizing two leads 14 received by IMD 212B through two connector headers 292, more (or otherwise different) internal components 118 may be necessary. For example, power source 58 may need relatively power to supply a sufficient amount of power to separate leads 14 within both connector headers 292. Similarly, stimulation circuitry 52 of IMD 212B may need to be more robust to provide potentially different electrical signals to both leads 14. However, some internal components of IMD 212B may be substantially similar to respective internal components of IMD 212A. For example, IMD 212B may include a coil that serves as an antenna for telemetry circuitry 56, and this coil may be substantially similar to coil 284 of IMD 212A.

FIGS. 19 and 20 are conceptual and schematic diagrams illustrating an isometric and front view, respectively, of an example IMD 312A. IMD 312A may be substantially similar to IMD 12, IMD 112A, and IMD 212A except for any differences described herein. IMD 312A includes cover 314, housing 316, and internal components 318. IMD 312A is depicted with cover 314 of housing 316 removed from IMD 312A to depict some internal components 318. Though cover 314 is depicted as a discrete separate piece, in some examples cover 314 may be an overmold created over housing 316 to seal housing 316 (e.g., similar to cover 114 of IMD 112A). In examples where cover 114 is a discrete component, housing 316 may be configured to receive cover 314. Housing 316 may receive cover 314 in a secure manner, such as with screws, glue, mechanical fits (e.g., an interference fit), a combination of these, or the like. Cover 314 may be removably received by housing 316, such that housing 316 may securely receive cover 314 repeatedly without notable damage to cover 314 or housing 316. Housing 316 may receive cover 314 such that internal components 318 are hermetically sealed within housing 316. Internal components 318 may include processing circuitry 50, stimulation circuitry 52, memory 54, telemetry circuitry 56, sensor 60, and/or recharge coil 66 as discussed herein.

Housing 316 may be generally mirrored across central plane 328 extending through the middle of housing 316 as viewed from the front of housing 316 (e.g., where the front of housing 316 is the side of housing 316 which receives lead 14). Housing 316 may define two major surfaces, top major surface 320 and bottom major surface 322. Both top major surface 320 and bottom major surface 322 may be substantially curved. In some examples, both surfaces 320, 322 define generally parabolic curves. Top major surface 320 and bottom major surface 322 may define generally similar curves, such that both top major surface 320 and bottom major surface 322 curve in a similar direction relative to a fixed point. Put differently, both top major surface 320 and bottom major surface 322 may arc in a substantially similar direction along a substantially shared axis 310. The shared axis 310 may be on the central plane 328. For example, housing 316 may define a shape that is approximately 4.5 centimeters long by 3.175 centimeters wide and between 0.5 and 0.7 centimeters high.

Bottom major surface 322 may be configured to generally align with curvature of cranium 20 and therein be secured to cranium (e.g., secured within recess 28). Top major surface 320 may extend/dome away from bottom major surface 322 (e.g., by virtue of a more pronounced curve of top major surface 320) to create one or more internal cavities to house internal components 318. Put differently, bottom major surface 322 may be a slightly curved surface from left to right (as viewed from a front side of IMD 312A which contains a channel to receive lead 14) from which top major surface 320 further curves away, such that top major surface 320 approximates a dome extending away from bottom major surface 322. In some examples, top major surface 320 and/or bottom major surface 322 may not be a singular surface, but instead a plurality of curved or flat surfaces that collectively approximate the curves described herein.

In certain examples, top and bottom surfaces 320, 322 may meet at opposing side edges 324A, 324B (collectively, "side edges 324") of housing 316 and/or front and back edges 326A of housing 316, 326B (collectively, "front and back edges 326"), where a front of IMD 312A is the side of IMD 312A which lead 14 connects to. Side edges 324 may extend substantially parallel to each other. Similarly, front and back edges 326 may extend substantially parallel to each other. In some examples, top and bottom surfaces 320, 322 may define more or less than four edges, such that top or bottom surfaces 320, 322 generally define circular shapes, hexagonal shapes, or the like. In other examples (not depicted), top major surface 320 and bottom major surface 322 may not contact each other, but may instead by connected to one or more intermediate sidewalls of housing 316. By configuring housing 316 to define a unitary structure that domes away from cranium 20, IMD 312A may define a low and smooth profile that may reduce a chance of irritation or damage to nearby tissue of patient 18.

Housing 316 may define a plurality of corners 330A-B (collectively "corners 330"). Corners 330 may be substantially rounded, such that adjacent outer edges generally do not meet at a right angle even where these adjacent outer edges run substantially perpendicular to each other. Configuring corners 330 to be substantially rounded may promote the comfort of IMD 312A and reduce chances of housing 316 catching, tearing, or otherwise damaging surrounded tissue following implantation of IMD 312A (e.g., as a result of a theoretical sharp/right angle corner/acute corner).

IMD 312A may include channel 332 for coupling lead 14 to IMD 312A. Channel 332 may be a substantially straight bore or hole that extends into housing 316. A mouth of channel 332 may taper as described herein. Channel 332 may be centered along central plane 328. In some examples, channel 332 is closer to top major surface 320 of housing 316 than bottom major surface 322. Positioning channel 332 relatively closer to top major surface 320 may improve an ability of lead 14 to extend out from IMD 312A (when received by IMD 312A) without contacting cranium 20 when IMD 312A is secured to cranium 20. Channel 332 may be substantially parallel with side edges 324 of housing 316. In response to a clinician inserting lead 14 into channel 332, one or more proximal terminals of lead 14 may contact and therein be electrically coupled to a respective number of connectors 336 within IMD. Connectors 336 may send electric signals to and receive electric signals from lead 14. Connectors 336 may extend along a plane that is generally tangential relative to channel 332. Angling connectors 336 in a tangential (rather than radial) direction relative to channel 332 may enable a more pronounced curve of top major surface 320 as discussed herein, therein reducing the profile of housing 316 of IMD 312A. Further, similar to IMD 112A and IMD 212A as described above, IMD 312A may define one or more securing bores that extend into channel 332 and may include one or more securing elements configured to secure lead 14 within channel 332 once lead 14 is received by channel 332.

In some examples, coil 334 that is part of telemetry circuitry 56 and/or recharge coil 66 may wrap around channel 332 within housing 316. Housing 316 may have a non-metallic portion surrounding coil 334 to allow for the uninhibited transmission of signals to and from coil 334. In some examples, IMD 312A may not include cover 312 to enable the transmission of signals to and from coil 334.

In some examples, housing 316 may generally define two internal cavities on either side of channel 332. One side (e.g., the side to which the one or more connectors 336 are extending) may include circuits and/or sensors as described herein, while the other side may include power source 58. Circuits and/or sensors may be mounted (e.g., punched through, mechanically attached to, bonded to, or the like) on one or more rigid-flex PCB. A rigid-flex "hybrid" PCB may include a circuit board with one or more rigid boards that are each substantially rigid (e.g., unbendable) that are securely attached to one or more flexible strips or layers that are each substantially flexible (e.g., bendable along one or more axis), wherein electrical components are secured to or within or on both the one or more rigid boards and the one or more flexible strips. Using a rigid-flex "hybrid" PCB may enable circuits and/or sensors to flex according to the curvature of housing 316. Power source 58 may provide power to rigid-flex PCB in the other cavity through a connection between channel 332 and bottom major surface 322.

Figure 21:
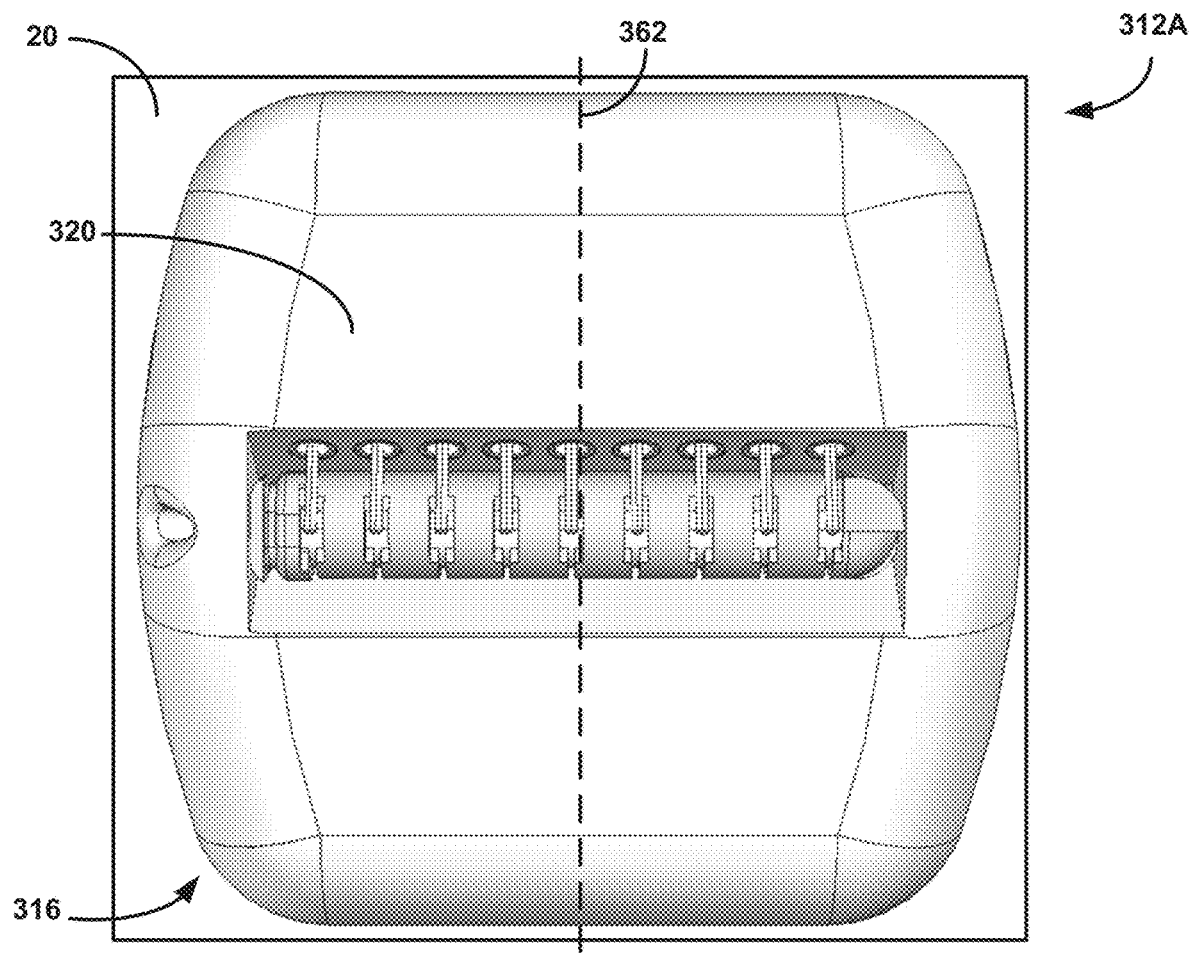
FIGS. 21 and 22 are conceptual and schematic diagrams illustrating a top and cross-sectional view, respectively, of the IMD of FIGS. 19 and 20.

FIG. 21 is a conceptual and schematic top view of IMD 312A as secured to cranium 20. Though not depicted, in some examples IMD 312A may be received within a recess 28 as described herein. However, as a result of the relatively small profile of IMD 312A, it may be unnecessary to place IMD 312A within recess 28. As depicted, IMD 312A is secured to cranium 20 with top major surface 320 "up" (relatively further away from cranium 20) and bottom major surface 322 contacting cranium 20. In some examples, housing 316 of MD 312A may include fixtures through which screws may be inserted and therein screwed into cranium 20. These fixtures (not depicted) may extend out from housing 316 at a location where the fixtures are relatively unlikely to inhibit location of lead 14 (e.g., fixtures may be located relatively removed from channel 332).

Figure 22:
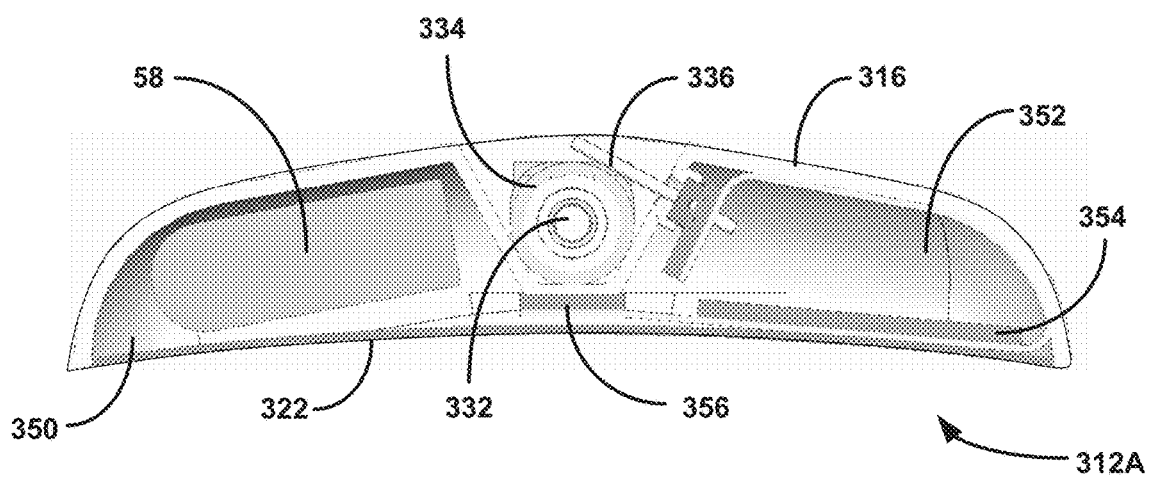

FIG. 22 is a conceptual and schematic cross-sectional front view of IMD 312A from cross sectional plane 362. Housing 316 defines first cavity 350 on one side of channel 332 and second cavity 352 on other side of channel 332. First cavity 350 may receive power source 58, while second cavity 352 stores hybrid PCB 354 and assorted internal components 318. For example, second cavity 352 may receive substantially all of processing circuitry 50, stimulation circuitry 52, and telemetry circuitry 56. Internal components 318 may receive power from power source 58 via a connection 356 that extends from first cavity 350 to second cavity 352 between coil 334 and bottom major surface 322. The depicted placement and curvature of hybrid PCB 354 within FIG. 22 is for purposes of illustration only, it is to be understood that hybrid PCB 354 may curve in other manners or be arranged within second cavity 352 in other configurations in other examples.

Figure 23:
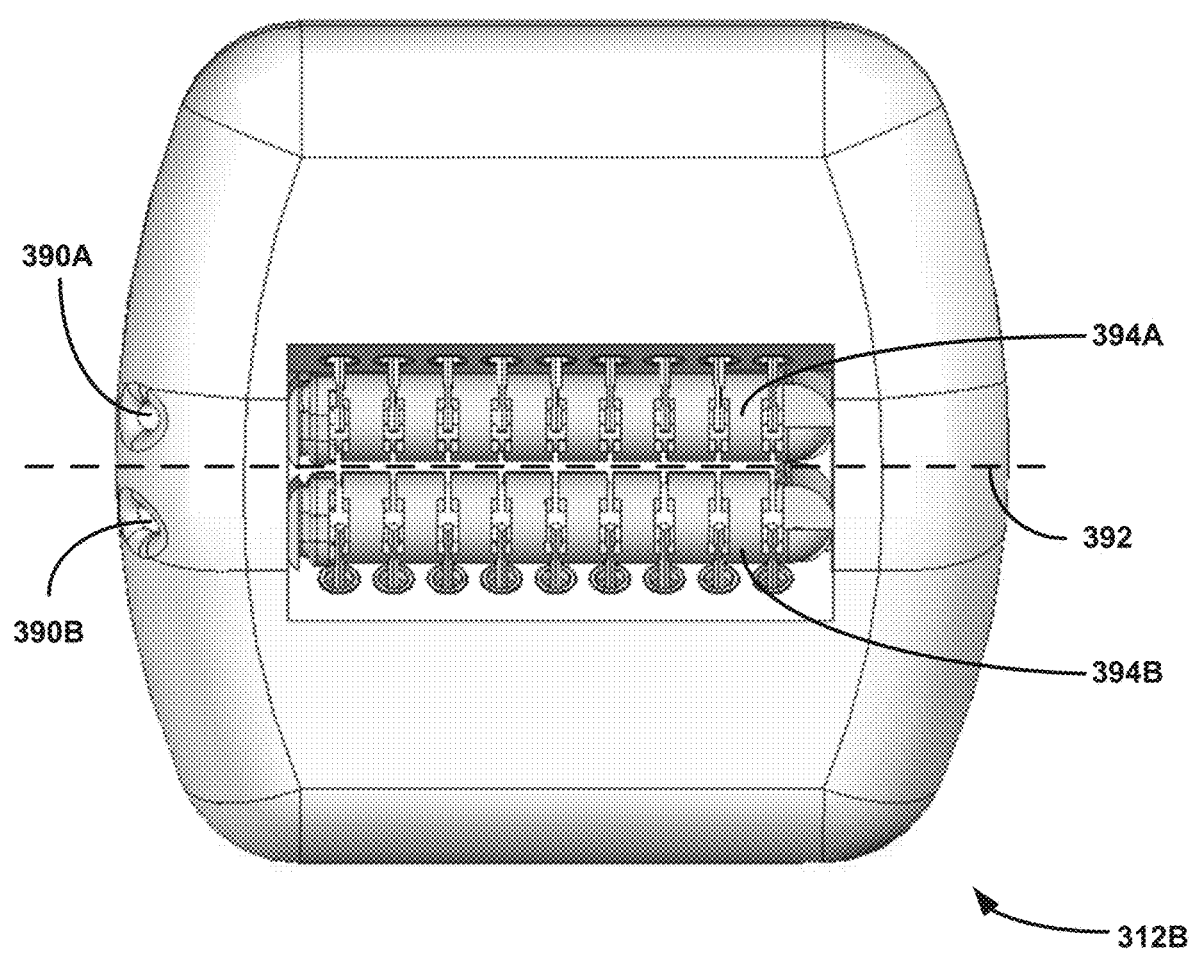
FIGS. 23 and 24 are conceptual and schematic diagrams illustrating a top and front view, respectively, of an example IMD with two channels for receiving two leads that is otherwise substantially similar to the IMD of FIGS. 19 and 20.
Figure 24:
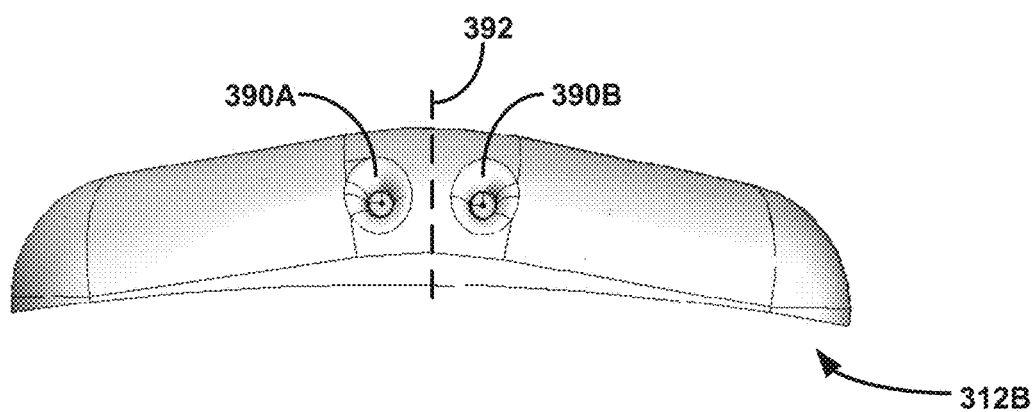

FIGS. 23 and 24 are conceptual and schematic top and side views, respectively, of example IMD 312B. IMD 312B may be substantially similar to IMD 312A with the exception of any differences described herein. IMD 312B may be substantially mirrored across central plane 392 of IMD 312B. IMD 312B defines two channels 390A, 390B (collectively, "channels 390"). Channels 390 may be on either side of central plane 392. Channels 390 may be spaced apart enough for separate coils 394A, 394B (collectively, "coils 394") to wrap around respective channels 390 without the coils 394 contacting each other or otherwise interfering with each other.

As a result of having two channels 390, IMD 312B may be configured to simultaneously provide therapy to and/or monitor patient 18 through two separate leads 14. In some examples, as a result of utilizing two leads 14 received by IMD 312B through two channels 390, more (or otherwise different) internal components 318 may be necessary. For example, power source 58 may need relatively more power to supply a sufficient amount of power to both leads 14 within both channels 390. Similarly, stimulation circuitry 52 may need to be more robust to provide potentially different electrical signals to both leads 14. However, some internal components 318 of IMD 312B may be substantially similar to respective internal components 318 of IMD 312A. For example, IMD a processing circuitry 50 of IMD 312A may be substantially similar to a processing circuitry 50 for IMD 312B.

FIGS. 25 and 26 are conceptual and schematic diagrams illustrating an isometric and cross-sectional front view from cut plane 440, respectively, of an example IMD 412A. IMD 412A may be substantially similar to IMD 12, IMD 112A, IMD 212A, and IMD 312A except for any differences described herein. IMD 412A includes tether 414, housing 416, and any internal components as described herein. For example, internal components of IMD 412A may include processing circuitry 50, stimulation circuitry 52, memory 54, telemetry circuitry 56, sensor 60, and/or recharge coil 66 as discussed herein. Tether 414 may be securely attached to housing 416, such that it may be difficult or impossible to detach tether 414 from housing 416 without destroying one or both of tether, 414 and/or housing 416. Tether 414 may include terminal 418 that is configured to receive lead 14 (and therein electrically couple lead 14 to internal components of IMD 412A).

Tether 414 may be configured to function as an extension of lead 14. For example, tether 414 may be internally constructed substantially similar to lead 14 (e.g., tether 414 may include one or more internal elongated conductors (not depicted) that extend from terminal 418 to housing 416, such that tether 414 electrically isolates the one or more elongated conductors). Terminal 418 of tether 414 may securely receive lead 14 such that lead 14 may not become unsecured (and therein electrically uncoupled) from IMD 412A without purposeful removal (e.g., by a clinician) of lead 14 from terminal 418. For example, similar to IMDs 112A, 212A, 312A as described above, IMD 412A may define one or more securing bores that are configured to extend from an outer surface of terminal 418 into channel 432 and may include one or more securing elements configured to pseudo-permanently secure lead 14 within channel 432 once lead 14 is received by channel 432. Further, one or more elongated conductors of tether 414 may be electrically coupled to the internal components of IMD 412A (e.g., through connectors as described herein located at a proximal end of tether 414), such that when lead 14 is received by terminal 418 lead 14 is electrically coupled to the intended internal components of 412A.

Alternatively, in some examples, lead 14 may be configured to be repeatedly removable from terminal 418, such that none of terminal 418, tether 414, or lead 14 are damaged by the act of repeatedly coupling/receiving and uncoupling/removing lead 14 from terminal 418. Configuring IMD 412A such that lead 14 may be received by and removed from terminal 418 at distal end of tether 414 without disturbing implanted housing 416 may improve an ability to maintain an implanted medical system 10.

Housing 416 and tether 414 may be made of any of the biocompatible materials discussed herein. Housing 416 may be made of a substantially rigid material. Alternatively, tether 414 may be configured to be relatively flexible. For example, tether 414 may comprise a relatively flexible material such as silicone or low-density polyethylene (LDPE) or the like. In other examples, housing 416 and tether 414 may all comprise a single structure with substantially similar properties. Housing 416 may be hermetically sealed. In some examples, tether 414 may also be hermetically sealed, whether separately or in a single seal that includes the cavity of housing 416.

Housing 416 may be generally mirrored across central plane 428 extending through the middle of housing 416 as viewed from front side 424 of housing 416, where front side 424 of housing 416 is the side of housing 416 opposite the tether 414. Housing 416 may define two major surfaces, top major surface 420 and bottom major surface 422. Bottom major surface 422 may be configured to contact cranium 20 upon implantation of IMD 412A. Both top major surface 420 and bottom major surface 422 may be substantially curved. In some examples, both surfaces 420, 422 define generally parabolic curves.

Bottom major surface 422 may be configured to generally align with curvature of cranium 20. Sidewall 434 of housing 416 may connect bottom major surface 422 to top major surface 420. Width 436 of top major surface 420 may be smaller than width 438 of bottom major surface 422 as measured along cross-sectional cut plane 440 that is generally perpendicular to top major surface 420, such that a cross-sectional shape of housing 416 is generally trapezoidal. In other examples housing 416 may define different shapes in cross-section. Distance 442 between top major surface 420 and bottom major surface 422 may be substantially constant throughout housing 416. By configuring housing 416 to define bottom major surface 422 that contours to cranium 20 and top major surface 420 that is relatively parallel to bottom major surface 422, IMD 412A may define a smooth profile that may reduce a chance of irritation or damage to nearby tissue of patient 18 while maximizing an ability of an internal cavity to house internal components.

Top major surface 420 and/or bottom major surface 422 may define substantially rectangular shapes. In other examples, top surfaces 420 and/or bottom major surface 422 may define substantially circular shapes, or other hexagonal shapes, or the like. In some examples, top major surface 420 may define a substantially similar shape as is defined by bottom major surface 422.

Housing 416 may define a plurality of corners 430A-B (collectively "corners 430"). Corners 430 may be substantially rounded, such that adjacent sidewalls of housing 416 generally do not meet at a right angle even where these adjacent outer edges run substantially perpendicular to each other. Configuring corners 430 to be substantially rounded may promote the comfort of IMD 412A and reduce chances of housing 416 catching, tearing, or otherwise damaging surrounded tissue following implantation of IMD 412A (e.g., as a result of a theoretical sharp/right angle corner/acute corner). Further, housing 416 may define chamfer 450 between bottom major surface 422 and sidewall 434. In some examples (not depicted), housing 416 may define a curve between sidewall 434 and bottom major surface 422. Configuring housing 416 to define chamfer 450 (or a curve) between sidewall 434 and bottom major surface 422 may reduce an angle housing 416 makes in contacting patient 18, therein reducing a chance of skin erosion or cosmesis.

Housing 416 may define internal cavity 448 between top major surface 420 and bottom major surface 422. Cavity 448 may be configured to receive circuits, sensors, and or power source 58. Circuits and/or sensors may be on a rigid-flex PCB. Using a rigid-flex hybrid PCB may enable circuits and/or sensors to flex according to the curvature of housing 416.

IMD 412A may include channel 432 for coupling lead 14 to IMD 412A. Channel 432 may be a substantially straight and continuous bore or hole that extends through distal terminal 418. Mouth 444 of channel 432 at distal end 446 of IMD 412A may be configured to receive lead 14 may taper as described herein. Channel 432 may extend through tether 414 and terminate inside housing 416. Further, as discussed above, tether 414 may be flexible, such that tether 414 and terminal 418 may wrap around housing 416. Further, in some examples, terminal 418 may be configured to be relatively flexible (e.g., as a result of being constructed of a relatively flexible material), such that both tether 414 and terminal 418 may flex around the housing 416. Configuring tether 414 and/or terminal 418 to be flexible such that tether 414 and/or terminal 418 may at least partially wrap around housing 416 may enable IMD 412A to receive lead 14 when lead 14 is located at a plurality of locations relative to housing 416. Configuring IMD 412A to receive lead 14 when lead 14 is at a plurality of locations relative to housing 416 may reduce a chance of lead 14 causing complications as discussed herein as lead 14 extends from IMD 412A to burr hole 26.

In some examples, tether 414 may extend into housing 416 closer to top major surface 420 than bottom major surface 422. Connecting tether 414 to housing 416 relatively closer to top major surface 420 than to bottom major surface 422, may improve an ability of tether 414 to extend out from IMD 412A without catching on or otherwise contacting cranium 20.

In some examples, a coil that is part of telemetry circuitry 56 and/or recharge coil 66 may wrap around channel 432 within terminal 418. To the extent that the coil in terminal 418 is recharge coil 66, an inductive recharge energy may include a relatively higher frequency (e.g., 1 megahertz) rather than an allowable frequency if recharge coil 66 were immediately adjacent to other internal components. Locating recharge coil 66 within IMD 412A such that recharge coil may receive a relatively higher frequency may enable IMD 412A to recharge power source 58 more efficiently. Terminal 418 may comprise a non-metallic material surrounding at least some of this coil to allow for the uninhibited transmission of signals to and from the coil.

Figure 27:
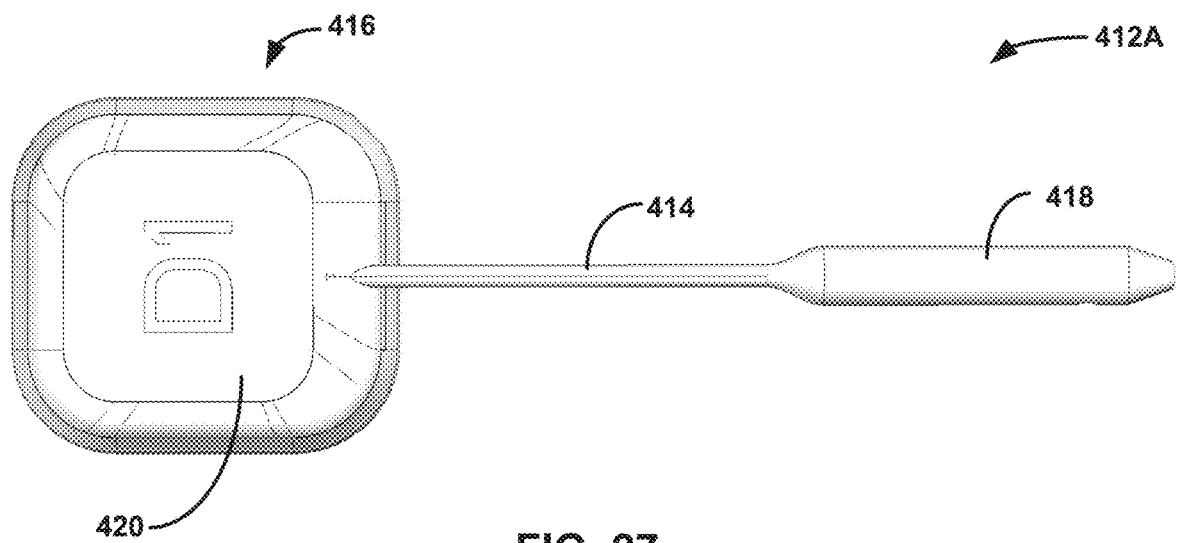
FIGS. 27-29 are conceptual and schematic diagrams illustrating a front, side, and isometric view, respectively, of the IMD of FIGS. 25 and 26.
Figure 28:
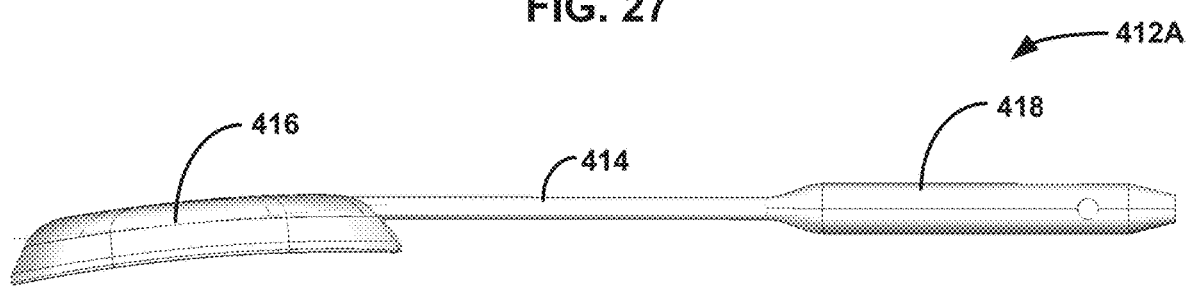
Figure 29:
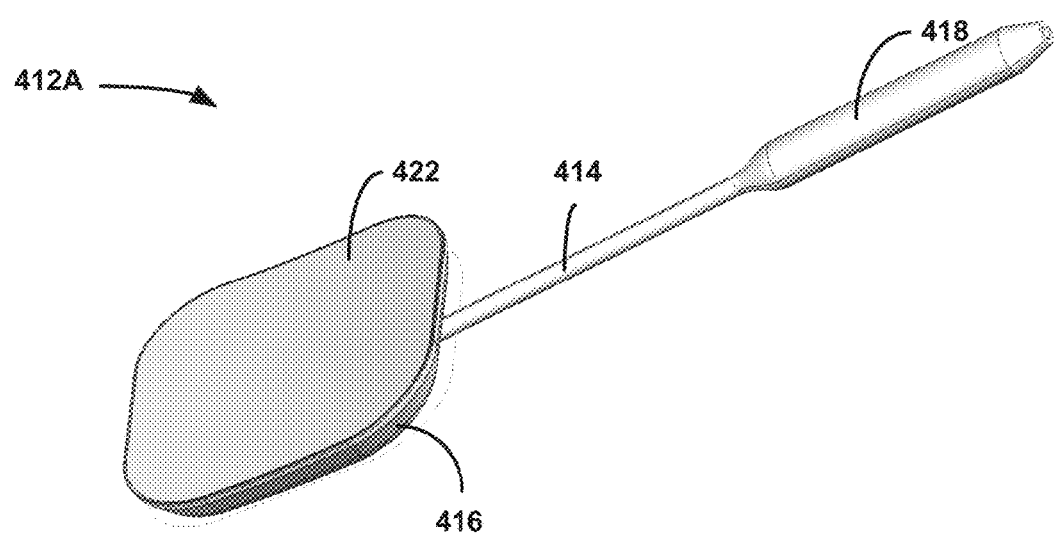

FIGS. 27-29 are conceptual and schematic top, side, and isometric views, respectively, of IMD 412A. FIG. 27 depicts IMD 412A as secured to cranium 20. In some examples (not depicted), IMD 412A may be secured within recess 28 of cranium 20 as described herein, though a relatively low profile of IMD 412A may make such a practice unnecessary. As depicted, IMD 412A is secured to cranium 20 with top major surface 420 "up" (relatively further away from cranium 20) and bottom major surface 422 contacting cranium 20. In some examples, housing 416 of IMD 412A may include fixtures through which screws may be inserted and therein screwed into cranium 20. These fixtures (not depicted) may extend out from housing 416 at a location where the fixtures are relatively unlikely to contact or interfere with tether 414.

Figure 30:
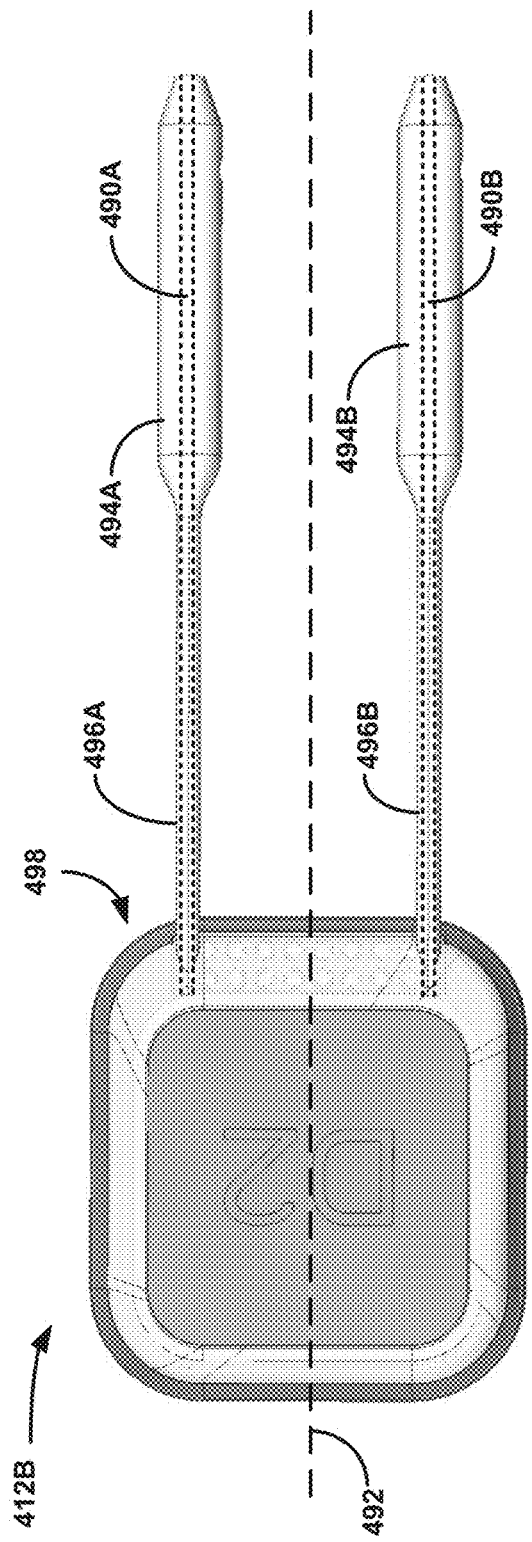
FIGS. 30-32 are conceptual and schematic diagrams illustrating a top, side, and isometric view, respectively, of an example IMD with two channels for receiving two leads that is otherwise substantially similar to the IMD of FIGS. 25 and 26.
Figure 31:
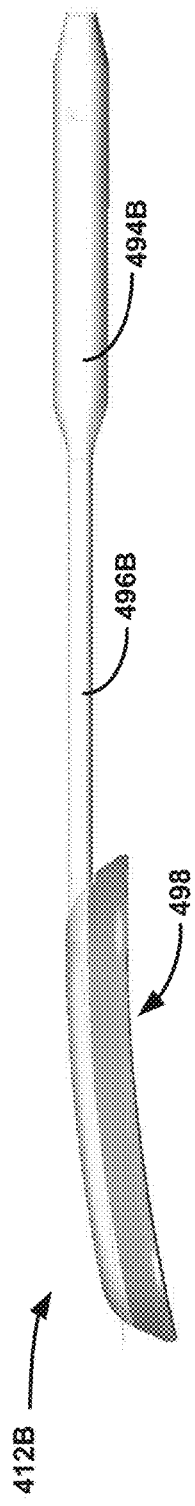
Figure 32:
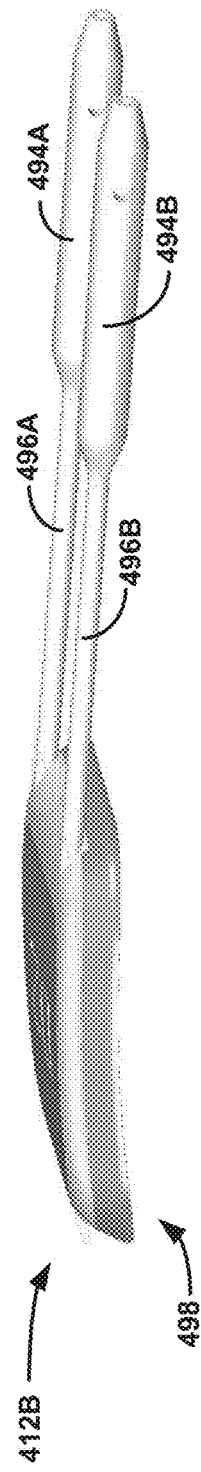

FIGS. 30-32 are conceptual and schematic top, side, and isometric views, respectively, of example IMD 412B. IMD 412B may be substantially similar to IMD 412A with the exception of any differences described herein. IMD 412B may be substantially mirrored across central plane 492 of IMD 412B. IMD 412B defines two channels 490A, 490B (collectively, "channels 490"). Channels 490 may be on either side of central plane 492. Each channel 490 may begin at a mouth of a respective terminals 494A, 494B (collectively "terminals 494") and extend through a respective tether 496A, 496B (collectively, "tethers 496") before terminating in housing 498.

As a result of having two channels 490, IMD 412B may be configured to simultaneously provide therapy to and/or monitor patient 18 through two separate leads 14. In some examples, as a result of utilizing two leads 14 received by IMD 312B through two channels 490, more (or otherwise different) internal components may be necessary. For example, power source 58 may need relatively more power to supply a sufficient amount of power to both leads 14 within both channels 490. Similarly, stimulation circuitry 52 may need to be more robust to provide potentially different electrical signals to both leads 14. However, some internal components of IMD 412B may be substantially similar to respective internal components of IMD 412A. For example, IMD a processing circuitry 50 of IMD 412A may be substantially similar to a processing circuitry 50 for IMD 412B.

FIGS. 33 and 34 are conceptual and schematic diagrams illustrating an isometric and cross-sectional front view from cut plane 500, respectively, of an example IMD 512A. IMD 512A may be substantially similar to IMD 12, IMD 112A, IMD 212A, IMD 312A, and IMD 412A except for any differences described herein. IMD 512A includes tether 514, housing 516, and any internal components as described herein. For example, internal components of IMD 512A may include processing circuitry 50, stimulation circuitry 52, memory 54, telemetry circuitry 56, sensor 60, and/or recharge coil 66 as discussed herein. Tether 514 may be securely attached to housing 516, such that it may be difficult or impossible to detach tether 514 from housing 516 without destroying one or both of tether 514 and/or housing 516.

Housing 516 and tether 514 may be made of any of the biocompatible materials discussed herein. Housing 516 may be made of a substantially rigid material. Alternatively, tether 514 may be configured to be relatively flexible. For example, tether 514 may comprise a relatively pliable material such as LDPE or the like. In other examples, housing 516 and tether 514 may both comprise a single structure with substantially similar properties. Housing 516 may be hermetically sealed. In some examples, tether 514 may also be hermetically sealed, whether separately or together with housing 516.

Housing 516 may be generally mirrored across central plane 510 extending through the middle of housing 516. Central plane 510 may extend along tether 514 when tether 514 is not flexing but is instead extending straight out from housing 516. Housing 516 may define two major surfaces, top major surface 520 and bottom major surface 522. Bottom major surface 522 may be configured to rest against cranium 20 upon implantation. Top major surface 520 and bottom major surface 522 may be substantially parallel, such that top surface is a fixed distance 524 from bottom major surface 522 as measured along an axis generally perpendicular to both top major surface 520 and bottom major surface 522.

In some examples, top major surface 520 and bottom major surface 522 may be curved. Top major surface 520 and/or bottom major surface 522 may be curved in only a single dimension. In some examples, both surfaces 520, 522 may define generally parabolic curves. Top major surface 520 and bottom major surface 522 may define generally similar curves, such that top major surface 520 and bottom major surface 522 are curve according to a similar slope in the single dimension. In some examples, the single dimension may be the dimension along which tether 514 extends from housing 516. In some examples, bottom major surface 522 may curve to generally align with curvature of cranium 20, and top major surface 520 may curve to stay substantially parallel with bottom major surface 522.

Top major surface 520 and/or bottom major surface 522 may define substantially oval or circular shapes, or some other shape that is substantially without edges. In some examples, width 526 of top major surface 520 may be smaller than width 528 of bottom major surface 522 as measured along cross-sectional cut plane 500 that is generally perpendicular to top major surface 520, such that a cross-sectional shape of housing 516 is generally trapezoidal. Top major surface 520 may define a substantially similar shape as is defined by bottom major surface 522. Sidewall 526 of housing 516 may extend between bottom major surface 522 and top major surface 520. A junction between sidewall 526 and top surfaces 520 may be rounded, such that sidewall 526 and top major surface 520 do not create a sharp angle at their junction. Similarly, the junction with sidewall 526 and bottom major surface 522 may be chamfered or rounded or the like to avoid creating a sharp angle. By configuring housing 516 to define bottom major surface 522, top major surface 520, and sidewall 526 that do not define sharp angles and make shapes that are substantially without edges (in the case of top major surface 520 and bottom major surface 522), IMD 512A may define a smooth profile that may reduce a chance of irritation or damage to nearby tissue of patient 18. Further, as noted above, configuring housing 516 to define a chamfer (or curve) between sidewall 526 and bottom major surface 522 may reduce an angle housing 516 makes in contacting patient 18, therein reducing a chance of skin erosion or cosmesis.

Housing 516 may define protrusion 530 that extends out from bottom major surface 522. Protrusion 530 may be configured to fit within recess 28 created in cranium 20. For example, protrusion 530 may be in recess 28 that is configured to fit protrusion 530 but not bottom major surface 522. Sidewall 538 of protrusion 530 may extend a length 534 from bottom major surface 522 that is substantially similar to a depth of recess 28, enabling surface 536 of protrusion 530 to substantially align with cranium 20 within recess 28 while bottom major surface 522 aligns with cranium 20 external to recess 28. Surface 536 of protrusion 530 may be substantially parallel with bottom major surface 522.

Housing 516 may define internal cavity 540. Internal cavity may be between top major surface 520, sidewall 526, bottom major surface 522, protrusion sidewall 538, and surface 536. Cavity 540 may be configured to receive circuits, sensors, and or power source 58. Circuits and/or sensors may be on a rigid-flex PCB. Using a rigid-flex hybrid PCB may enable circuits and/or sensors to flex according to the curvature of housing 516. In some examples, power source 58 may be a substantially round battery substantially round battery and relatively thin battery. For example, power source 58 may be between 3-5 millimeters thick. Protrusion 530 may be configured to be the same size as power source 58, enabling power source 58 to fit within protrusion 530 without substantially extending past bottom major surface 522.

In some examples, portion 542 of housing 516 may be an overmold. Overmolded portion 542 of housing 516 may define some of sidewall 526 and bottom major surface 522, including the junction between the two. Overmold portion 542 may extend around substantially all of the perimeter of housing 516. In certain examples, overmold portion 542 may contain one or more internal components of IMD 512A. For example, overmold portion 542 may contain coil 544, which may be recharge coil 66 and/or telemetry coil for telemetry circuitry 56.

IMD 512A may include channel 532 for coupling lead 14 to IMD 512A. Channel 532 may be a substantially straight and continuous bore or hole that extends through distal terminal 518 of tether 514. Mouth 546 of channel 532 at distal end 548 of IMD 512A may be configured to receive lead 14. Channel 532 may extend through tether 514 and terminate inside housing 516. Further, as discussed above, tether 514 may be flexible, such that tether 514 may wrap around housing 516. Configuring tether 514 to be flexible such that tether 514 may flex at least partially around housing 516 may enable IMD 512A to receive lead 14 when lead 14 is located at a plurality of locations relative to housing 516. Configuring IMD 512A to receive lead 14 when lead 14 is at a plurality of locations relative to housing 516 may reduce a chance of lead 14 causing complications as discussed herein as lead 14 extends from IMD 512A to burr hole 26.

Tether 514 may extend from housing 516 relatively flush with bottom major surface 522 (e.g., such that the bottom major surface 522 is substantially aligned with tether 514). In examples where protrusion 530 is the only feature of IMD 512A within recess 28, configuring tether 514 to extend from housing 516 relatively flush with tether 514 may reduce a profile of IMD 512A.

In some examples, a coil that is part of telemetry circuitry 56 and/or recharge coil 66 may wrap around channel 532 within terminal 518 (e.g., alternatively or in addition to coil 544 in molded portion 542). To the extent that the coil in terminal 518 is recharge coil 66, an inductive recharge energy may include a relatively higher frequency (e.g., 1 megahertz) rather than an allowable frequency if recharge coil 66 were immediately adjacent to other internal components. Locating recharge coil 66 within IMD 512A such that recharge coil 66 may receive a relatively higher frequency may enable IMD 512A to recharge power source 58 more efficiently. Terminal 518 may comprise a non-metallic material surrounding at least some of this coil to allow for the uninhibited transmission of signals to and from the coil.

Figure 35:
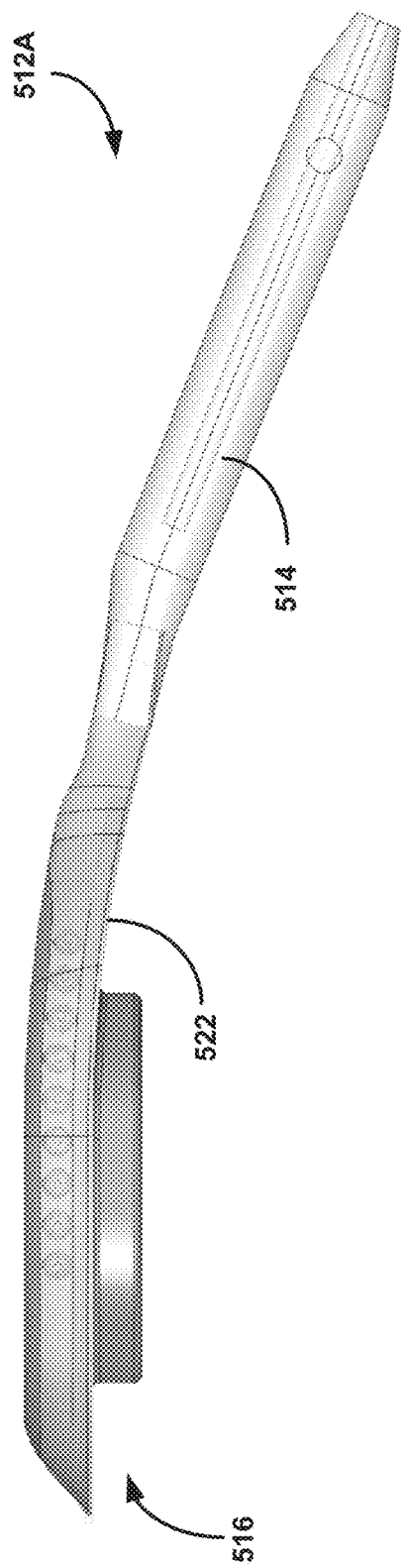
FIGS. 35 and 36 are conceptual and schematic diagrams illustrating a side and top view, respectively, of the IMD of FIGS. 33 and 34.
Figure 36:
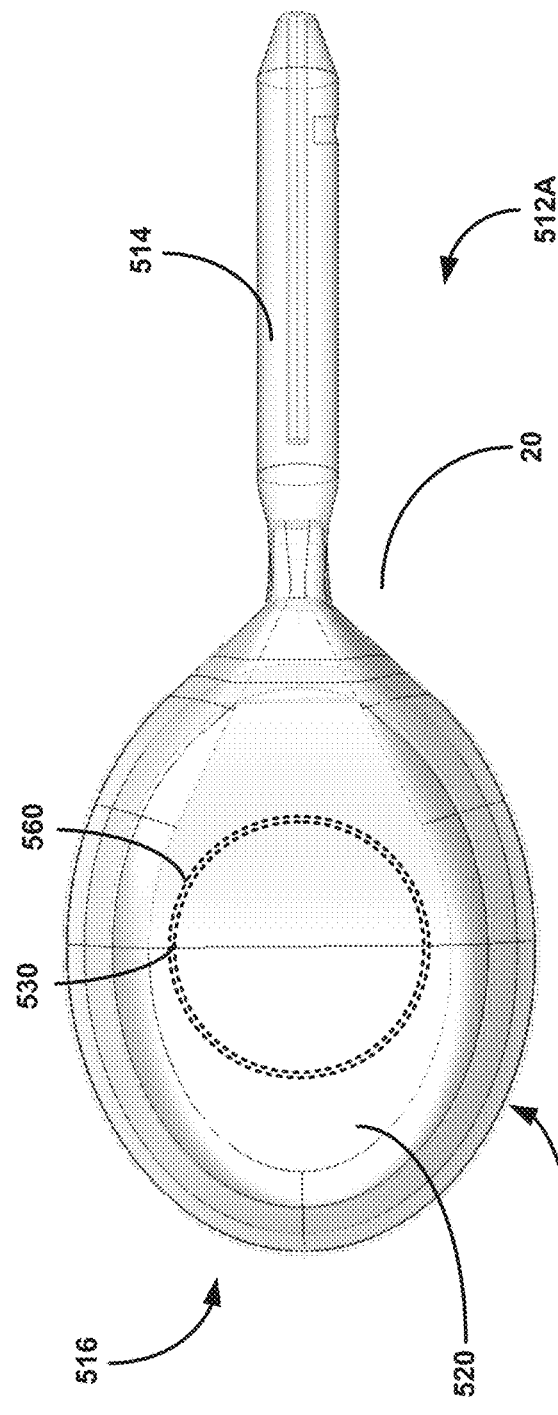

FIGS. 35 and 36 are conceptual and schematic side and top views, respectively, of IMD 512A. FIG. 35 depicts the flush junction between tether 514 and bottom major surface 522, such that bottom major surface 522 of housing 516 and tether 514 are substantially aligned at their intersection. FIG. 36 depicts IMD 512A as received by recess 560 of cranium 20. Recess 560 may be substantially similar to recess 28 as described herein. As depicted, recess 560 may be generally circular to receive protrusion 530, which is itself substantially circular in cross-section. Is it to be understood that recess 560 may be substantially any shape to receive protrusion 530. As depicted, IMD 512A is located in recess 560 with top major surface 520 "up" (relatively further away from cranium 20) and bottom major surface 522 contacting cranium 20 adjacent to recess 560. In some examples, housing 516 of IMD 512A may include fixtures through which screws may be inserted and therein screwed into cranium 20. These fixtures (not depicted) may extend out from housing 516 at a location where the fixtures are relatively unlikely to inhibit motion of tether 514 (e.g., on an opposite side of housing 516 relative to tether 514).

Figure 37:
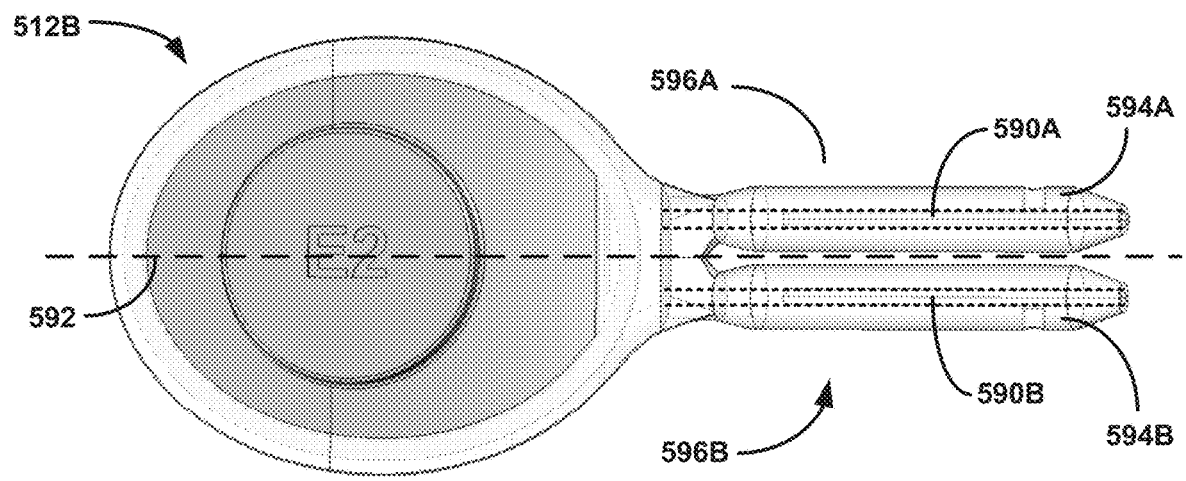
FIGS. 37-39 are conceptual and schematic diagrams illustrating a top, side, and isometric view, respectively, of an example IMD with two channels for receiving two leads that is otherwise substantially similar to the IMD of FIGS. 33 and 34.
Figure 38:
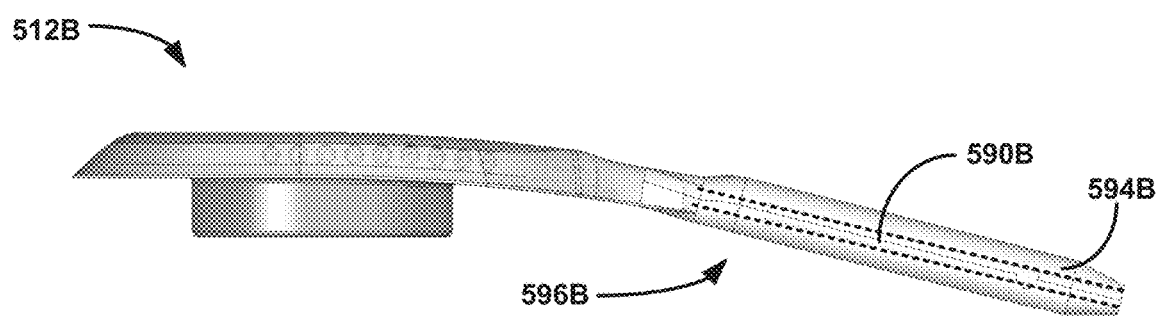
Figure 39:
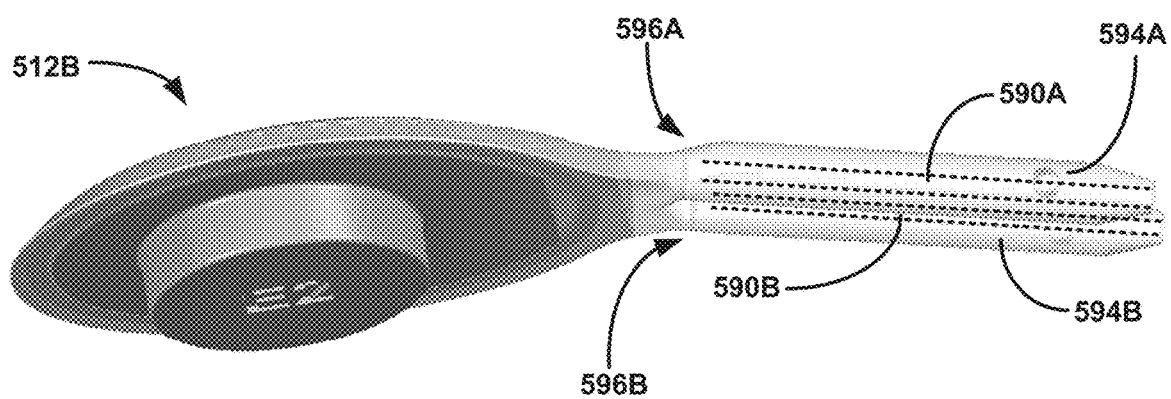

FIGS. 37-39 are conceptual and schematic bottom, side, and isometric views, respectively, of example IMD 512B. IMD 512B may be substantially similar to PAD 512A with the exception of any differences described herein. IMD 512B may be substantially mirrored across central plane 592 of IMD 512B. IMD 512B defines two channels 590A, 590B (collectively, "channels 590"). Channels 590 may be on either side of central plane 592. Each channel 590 may begin at a mouth of a respective terminals 594A, 594B (collectively "terminals 494") and extend through a respective tether 596A, 596B (collectively, "tethers 596") before terminating in housing 498.

As a result of having two channels 590, IMD 512B may be configured to simultaneously provide therapy to and/or monitor patient 18 through two separate leads 14. In some examples, as a result of utilizing two leads 14 received by IMD 512B through two channels 590, more (or otherwise different) internal components may be necessary. For example, power source 58 may need relatively more power to supply a sufficient amount of power to both leads 14 within both channels 590. Similarly, stimulation circuitry 52 may need to be more robust to provide potentially different electrical signals to both leads 14. However, some internal components of IMD 512B may be substantially similar to respective internal components of IMD 512A, For example, IMD processing circuitry 50 of POD 512A may be substantially similar to processing circuitry 50 for IMD 512B.

FIGS. 40 and 41 are conceptual and schematic diagrams illustrating an isometric view and a cross-sectional view, respectively, of an example IMD 612A. The cross-sectional view of FIG. 41 is taken along cross-sectional cut-plane 600 of FIG. 40. IMD 612A may be substantially similar to IMD 12, IMD 112A, IMD 212A, IMD 312A, IMD 412A, and/or IMD 512A except for any differences described herein. IMD 612A includes housing 616 and funneling section 618. Housing 616 defines cavity 640 that houses internal compartments of IMD 612. For example, internal components of IMD 612A may include processing circuitry 50, stimulation circuitry 52, memory 54, telemetry circuitry 56, sensor 60, and/or recharge coil 66 as discussed herein. Funneling section 618 may include a "porch" portion of IMD 612A that receives lead 14, such that, as received by IMD 612A, lead 14 may extend out from funneling section 618. Funneling section 618 may define mouth 646 of channel 632. Mouth 646 may be configured to receive lead 14. Channel 632 may extend through funneling section 618 to housing 616. Funneling section 618 may be securely attached to housing 616, such that it may be difficult or impossible to detach funneling section 618 from housing 616 without damaging one or both of funneling section 618 and/or housing 616. For example, funneling section 618 may be adhesively bonded to housing 616, or funneling section 618 may be welded to housing 616, or the like.

Housing 616 and funneling section 618 may be made of any of the biocompatible materials discussed herein. Housing 616 and funneling section 618 may both be made of a substantially rigid material, such as a metallic material as discussed herein (e.g., titanium), Both housing 616 and funneling section 618 may be made of a substantially rigid material in examples where a durability or a rigidity of both housing 616 and funneling section 618 is a concern, such that a relatively more rigid material may improve an ability of both housing 616 and funneling section 618 to maintain a structural integrity to address this concern.

In some examples, housing 616 and funneling section 618 may be made of different materials. For example, funneling section 618 may be configured to be relatively soft or yielding in comparison to housing 616 to better receive or guide lead 14. For example, housing 616 may include a metallic material such as titanium, and funneling section 618 may include a polymeric material such as polysulfone, polyurethane, epoxy, polyether ether ketone (PEEK), low-density polyethylene (LDPE), or the like. In other examples, housing 616 and funneling section 618 may both comprise a single structure with substantially similar properties. In certain examples, an outer wall of both housing 616 and funneling section 618 (e.g., a wall that substantially defines a shape of housing 616 and funneling section 618) may be made of a substantially similar material (e.g., such as titanium), while a material that is used to coat or overmold funneling section 618 may be different than a material that is used to coat or overmold housing 616, or a different amount of a substantially similar material may be used to coat housing 616 and funneling section 618, or the like. For example, a material that is used to coat funneling section 618 may be more yielding (e.g., softer and/or more deformably), and/or may be applied thicker than a material that is used to coat housing 616.

Cavity 640 of housing 616 may be sealed, such as hermetically sealed. In certain examples, securing funneling section 618 to housing 616 may function to seal some of cavity 640 of housing 616. For example, funneling section 618 may store some internal components of 612A such as telemetry coil of telemetry circuitry 56. In such examples, housing 616 may define windows or openings (not depicted) as described herein that align with windows of funneling section 618 to enable internal components such as telemetry circuitry 56 and/or processing circuitry 50 to be electrically coupled to the telemetry coil in funneling section 618. As such, securely attaching (e.g., through bonding or overmolding or the like) housing 616 to funneling section 618 may act to seal cavity 640 of housing 616. Alternatively, and/or additionally, funneling section 618 may also include a hermetically sealed compartment, whether separately or together with housing 616, that houses components of IMD 612A.

Together, housing 616 and funneling section 618 may define IMD 612A to be substantially disc-shaped (e.g., defining a squat cylinder) as depicted in FIG. 40. For example, when secured together, housing 616 and funneling section 618 may define two major surfaces, top major surface 620 and bottom major surface 622. Bottom major surface 622 may be configured to rest against cranium 20 upon implantation. Bottom major surface 622 may define a substantially flat plane, while top major surface 620 domes away from bottom major surface 622 as described herein. Both bottom major surface 622 and top major surface 620 may define substantially circular shapes. As a result of bottom major surface 622 and top major surface 620 defining substantially circular shapes such that IMD 612 is substantially disc-shaped, IMD 612A may be secured within a circular recess created in a cranium of a patient in substantially any orientation.

IMD 612A may include sidewall 624 that extends between top major surface 620 and bottom major surface 622. Both housing 616 and funneling section 618 may define a portion of sidewall 624. Height 602 of sidewall 624 (e.g., a distance between top major surface 620 and bottom major surface 622 as measured along an axis generally perpendicular to both top major surface 620 and bottom major surface 622) may be a substantially static distance along a perimeter of IMD 612A. Sidewall 624 may be substantially perpendicular with bottom major surface 622 as sidewall 624 extends across a perimeter of IMD 612A. In some examples, it may be easier to create recess 28 such that recess 28 defines a flat bottom surface. Further, it may be easier to create a cylindrical-shaped recess 28 (e.g., a recess with a circular cross-section). For example, where a recess is created with a drill, conventional drill bits may inherently create a cylindrical bore with a flat distal surface. Bottom major surface 622 may define a substantially flat plane that is configured to rest flush against a flat recess 28 of cranium 20 upon implantation of IMD 612A. In such examples, dimensioning bottom major surface 622 of IMD 612A to define a matching flat circular surface may improve a stability of IMD 612A upon implantation, as well as enable IMD 612A to rotate freely (prior to receiving lead 14) within recess 28. Further, defining sidewall 624 to extend substantially perpendicular away from bottom major surface 622 may improve an ability for IMD 612A to store internal components (which may themselves be largely orthotopes), therein decreasing an overall size of IMD 612A.

As discussed above, top major surface 620 may define a curved plane that "domes" away from bottom major surface 622 as top major surface 620 extends radially in from sidewall 624. Top major surface 620 may define a curvature that is substantially similar to a curvature of cranium 20 of patient 18. By configuring top major surface 620 to define a curvature that approximates an adjacent curvature of cranium 20 of patient 18 upon implantation, IMD 612A may reduce the likelihood of complications that result from jutting IMDs as described herein, in addition to improving an appearance of IMD 612A (by making IMD 612A less noticeable upon implantation).

A junction between sidewall 624 and top major surface 620 may be rounded, such that sidewall 624 and top major surface 620 do not create a sharp angle at their junction. Similarly, the junction with sidewall 624 and bottom major surface 622 may be chamfered or rounded or the like to avoid creating a sharp angle. By configuring housing 616 and funneling section 618 to securely attach to each such that bottom major surface 622, top major surface 620, and sidewall 624 do not define sharp angles but rather define shapes and contours that are substantially without edges (in the case of top major surface 620 and bottom major surface 622), IMD 612A may define a smooth profile that may reduce a chance of irritation or damage to nearby tissue of patient 18. Further, as discussed in relation to other IMDs above, configuring housing 616 to define a chamfer (or curve) between sidewall 624 and bottom major surface 622 may reduce an angle that housing 616 may define upon contacting cranium 20 of patient 18, therein reducing a chance of skin erosion or cosmesis (e.g., in examples where IMD 612A is not implanted in a recess 28).

As discussed above, housing 616 and funneling section 618 may be configured to fit within recess 28 created (e.g., drilled or cut) in cranium 20, such that bottom major surface 622 contacts recess 28 and recess 28 is substantially the same shape and size as bottom major surface 622. In some examples, height 602 of sidewall 624 as measured along an axis that is perpendicular to bottom major surface 622 may be substantially similar to a depth of recess 28, enabling top major surface 620 to substantially align with cranium 20 (e.g., an outer surface of cranium that is adjacent to recess 28). In other examples, a depth of recess 28 may be less than height 602 of sidewall 624. For example, recess 28 may define a depth that is generally the same (or slightly less than) the height of mouth 646 of channel 632 within IMD 612A, such that lead 14 may extend out of mouth 646 of IMD 612A generally planar with cranium 20.

Housing 616 may define groove 610 that extends from top major surface 620 toward bottom major surface 622. Groove 610 may extend in a relatively straight line across top major surface 620. Groove 610 may be defined entirely by housing 616, such that groove 610 does not extend into funneling section 618. Further, housing 616 may define groove 610 such that groove 610 does not extend to sidewall 624 of housing 616. Walls of groove 610 may converge as groove 610 extends from top major surface 620 towards bottom major surface 622. Put differently, at least one wall of groove 610 (e.g., a wall that is substantially parallel with longitudinal axis 608 of channel 632 on a first side of longitudinal axis 608) extends towards an opposite wall (e.g., a wall that is substantially parallel with longitudinal axis 608 on a second side of longitudinal axis 608). For example, groove 610 may be define a generally "V" shaped depression in top major surface 620 extending towards bottom major surface 622 as depicted in FIG. 41.

Groove 610 may define a longitudinal axis that is substantially coaxial with longitudinal axis 608 of channel 632. Groove 610 may extend into top major surface 620 to expose an external surface of a component of IMD 612A that defines channel 632 (e.g., a component such as stack 644 as described with reference to FIG. 43). In some examples, this component that defines channel 632 may be discrete component that may be received by groove 62 and then securely attaching groove 610 (e.g., as a result of welding or the like).

Groove 610 may define one or more openings 604 through which connectors 638 may extend into cavity 640 to electrically couple to internal components. For example, one or more openings 604 may be defined along a length of groove 610. As a result of groove 610 defining openings 604, connectors 638 (e.g., which may be conductor pins or the like) may extend through openings 604 and be soldered or the like to circuit boards to electrically couple to internal components. In this way, groove 610 enables connectors 638 to electrically couple lead 14 to internal components (e.g., electrically coupled to lead 14 through stack 644 as described with reference to FIG. 43). Connectors 638 may extend through openings 604 and then welded at openings 604 to hermetically seal cavity 640 of housing 616. Connectors 638 may also be welded to the component that defines channel 632 to electrically coupled connectors 638 to lead 14 and securely attach connectors 638 to lead 14, as discussed below with reference to FIG. 48 below. In some examples, all connectors 638 of IMD 612A may extend to one longitudinal wall of channel 632 as depicted in FIGS. 40 and 41. In such examples, one or more connectors 638 may be electrically coupled to internal components on an opposite side of cavity 640. In other examples (not depicted), some connectors 638 may extend from groove 610 to a first side of channel 632 while other connectors 638 may extend to an opposite side of channel 632.

Where IMD 612A includes groove 610, IMD 612A may include cover 614 that may be configured to cover groove 610 once all relevant connections are made between internal components and lead 14 as described herein. In FIG. 40, IMD 612A is depicted as partially exploded with cover 614 removed from housing 616 to better illustrate groove 610 and connectors 638 that electrically couple lead 14 to internal components within groove 610. Cover 614 may substantially enclose groove 610 such that top major surface 620 of IMD 612A is substantially continuous over groove 610. In some examples, cover 614 may be a discrete component that may be bonded or attached to housing 616 by any means described herein or otherwise known to one of ordinary skill in the art (e.g., mechanically affixed, chemically bonded, or the like). In other examples, cover 614 may include a portion of housing 616 that covers groove 610 as part of an assembling or manufacturing process. For example, cover 614 may be a part of an overmold that covers housing 616 and/or fills some or all of groove 610.

As discussed above, housing 616 may define internal cavity 640. Cavity 640 may be a space between top major surface 620, sidewall 624, and bottom major surface 622. Further, in examples where IMD 612A includes groove 610, cavity 640 may be partially defined by groove 610 as depicted in FIG. 41. In some examples, cavity 640 may be sealed once connector(s) 638 are received and by openings 604 and then sealed (e.g., welded) at openings 604.

Where lead 14 has a plurality of distal electrodes, lead 14 may include a corresponding plurality of terminal connection points at a proximal end of lead 14 as discussed herein. In such examples, IMD 612A may include a respective connector 638 for each terminal connection point, such that each connection point may be electrically coupled to a respective one of the one or more connectors 638. As depicted in FIG. 41, a first segment of connectors 638 may extend out away from openings 604 at an angle that is generally perpendicular to a respective wall of groove 610 from which the respective connector 638 extends. Configuring the first segment of connectors 638 to extend away from openings 604 at an angle that is generally perpendicular to a respective wall of groove 610 in this way may simplify the process of securing (e.g., welding) respective connectors 638 in place by improving lines of access to the first segments (as discussed in greater detail with respect to FIG. 48).

In some examples, upon the first segments of connectors 638 extending away from openings 604 at an angle that is substantially perpendicular to a respective wall of groove 610 through which connectors 638 extend as discussed, a second segment of connectors 638 may angle to define an axis that is substantially parallel with bottom major surface 622. The second segment of connectors 638 may be adjacent the first segment of connectors 638. The second segment of connectors 638 may be electrically coupled to lead 14 (e.g., through stack 644 as defined below with respect to FIG. 43). Configuring the second segments of respective connectors 638 to angle to define an axis that is parallel with bottom major surface 622 may reduce a height and therein size of IMD 612A.

Cavity 640 may be configured to receive circuits, sensors, and or power source 58. Circuits and/or sensors may be on a rigid-flex PCB. Using a rigid-flex hybrid PCB may enable circuits and/or sensors to flex according to the curvature of housing 616, such as the curvature of top major surface 620. These circuits, sensors, or connections for the same may extend below channel 632 adjacent bottom major surface 622 within cavity 640. In some examples, power source 58 may be a substantially D-shaped battery that is sized to fit on one half of housing 616. In some examples, channel 632 may extend radially into housing 616 along an axis that bisects the housing 616 into two halves of substantially different sizes. For example, one side of housing 616 as bisected by channel 632 may include up to 50% more volume than the other side of housing 616 as bisected by channel 632. In some examples, channel 632 defines one side of housing 616 to be substantially the same size as a D-shaped battery that serves as power source 58 of IMD 612A, such that the other side of housing 616 secures the circuits and sensors of IMD 612A. For example, the other side of housing 616 may receive substantially all of processing circuitry 50, stimulation circuitry 52, and telemetry circuitry 56.

In some examples, some of housing 616 and/or funneling section 618 may be covered with an overmold, either before or after funneling section 618 is secured/affixed to housing 616. An overmold of IMD 612A may define some of sidewall 624, top major surface 620, or bottom major surface 622, including the junction between any of sidewall 624, top major surface 620, and bottom major surface 622 as described herein. In some examples, an overmold portion may extend around substantially all of the perimeter of housing 616 and/or funneling section 618. In certain examples, an overmold of IMD 612A may contain or otherwise cover or partially secure one or more internal components of IMD 612A. For example, an overmold coating some of IMD 612A may contain or cover a coil of IMD 612A (e.g., recharge coil 66 and/or telemetry coil for telemetry circuitry 56) that wraps around housing 616 and/or funneling section 618 of IMD 612A.

As discussed above, IMD 612A may include channel 632 for coupling lead 14 to IMD 612A. Channel 632 may be a substantially straight and continuous bore or hole that extends radially into housing 616 and terminates inside housing 616. Mouth 646 of channel 632 may be defined by funneling section 618 and configured to receive lead 14. Funneling section 618 may define mouth 646 at a location that is radially recessed within funneling section 618. Put differently, funneling section 618 may define mouth 646 at a location that is relatively closer to a radial "center" of IMD 612A (e.g., in comparison to a radial distance between sidewall 624 and the radial center). Configuring mouth 646 to be radially recessed within funneling section 618 may facilitate lead 14 deflecting away from bottom major surface 622 before extending past sidewall 624 as lead 14 extends towards burr hole 26 of cranium 20 as discussed herein. In other words, as a result of funneling section 618 defining mouth 646 at a radially recessed location, lead 14 that is received by IMD 612A may be able to deflect and/or curl up and away from bottom major surface 622 of IMD 612A before passing a plane of sidewall 624 of IMD 612A in order to avoid contact with cranium 20. Enabling lead 14 to deflect away from bottom major surface 622 before passing a plane of sidewall 624 as received by IMD 612A may increase a potential depth to which recess 28 may be cut (and therein which IMD 612A may be secured to), such that a profile of IMD 612A relative to cranium 20 may be reduced while an integrity of lead 14 is protected (e.g., by avoiding forcing lead 14 to "kink" up away from bottom major surface 622 at a relatively extreme angle).

Funneling section 618 may further define funneling walls 626A-626C (collectively "funneling walls 626) that define a surface that transitions from sidewall 624 to a surface of funneling section 618 that defines mouth 646. Funneling walls 626 may define this surface to be substantially smooth and rounded. For example, funneling walls 626 may define a rounded or fillet corner with a radius of between 1 millimeters and 4 millimeters. Funneling walls 626 may be configured to contact lead 14 as lead 14 extends out from mouth 646 and curls around at least a portion of sidewall 624. Funneling walls 626 may be configured to define a surface that enables lead 14 to avoid kinking or otherwise deflecting at an angle that may cause damage to lead 14 if lead 14 contacts funneling walls 626 as lead 14 extends away from mouth 646. In this way, so long as lead 14 has substantially continuous contact (e.g., rather than bending away from contact and then bending to be back in contact) with funneling walls 626 and sidewall 624 upon exiting mouth 646 and curling around at least a portion of sidewall 624, lead 14 may substantially avoid deflecting at an angle that decreases the integrity of lead 14. Configuring funneling walls 626 to define a surface upon which lead 14 may contact as lead 14 curls around IMD 612A with little or no risk of damage to lead 14 may enable lead 14 to flex at least partially around funneling section 618 and/or housing 616 once IMD 612A is secured to cranium 20 of patient 18. Enabling lead 14 to flex at least partially around IMD 612A with little or no risk to an integrity of lead 14 may enable IMD 612A receive lead 14 when lead 14 extends radially out from IMD 612A in a plurality of directions. Configuring lead 14 to extend from IMD 612A in a plurality of directions relative to an orientation of IMD 612A may reduce a chance of lead 14 causing (or experiencing) complications as discussed herein as lead 14 extends toward burr hole 26.

In some examples, a "bottom" funneling wall 626C that is generally parallel with bottom major surface 622 may extend away from mouth 646 to sidewall 624. Alternatively, in certain examples bottom funneling wall 626C may extend from bottom major surface 622 up towards top major surface 620 as bottom funneling wall 626C extends from mouth 646 to sidewall 624. Configuring funneling wall 626C to extend towards top major surface 620 as this funneling wall 626C extends towards sidewall 624 may better enable lead 14 to extend up from channel 632 towards top major surface 620 and therein out of recess 28 as discussed herein.

In some examples, a coil that is part of telemetry circuitry 56 and/or recharge coil 66 may be secured within funneling section 618 (e.g., alternatively or in addition to a coil that extends around housing 616 under a molding that covers housing 616 as discussed above). To the extent that the coil in funneling section 618 is recharge coil 66, an inductive recharge energy may include a relatively higher frequency (e.g., 1 megahertz) rather than an allowable frequency if recharge coil 66 were immediately adjacent to other internal components (e.g., within housing 616). Locating recharge coil 66 within IMD 612A such that recharge coil 66 may receive a relatively higher frequency may enable IMD 612A to recharge power source 58 more efficiently. Funneling section 618 may comprise a non-metallic material surrounding at least some of this coil to allow for the uninhibited transmission of signals to and from the coil.

Figure 42:
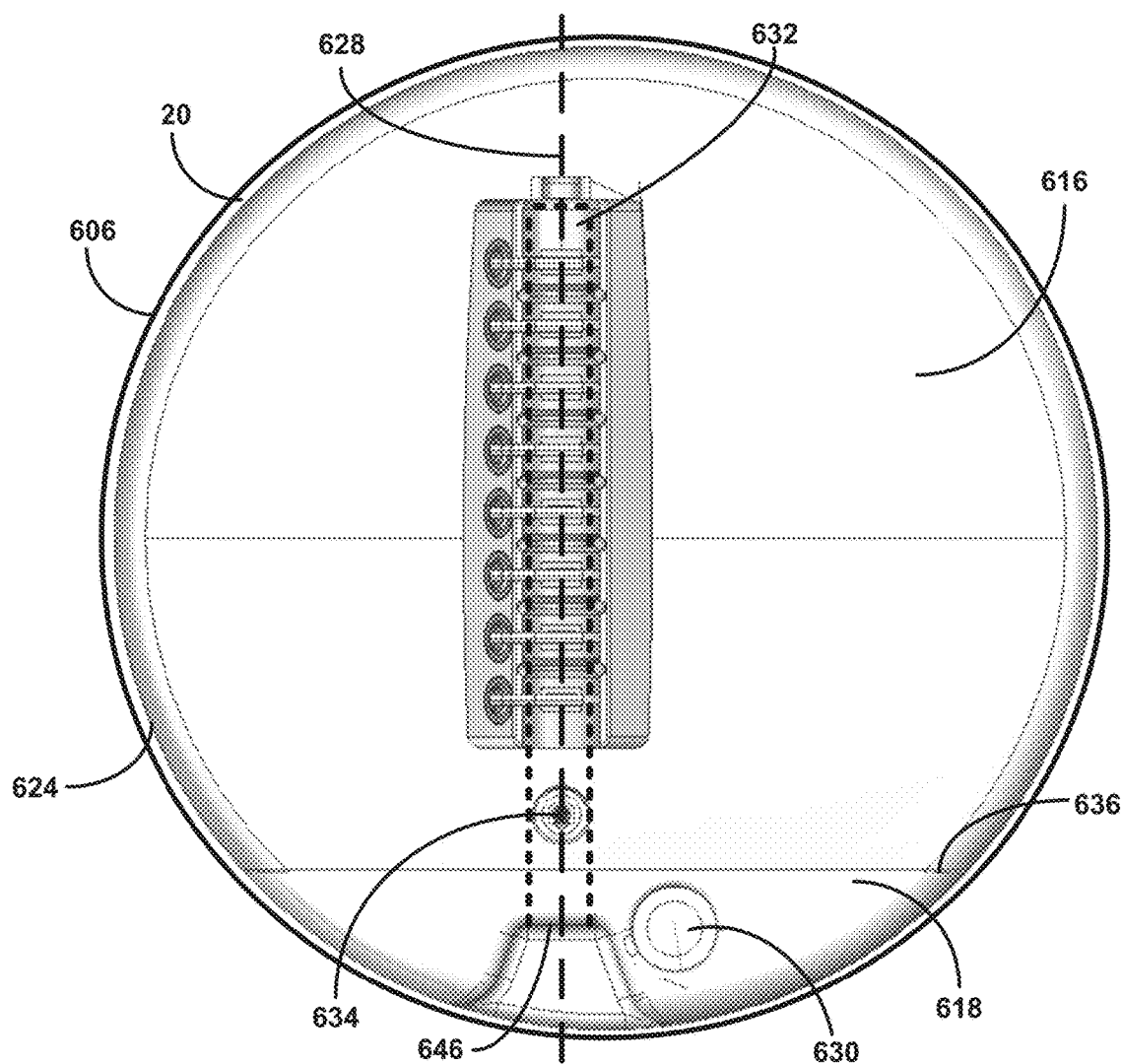
FIGS. 42 and 43 are conceptual and schematic diagrams illustrating a top and cross-sectional view, respectively, of the IMD of FIG. 40.
Figure 43:
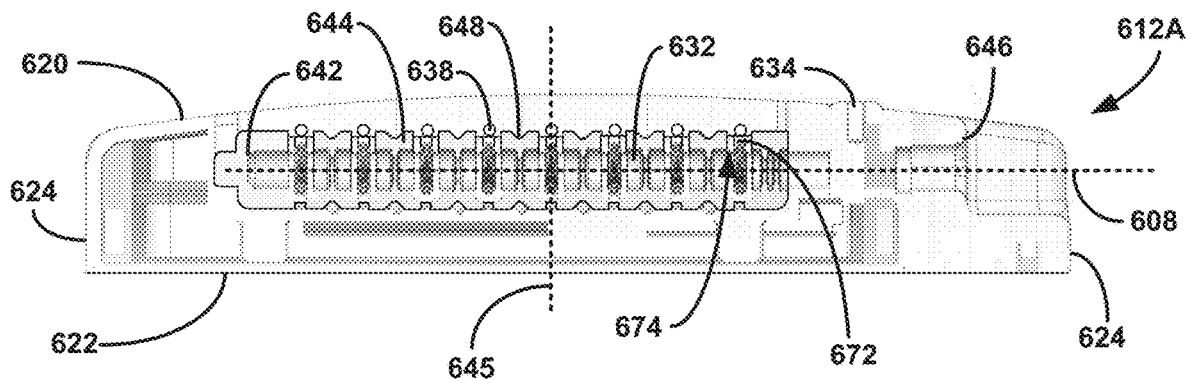

FIG. 42 is a conceptual and schematic top view of IMD 612A, and FIG. 43 depicts a conceptual and schematic cross-sectional side view from cut-plane 628 of FIG. 42. FIG. 42 depicts IMD 612A as received by recess 606 of cranium 20. Recess 606 may be substantially similar to recess 28 as described herein. As depicted, recess 606 may be generally circular to receive bottom major surface 622, which is itself substantially circular in cross-section. A clinician may create recess 606 by drilling a bit that is the shape and size of recess 606 into cranium 20. For example, a 5-centimeter drill bit may be used to make circular recess 606 that is 5 centimeters in diameter, which may be substantially the same diameter of IMD 612A. It is to be understood that recess 606 may be other shapes in other examples in order to receive bottom major surface 622 (e.g., where bottom major surface 622 is a different shape). As depicted, IMD 612A is located in recess 606 with top major surface 620 "up" (relatively further away from cranium 20) and bottom major surface 622 contacting cranium 20 within recess 606.

In some examples, housing 616 of IMD 612A may include fixtures such as bore 630 that extends through IMD 612A from top major surface 620 to bottom major surface 622 through which screws may be inserted and therein screwed into cranium 20. Alternatively, bore 630 may be used as a suture hole through which sutures may be threaded and therein connected to screws that are screwed into cranium 20. Further, in some examples IMD 612A may define a feature that may be used to secure lead 14 to IMD 612A once lead 14 is received by IMD 612. For example, as depicted in FIG. 42, top major surface 620 defines threaded hole 634 through which a securing bolt may be screwed to press against and providing a securing force to lead 14 once lead 14 is received by IMD 612A. It is to be understood that the relative location of bore 630 and threaded hole 634 within FIG. 42 are depicted for illustration only, and in other examples bore 630 and threaded hole 634 may be in different locations. Alternatively, or additionally, in some examples, IMD 612A may include more than one bore 630 and/or more than one threaded hole 634 or the like.

As discussed herein, funneling section 618 may be sized and configured to house one or more coils, such as a telemetry coil for telemetry circuitry 56. In some examples, some or all of funneling section 618 may be relatively transparent in order to enable a clinician coupling lead 14 to IMD 612A to visually see and monitor lead 14 being inserted into channel 632. In such examples, any coils housed by funneling section 618 may be located at a position that is less likely to impede a visual inspection of lead 14 as received by IMD 612A. For example, a coil housed within funneling section 618 may be located "under" mouth 646 of funneling section 618, which is to say a coiled housed by funneling section 618 may be relatively adjacent bottom major surface 622.

As depicted in FIG. 42, funneling section 618 and housing 616 may contact each other along a relative flat interface 636. This interface 636 may extend through IMD 612A along a substantially flat plane that is substantially perpendicular to both bottom major surface 622 and longitudinal axis 608 of channel 632. Interface 636 may extend across IMD 612A such that interface 636 contacts sidewall 624 at two locations as it extends across IMD 612A.

In other examples, interface 636 may define two or more planes that are curved and/or angle as interface 636 extends across IMD 612A (not depicted). For example, interface 636 may include both a first segment and a second segment. The first segment of interface 636 may define a plane that is substantially perpendicular to longitudinal axis 608 of channel 632 as the first portion of interface 636 crosses channel 632. The second segment of interface 636 may define a plane that is not perpendicular to longitudinal axis 608 of channel 632. For example, the second segment of interface may define a plane that is angled approximately 45° or 30° relative to longitudinal axis 608 of channel 632. In some examples, where interface 636 defines one or more planes are not substantially perpendicular to longitudinal axis 608 of channel 632, all planes defined by interface 636 may be substantially perpendicular to bottom major surface 622. Where interface 636 angles as interface 636 extends across 612A, interface 636 may therein decrease or increase a relative volume of funneling section 618 and housing 616, therein enabling one of funneling section 618 or housing 616 to contain more internal components as desired.

FIG. 43 depicts a cross-sectional view of IMD 612A along cut plane 628 of FIG. 42. FIG. 43 depicts cut-plane 645 of FIG. 48. FIG. 43 depicts a plurality of connectors 638 that are configured to electrically couple lead 14 to internal components once lead 14 is received by channel 632. In some examples, a features that defines channel 632 may include one or more features that extend radially in to channel 632 at a distal end 642 of channel 632. For example, distal end 642 of channel 632 may define a rounded or angled end that is configured to contact a distal end of lead 14 once lead 14 is fully received by channel 632 (e.g., successfully received by channel 632 such that lead 14 is electrically coupled to internal components of IMD 612A as described herein). As a result of distal end 642 of channel 632 including features that extend radially in to channel 632, IMD 612A may provide tactile feedback to a clinician in response to the clinician inserting lead 14 a predetermined (e.g., correct) depth into channel 632. By providing tactile feedback to a clinician inserting lead 14, IMD 612A may reduce a likelihood of error that may result from lead 14 being improperly inserted to distal end 642 of channel 632 (e.g., not inserted deep enough to provide full electrical coupling, or pushing too hard in an attempt to secure proper coupling and therein damaging one of lead 14 or IMD 612A).

As depicted in FIG. 43, stack 644 may define channel 632. Stack 644 may be a discrete component that is received by groove 610 and then securely attached to housing 616 as described herein. Stack 644 may electrically couple to lead 14 once channel 632 of stack 644 receives lead 14. Similarly, once stack 644 is received by groove 610, connectors 638 may be electrically coupled (e.g., laser welded) to stack 644 and welded at openings 604 (to seal cavity 640) as described above. Stack 644 may include one or more conductive element 672 for each electrode of lead 14 and one or more electrically isolating element 674 between each adjacent pair of conductive elements 672. As assembled into IMD 612A, stack 644 may substantially share or otherwise be aligned with longitudinal axis 608 of channel 632. In some examples, each conductive element 672 and insulating element 674 of stack 644 may extend radially through stack 644 from channel 632 to an outer surface of stack 644 across a full circumference of stack 644, such that stack 644 may electrically couple lead 14 to connectors 638 regardless of a radial orientation of stack 644 upon full assembly of IMD 612A. In other examples, conductive elements 672 of stack 644 may only extend through a radial portion and/or a circumferential portion of stack 644 (e.g., a portion that is configured to be located near top major surface 620 where stack 644 contacts connectors 638 when IMD 612A is fully assembled), such that stack 644 may only properly electrically couple lead 14 to connectors 638 when stack 644 is properly radially oriented (e.g., rotated) relative to IMD 612A.

Stack 644 may define a plurality of troughs 648 that extend radially in towards longitudinal axis 608 of channel 632 as defined by stack 644. Stack 644 may define troughs 648 between each adjacent pair of conductive elements 672 of stack 644. In some examples (e.g., where stack 644 defines conductive elements 672 that extend along a full circumference of stack 644), troughs 648 may extend along a full circumference of stack 644 along a plane that is substantially perpendicular to longitudinal axis 608. Once stack 644 is assembled into IMD 612A (e.g., received and welded into groove 610), each trough 648 may be filled with an adhesive and electrically isolating material. For example, each trough 648 may be filled with a silicon adhesive. A needle may be inserted into trough 648 to enable the electrically insulating adhesive material to flow throughout trough 648. As a result of stack 644 defining troughs 648 between adjacent pairs of conductive elements within stack 644, IMD 612A may improve an ability to electrical isolate signals of lead 14 when securing stack 644 into groove 610 of housing 616, therein improving an ability of IMD 612A to provide therapy as described herein.

Configuring IMD 612A such that stack 644 that is received by groove 610 may define at least a portion of channel 632 such that lead 14 received by channel 632 may be electrically coupled to internal components using connectors 638 may improve a robustness of IMD 612A. For example, IMD 612A that utilizes stack 644 that can be adhered to groove 610 and then welded to electrically coupled a received lead 14 to connectors 638 may include/require less welds (and therein may include less potential sources of failure) than an IMD that utilizes a separate sub assembly that includes connectors that is installed within a housing of an IMD.

Further, it is to be understood that stacks 644 may be utilized in IMDs 112A, 112B, 212A, 212B, 312A, 312B, 412A, 412B, 512A, 512B as described above. Stacks 644 may be configured to define at least a portion of channels 132, 190, 232, 290, 332, 390, 432, 490, 532, 590 as described above. For example, stack 644 may be received in a groove similar to groove 610 defined by major surface 120 of connector header 136 or a major surface of connector headers 192. Connectors may be configured to extend from a groove defined by connector header 136 or connector heads 192 to electrically couple a respective stack 644 (and therein a respective lead 14 received by respective stack 644) to internal components 118. In this way, stack 644 may replace connector stack 184 of IMD 112A. Similarly, stack 644 may be received in a groove similar to groove 610 defined by top major surface 221 of connector header 236 and/or connector headers 292 to replace connector stack(s) 284 of IMD 212A, 212B.

Further, stack 644 may be received in a groove similar to groove 610 defined by top surface 320 of housing 316 of IMD 312A. Stack 644 may be configured to electrically couple lead(s) received by channels 332, 390 of IMDs 312A, 312B to connector pins that are themselves coupled to internal components within a cavity defined by BIDS 312A, 312B. Similarly, top surface of housings 416, 498 of IMDs 412A, 412B may define grooves similar to groove 610 that may receive one or more stacks 644 with which received leads 14 may be electrically coupled to internal components. Further, top surfaces of housings 516, 598 of BIDS 512A, 512B may define grooves similar to groove 610 that are configured to receive one or more stacks 644 to electrically couple received leads 14 to internal components.

Figure 44:
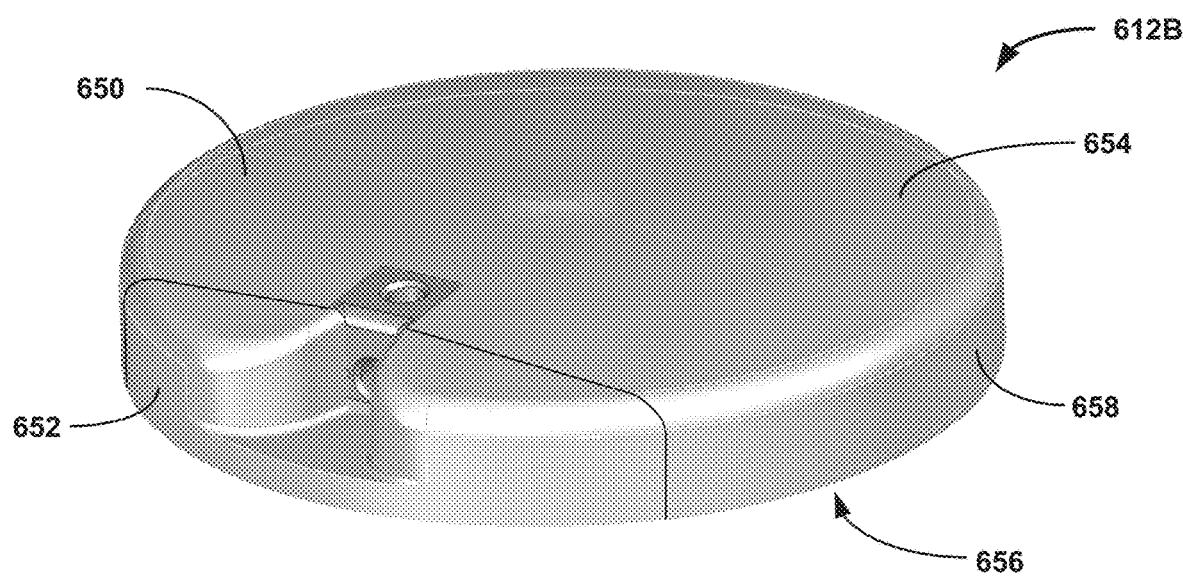
FIG. 44 is a conceptual and schematic diagram illustrating an isometric view of an example IMD with channel for receiving a lead that includes a connector sub-assembly.

FIG. 44 is a conceptual and schematic isometric view of example IMD 612B. IMD 612B may be substantially similar to IMD 612A with the exception of any differences described herein. For example, IMD 612B may not define groove 610 in a top major surface. Further, IMD 612B may include a different version of a stack (e.g., stack 668 of FIG. 46). IMD 612B may include housing 650 and funneling section 652. Funneling section 652 may be a "porch" of IMD 612B that is substantially similar to funneling section 618, and housing 650 may be substantially similar to housing 616 outside of housing 650 defining a flat top surface without groove 610. Put differently, housing 650 and funneling section 652 may define top surface 654, bottom surface 656, and sidewall 658 that are substantially similar to top major surface 620, bottom major surface 622, and sidewall 624, other than top surface 654 defining a substantially continuous and "smooth" surface as it domes away from bottom major surface 622 between sidewall 624.

Figure 45:
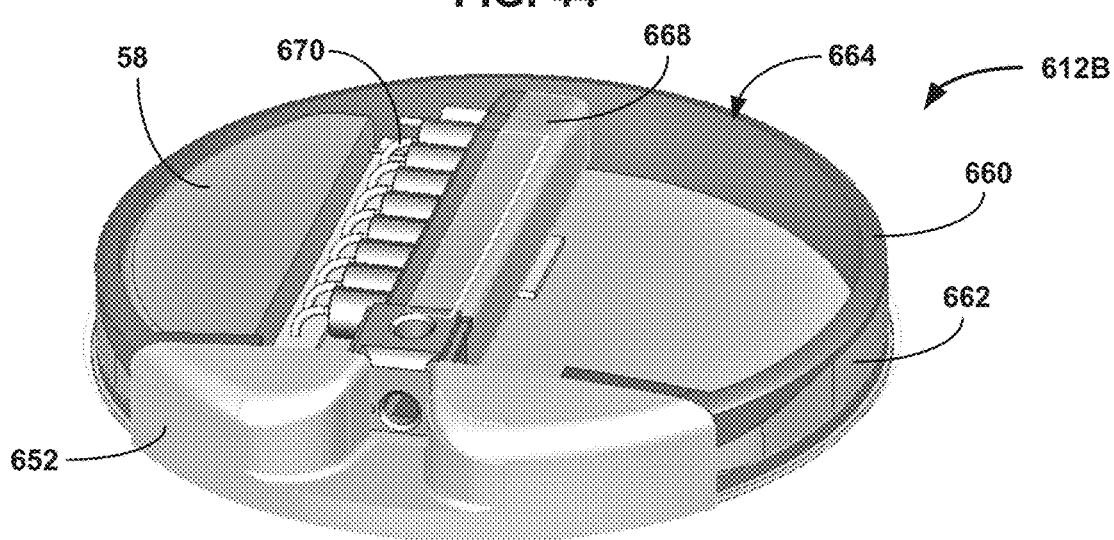
FIG. 45 is a conceptual and schematic diagram illustrating an isometric view of the IMD of FIG. 44 with a portion of the housing of the IMD removed.
Figure 46:
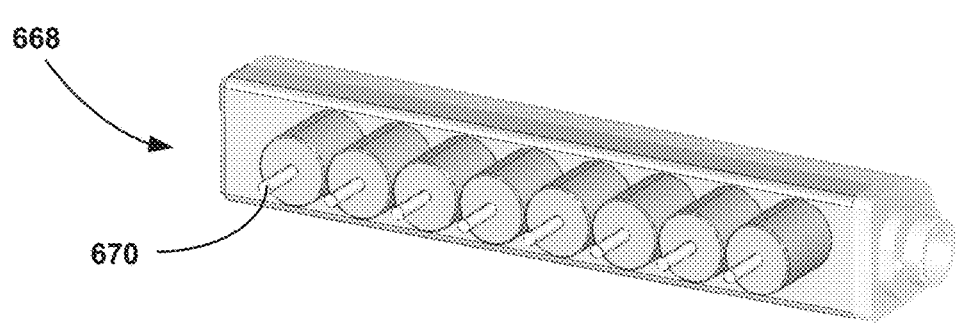
FIG. 46 is a conceptual and schematic diagram illustrating an isometric view of the connector sub-assembly of the IMD of FIG. 44.

FIG. 45 is a conceptual and schematic isometric view of IMD 612B without a portion of housing 650 (e.g., without a metal can enclosure and without an overmold), and FIG. 46 is a conceptual and schematic isometric view of stack 668 as received by IMD 612B. Stack 668 may be partially encased in a material to promote the isolation of the components of stack 668 and IMD 612B. For example, stack 668 may include a titanium enclosure encased with rubber between respective internal conductive elements to promote electrical isolation.

In some examples, within the portion of housing 650 that defines sidewall 658, housing 650 may include supporting wall 660 (which may be a molded polymer cup) and coil 662 that wraps around supporting wall 660. In some examples, coil 662 may be copper wire, and may be recharge coil 66 or a telemetry coil for telemetry circuitry 56. As depicted in FIG. 45, cavity 664 as defined by housing 650 is visible. Cavity 664 may be substantially similar to cavity 640. As depicted, a D-shaped battery that functions as power source 58 may fit within cavity 664. Further, cavity 664 of IMD 612B includes stack 668 which may be substantially similar to stack 638, except stack 668 includes a plurality of connectors 670 that are substantially similar to connectors 638. As such, once stack 668 is received by cavity 664 of IMD 612B, it may be unnecessary to weld components of IMD 612B to electrically couple lead 14 to internal components of IMD 612B and/or hermetically seal cavity 664 of IMD 612B. In this way, by configuring stack 668 to include connectors 670, an assembly of IMD 612B may remove the "wet" processes (e.g., processes including welding) off of the main line where final components of IMD 612A are secured together.

Further, as a result of configuring stack 668 and connector 670 to be a separate sub-assembly that are manufactured together, IMD 612B may be relatively smaller than IMD 612A. For example, as a result of coupling connectors 670 and stack 668 in a separate step before receiving either by IMD 612B, an amount of space that is needed to enable proper electrical isolation may be reduced by, e.g., 0.75 millimeters or more in certain areas. Further, configuring stack 668 and connectors 670 to be connected in a separate sub-assembly may increase a modularity of components of IMD 612B. As a result of increasing a modularity of components of IMD 612B, it may be relatively easier to interchange components of IMDs over time, and/or provide maintenance to IMDs over time (e.g., swapping out a first stack with a second stack for a respective IMD).

FIG. 47 is a conceptual and schematic isometric view of example IMD 612C. IMD 612C may be substantially similar to IMD 612A and 612B with the exception of any differences described herein. FIG. 47 depicts cut plane 695 of FIG. 49. IMD 612C may be substantially mirrored across central plane 692 of IMD 612C. IMD 612C defines two channels 690A, 690B (collectively, "channels 690"). Channels 690 may extend on either side of central plane 692 radially into housing 694, which may be substantially similar to housing 616. Each channel 690 may begin at a mouth defined by funneling section 696, which may be a "porch" of IMD 612C that is substantially similar to funneling section 618. As depicted in FIG. 47, both channels 690 have received a respective lead 14. Both channels 690 may be at least partially defined by a respective stack 644 that may both be received by groove 698 of housing 694 (which may be substantially similar to groove 610 described above). In other examples, housing 694 may not define groove 698 and IMD 612C may utilize stacks 668 to define channels 690 and electrically couple leads 14 to internal components.

As a result of having two channels 690, IMD 612C may be configured to simultaneously provide therapy to and/or monitor patient 18 through two separate leads 14. In some examples, as a result of utilizing two leads 14 electrically coupled to IMD 612C through two channels 690, more (or otherwise different) internal components may be necessary. For example, power source 58 may need relatively more power to supply a sufficient amount of power to both leads 14 within both channels 690. Similarly, stimulation circuitry 52 may need to be more robust to provide potentially different electrical signals to both leads 14. However, some internal components of IMD 612C may be substantially similar to respective internal components of IMD 612A or IMD 612B. For example, IMD processing circuitry 50 of IMD 612A or IMD 612B may be substantially similar to processing circuitry 50 for IMD 612C.

In some examples, IMDs 612A, 612C may be configured to define angles that improve the ability to laser weld connectors 638 to one or more stacks 644 and openings 604. For example, FIGS. 48 and 49 depict cross-sectional views of IMDS 612A and 612C as viewed along cut planes 645, 695 of IMDS 612A, 612C, respectively. Stacks 644 are depicted with dotted lines in FIGS. 48 and 49 for purposes of clarity.

Turning to FIG. 48, as discussed above, groove 610 may include two longitudinal walls 676A, 676B (collectively, "longitudinal walls 676") that extend along a longitudinal length of groove 610. Longitudinal walls 676 may converge toward each other as groove 610 extends from top major surface 620 toward bottom major surface 622. Each of longitudinal walls 676 may define substantially flat plane 678 as longitudinal walls 676 extend from top major surface 620 toward bottom major surface 622. Substantially flat plane 678 may define angle 680 between 45° and 65° relative to bottom major surface 622 of housing 616. Dimensioning groove 610 such that longitudinal walls 676 define an angle between 45° and 65° may enable connectors 638 to be welded at openings 604. For example, if longitudinal wall 676A defines plane 678 that is at angle 680 that is less than 45°, then connectors 638 may have insufficient space within cavity 640 to bend to a circuit board, therein providing insufficient length for soldering connectors 638 to the circuit board. For another example, if longitudinal wall 676A defines plane 678 that is at angle 680 that is more than 65°, it may be difficult or impossible to laser weld connectors 638 at opening 604 to seal cavity 640 and stabilize connectors 638.

Turning to FIG. 49, IMD 612C may define groove 698 in much the same way. For example, IMD 612C may define groove 698 with longitudinal walls 682A, 682B (collectively, "longitudinal walls 682") that extend between a top major surface and a bottom major surface while defining relatively flat planes 684A, 684B (collectively, "flat planes 684"). Flat planes 684 may define angles 686 that are between 45' and 75°. Angles 686 as defined by longitudinal walls 682 of groove 698 of MD 612C may be relatively larger than angles 680 of groove 610 of IMD 612A as a result of groove 698 being wider to receive two stacks 644.

Figure 50:
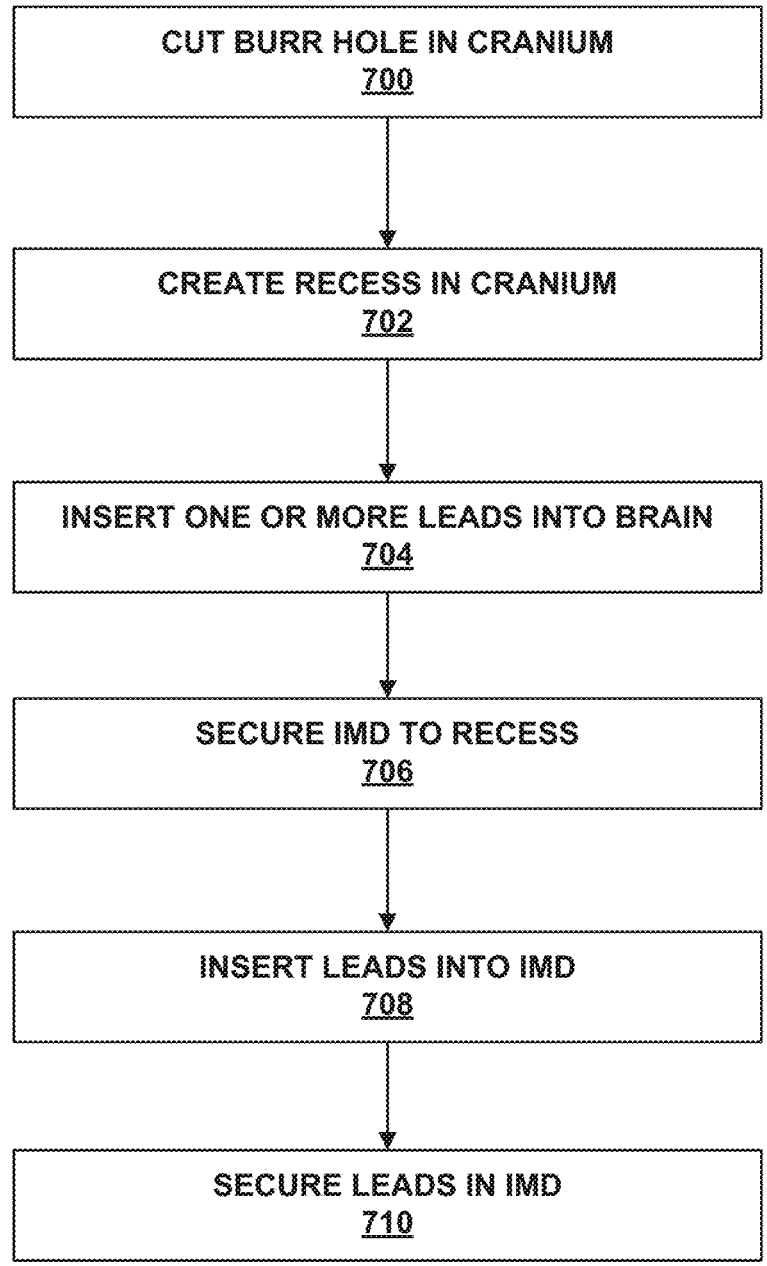
FIG. 50 is a flowchart of a method of implanting an implanted medical system that includes an IMD according to the techniques described herein.

FIG. 50 is a flowchart of an example method of implanting a medical device system that includes an IMD as described herein. FIG. 50 is described with reference to system 10 of FIGS. 1-4 and IMD 612A of FIGS. 40-43, though the flowchart of FIG. 50 may be executed with other IMDs similar to those described herein, and IMD 612A may be used in other methods than the flowchart of FIG. 50. A clinician may cut burr hole 26 in cranium 20 (700). In some examples, a clinician may create two burr holes 26 in cranium 20. In some examples, the clinician may create burr hole 26 for every lead 14 of system 10. In other examples, the clinician may utilize a single burr hole 26 for a plurality of leads 14 where multiple leads 14 are going to a single hemisphere of a brain of patient 18.

A clinician may create recess 606 in cranium 20 (702). Recess 606 may be substantially same size and shape of IMD 612A (e.g., the same shape but 5% bigger to enable IMD 612A to fit into recess 606. The clinician may drill recess 606 into cranium 20. For example, the clinician may use a drill bit that defines a diameter that is substantially the same size as IMD 612A to create a cylindrical recess 606 in cranium 20. The clinician may insert one or more leads 14 into the brain of patient 18 through burr holes 26 (704). The clinician may navigate leads 14 to their respective target sites within the brain of patient 18.

The clinician may place IMD 612A in recess 606 and secure IMD 612A to recess 606 (706). Securing IMD 612A to cranium 20 when IMD 612A is in recess 606 may include suturing IMD 612A to patient 18 using bore 630. In some examples, IMD 612A may be rotated to a desired position within recess 606 prior to securing IMD 612A to craniums 20. Once IMD 612A is secured to cranium 20, lead(s) 14 may be inserted into IMD 612A (708). Lead 14 may be inserted into mouth 646 as defined by funneling section 618 and inserted into channel 632 until lead 14 hits distal end 642 of channel 632. In some examples, features of distal end 642 of channel 632 that extend radially into channel 632 may provide tactile feedback for clinician to inform clinician that lead 14 has been inserted a proper depth. Alternatively, or additionally, in some examples one or more portions of IMD 612A may be relatively transparent to enable the clinician to visually inspect the insertion of lead 14. In some examples, an IMD may be configured to receive more than one lead 14, such as IMD 612C. In such examples, the clinician may insert all leads 14 into respective channels 690 of IMD 612C.

Once lead 14 is inserted into IMD 612A, lead 14 may be secured to IMD 612A (710). For example, a securing bolt may be placed into threaded bore 634 on top major surface 620 of housing 616 to press lightly into lead 14 as inserted in IMD 612A. Securing lead 14 in channel 632 of IMD 612A may improve an ability of system 10 as implanted to retain proper electrical coupling between lead 14 and internal components of IMD 612A.

Figure 51:
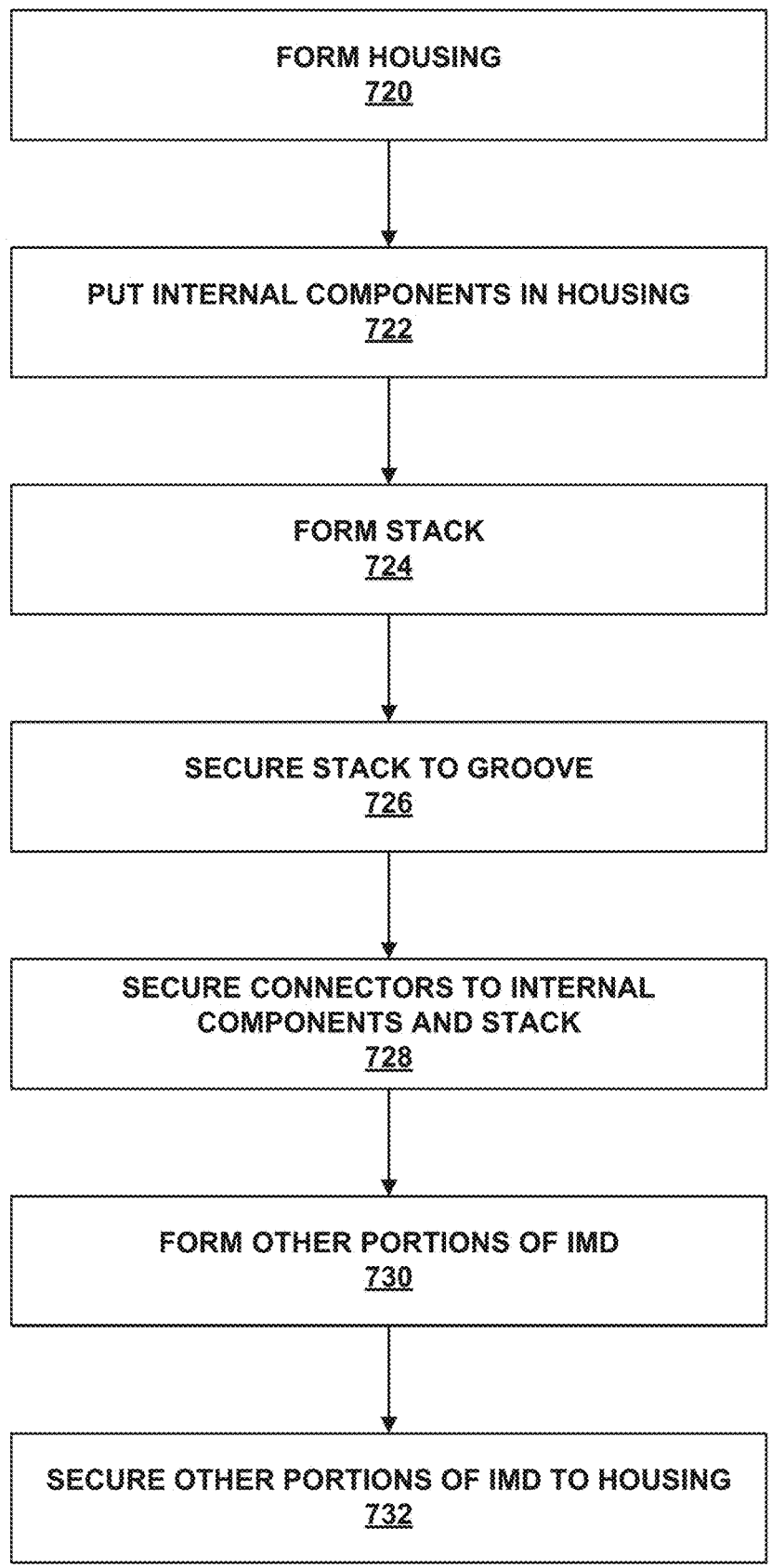
FIG. 51 is a flowchart of a method of forming an IMD according to the techniques described herein.

FIG. 51 is a flowchart of an example method of forming a medical device system that includes an IMD as described herein. FIG. 51 is described with reference to system 10 of FIGS. 1-4 and IMD 612A of FIGS. 40-43, though the flowchart of FIG. 51 may be executed with other IMDs similar to those described herein, and IMD 612A may be used in other methods than the flowchart of FIG. 51. The method of FIG. 51 may start with housing 616 being formed (720). As discussed herein, housing 616 may include a metallic structure such as a metal can made of titanium. In some examples, housing 616 may include a metal can that has one or more layers or coatings on it, such as polymeric layers to define smoother or more contoured perimeter edges. Internal components may be received by housing 616 (722). Internal components may include processing circuitry 50, stimulation circuitry 52, memory 54, telemetry circuitry 56, power source 58, or the like. Internal components may be secured to a circuit board, such as a rigid-flex PCB. In some examples, internal components may include recharge coil 66. In other examples, recharge coil 66 may be wrapped around an outer perimeter of metal can of housing 616.

Stack 644 of IMD 612A may be formed (724). Stack 644 may be formed to define channel 632 with conductive elements 672 radially extending from channel 632 to an outer surface of stack 644. Stack 644 may include electrically insulating elements 674 on either side of conductive elements 672 to promote an integrity of an electrical signal between internal components of IMD 612A and lead 14. Stack 644 may be received by groove 610 of housing 616 (726). Stack 644 may be securely attached within groove 610. For example, an electrically insulating adhesive may be injected into troughs 648 defined by the outer surface of stack 644 such that the electrically insulating adhesive extends around at least a portion of a circumference of stack 644 that is adjacent housing 616 within groove 610. The adhesive may both adhere stack 644 to housing 616 within groove 610 as well as provide further insulation between conductive elements 672 of stack 644.

Connectors 648 may be secured and electrically coupled to internal components and conductive elements 672 of stack 644 (728). Connectors 648 may be laser welded to conductive elements 672 of stack 644. Connectors 648 may further be laser welded at opening 604 to secure connectors 648 at opening 604 and/or the hermetically seal cavity 640 of housing 616. In some examples, connectors 648 may be soldered to a circuit board containing internal components in order to be electrically coupled to internal components. In other examples, connectors 648 be electrically coupled (e.g., laser welded) to other discrete components at openings 604, such that the other components are electrically coupled (e.g., soldered) to the circuit board. For example, connectors 648 may be laser welded at openings 604 to pins that extend in to electrically couple to internal components as described and depicted herein.

Other portions of IMD 612A may be formed (730). For example, funneling section 618 may be formed, or tethers 414, 514 may be formed, or connection headers 136, 236 may be formed, though funneling section 618 is discussed here for purposes of clarity. Funneling section 618 may include a metal can in a manner that is substantially consistent with housing 616. Alternatively, funneling section 618 may be formed with softer and relatively more flexible materials than housing 616. For example, funneling section 618 may be formed of a polymeric material such as polysulfone, polyurethane, epoxy, PEEK, LDPE, or the like. The other portions of IMD 612A may be secured to housing 616A (732). This may include using an overmold over both funneling section 618 and housing 616. Additionally, or alternatively, this may include welding or bonding funneling section 618 to housing 616 at an interface between funneling section 618 and housing 616.

Clause 1: In one example, an implantable medical device includes: a hermetically sealed housing that is configured to enclose internal components including at least: stimulation circuitry, processing circuitry configured to cause the stimulation circuitry to deliver deep brain stimulation using one or more leads; telemetry circuitry; a rechargeable power source; and a recharge coil configured to recharge the rechargeable power source, the housing defining two major surfaces that are generally parallel to each other, the housing defining one or more channels each configured to receive one of the one or more leads and electrically couple the respective lead to the internal components, each of the one or more channels extending substantially straight in to the housing along an axis generally parallel to the two major surfaces, the housing configured to mount to a cranium of a patient such that at least one of the two major surfaces approximates a curvature of the cranium.

Clause 2: In some examples of the implantable medical device of clause 1, the one or more channels includes two channels.

Clause 3: In some examples of the implantable medical device of any of clauses 1 or 2, the housing is substantially mirrored across a central plane of the housing that bisects the two channels.

Clause 4: In some examples of the implantable medical device of any of clauses 1-3, the housing defines a groove that extends from the second major surface toward the first major surface along one or more longitudinal axes of the one or more channels, wherein one or more connectors electrically coupled to the internal components in the housing are electrically coupled to the one or more leads within the groove, further comprising a stack that defines at least a portion of one of the one or more channels and is configured to be received by the groove, wherein the stack includes a plurality of electrical conductors that extend from the respective channel defined by the stack radially out to an outer surface of the stack to electrically couple the one or more connectors to the respective lead received by the respective channel defined at least partially by the stack.

Clause 5: In some examples of the implantable medical device of any of clauses 1-4, some features of the implantable medical device are at least partially transparent to enable visual confirmation of a coupling between the one or more leads and the one or more channels.

Clause 6: The implantable medical device of any of clauses 1-5, the housing includes a main chassis and one or more connector headers that each define one of the one or more channels, the one or more connector headers configured to be securely attached to the main chassis, the one or more connector headers each defining one or more windows that align with one or more windows of the main chassis when the connector headers are securely attached to the main chassis, wherein respective connector stacks within the one or more connector headers are configured to electrically couple the one or more leads received by the one or more channels through the one or more windows to the internal components housed by the main chassis.

Clause 7: In some examples of the implantable medical device of clause 6, the housing includes a battery compartment to house the power source, the battery compartment configured to be securely attached to the main chassis adjacent the one or more connector headers such that the battery compartment defines a weldable interface between itself and each of the one or more connector headers, the battery compartment configured to align with one or more windows of the main chassis through which the power source is electrically coupled to the internal components housed by the main chassis.

Clause 8: In some examples of the implantable medical device of clause 7, the power source includes a D-shaped lithium ion battery.

Clause 9: In some examples of the implantable medical device of any of clauses 6-8: one of the two major surfaces comprises a bottom surface of the chassis and bottom surfaces of each of the one or more connector headers; the bottom surface of the chassis and the bottom surfaces of the each of the one or more connector headers are configured to contact the cranium when the implantable medical device is secured to the cranium of the patient; the other of the two major surface comprises a top surface of the chassis that is opposite the bottom surface of the chassis and top surfaces of the one or more connector headers that are opposite the bottom surfaces of the one or more connector headers; the chassis defines a relatively flat plane; each of the one or more connector headers define a set of relatively flat planes; and the one or more connector headers are configured to be secured to the chassis such that the relatively flat plane is at an angle to each of the set of relatively flat planes, the angle approximating the curvature of the cranium such that both of the two major surfaces approximate the curvature of the cranium.

Clause 10: In some examples of the implantable medical device of any of clauses 1-5, the two major surfaces both define generally parabolic curves arcing in a substantially similar direction along a shared axis that is in a plane that bisects the housing, the two major surfaces including a top surface and a bottom surface configured to approximate the curvature of the cranium of a patient, the bottom surface and the top surface configured to meet along the outer perimeter of the housing.

Clause 11: In some examples of the implantable medical device of clause 11, the top major surface domes away from the bottom major surface to create an internal cavity to store the internal components.

Clause 12: In some examples of the implantable medical device of any of clauses 10 or 11, the one or more channels are closer to the top major surface than to the bottom major surface.

Clause 13: In some examples of the implantable medical device of any of clauses 10-12, the power source is received by the housing on a first side of the one or more channels and substantially all of the processing circuitry and telemetry circuitry and stimulation circuitry received by the housing on a second side of the one or more channels.

Clause 14: In some examples of the implantable medical device of clause 13, the power source is electrically coupled to the internal component on the second side via a connection that extends between the one or more channels and the bottom major surface.

Clause 15: In some examples of the implantable medical device of any of clauses 10-14, the medical devices further includes a rigid-flex printed circuit board on which at least one of the internal components is mounted.

Clause 16: In some examples of the implantable medical device of any of clauses 10-15, the one or more leads received by the one or more channels are electrically coupled to the internal components by connectors that extend between the internal components to the one or more channels along a plane that is tangential to the one or more channels.

Clause 17: In some examples of the implantable medical device of any of clauses 1-5, the two major surfaces define substantially similar generally parabolic curves that approximate the curvature of the cranium of a patient, a sidewall of the housing extending between the two major surfaces, further comprising one or more relatively flexible tethers extending from the housing that each define a channel configured to receive a lead such that the lead is electrically coupled to the internal components.

Clause 18: In some examples of the implantable medical device of clause 17, the implantable medical device further includes a recharge coil within overmolding surrounding an outer perimeter of the housing.

Clause 19: In some examples of the implantable medical device of any of clauses 17 or 18, the implantable medical device further includes a recharge coil coiled around one of the at least one channels at a distal end of one of the relatively flexible tethers.

Clause 20: In some examples of the implantable medical device of any of clauses 17-19, the two major surfaces includes a bottom surface that is configured to contact the cranium when the implantable medical device is secured to the cranium and a top surface, wherein the bottom surface is relatively larger than the top surface and the sidewall is angled between the bottom surface and the top surface.

Clause 21: In some examples of the implantable medical device of any of clauses 17-20, the two major surfaces include a bottom surface that is configured to contact the cranium when the implantable medical device is secured to the cranium, further comprising a protrusion extending from the bottom surface that is configured to be received by a recess in the cranium of the patient.

Clause 22: In some examples of the implantable medical device of clause 21, the protrusion is a substantially cylindrical protrusion, wherein the battery is a substantially cylindrical battery that is received by the protrusion.

Clause 23: In some examples of the implantable medical device of any of clauses 1-5, the implantable medical device further includes a funneling section that is securely attached to the housing and defines a mouth to the one or more channels, wherein the housing and funneling section together define the first and second major surfaces and a sidewall that extends between the first and the second major surface, wherein the first major surface defines a substantially flat circle and the sidewall extends substantially perpendicular from the first major surface to the second major surface, wherein the second major surface domes away from the first major surface as the second major surface extends radially in towards a center of the implantable medical device to approximate the curvature of the cranium of the patient, wherein the funneling section defines the mouth at a location that is radially recessed from the sidewall, wherein the funneling section defines one or more funneling walls that define a rounded and smooth transition from the sidewall to the surface of funneling section that defines the mouth.

Clause 24: In some examples of the implantable medical device of clause 23, the housing defines a groove that extends along one or more longitudinal axes of the one or more channels from the second major surface toward the first major surface, wherein one or more connectors extending from the hermetically sealed cavity are electrically coupled to the one or more leads within the groove.

Clause 25: In one example, an implantable medical device includes: a hermetically sealed housing that is configured to enclose internal components including at least a processor and telemetry circuitry and a rechargeable power source that the implantable medical device is configured to recharge, the housing defining two major surfaces and a sidewall that extends between the two major surface, wherein the two major surface are generally parallel to each other and define generally similar shapes, the housing defining one or more channels each configured to receive a lead and electrically couple the respective lead to the internal components, each of the one or more channels extending substantially straight in to the housing along an axis generally parallel to the two major surfaces, the housing configured to be mounted to a cranium of a patient; a mouth defined by the implantable medical device that provides access to the channel; and one or more funneling walls that define a rounded and smooth transition from the sidewall to a surface that defines the mouth.

Clause 26: In some examples of the implantable medical device of clause 25, the one or more channels includes two channels, the housing is substantially mirrored across a central plane of the housing that bisects the two channels.

Clause 27: In some examples of the implantable medical device of clauses 25 or 26, the housing defines a groove that extends from the second major surface toward the first major surface along one or more longitudinal axes of the one or more channels, wherein one or more connectors electrically coupled to the internal components in the housing are electrically coupled to the one or more leads within the groove, further comprising a stack that defines at least a portion of one of the one or more channels and is configured to be received by the groove, wherein the stack includes a plurality of electrical conductors that extend from the respective channel defined by the stack radially out to an outer surface of the stack to electrically couple the one or more connectors to the respective lead received by the respective channel defined at least partially by the stack.

Clause 28: In some examples of the implantable medical device of any of clauses 25-27, some features of the implantable medical device are at least partially transparent to enable visual confirmation of a coupling between the one or more leads and the one or more channels Clause 29: In some examples of the implantable medical device of any of clauses 25-28, the housing includes a main chassis and one or more connector headers that each define one of the one or more channels, the one or more connector headers configured to be securely attached to the main chassis, the one or more connector headers each defining one or more windows that align with one or more windows of the main chassis, wherein respective connector stacks within the one or more connector headers electrically are configured to electrically couple the one or more leads received by the one or more channels through the one or more windows to the internal components housed by the main chassis.

Clause 30: In some examples of the implantable medical device of clause 29, the housing includes a battery compartment to house the power source, the battery compartment configured to be securely attached to the main chassis adjacent the one or more connector headers such that the battery compartment defines a weldable interface between itself and each of the one or more connector headers, the battery compartment configured to align with one or more windows of the main chassis through which the power source is electrically coupled to the internal components housed by the main chassis, wherein the power source includes a D-shaped lithium ion battery.

Clause 31: In some examples of the implantable medical device of any of clauses 25-28, the two major surfaces both define generally parabolic curves arcing in a substantially similar direction along a shared axis that is in a plane that bisects the housing, the two major surfaces including a top surface and a bottom surface configured to approximate the curvature of the cranium of a patient, the bottom surface and the top surface configured to meet along the outer perimeter of the housing.

Clause 32: In some examples of the implantable medical device of clause 31, the top major surface domes away from the bottom major surface to create an internal cavity to store the internal components.

Clause 33: In some examples of the implantable medical device of any of clauses 31 or 32, the one or more channels are closer to the top major surface than to the bottom major surface.

Clause 34: In some examples of the implantable medical device of any of clauses 31-33, the power source is received by the housing on a first side of the one or more channels and substantially all of the processing circuitry and telemetry circuitry and stimulation circuitry received by the housing on a second side of the one or more channels and the power source is electrically coupled to the internal component on the second side via a connection that extends between the one or more channels and the bottom major surface.

Clause 35: In some examples of the implantable medical device of any of clauses 31-34, the implantable medical device further including a rigid-flex printed circuit board on which at least one of the internal components is mounted.

Clause 36: In some examples of the implantable medical device of any of clauses 31-35, the one or more leads received by the one or more channels are electrically coupled to the internal components by connectors that extend between the internal components to the one or more channels along a plane that is tangential to the one or more channels.

Clause 37: In some examples of the implantable medical device of any of clauses 25-28, the implantable medical device further including a funneling section that is securely attached to the housing and defines a mouth to the one or more channels, wherein the housing and funneling section together define the first and second major surfaces and a sidewall that extends between the first and the second major surface, wherein the first major surface defines a substantially flat circle and the sidewall extends substantially perpendicular from the first major surface to the second major surface, wherein the second major surface domes away from the first major surface as the second major surface extends radially in towards a center of the implantable medical device to approximate the curvature of the cranium of the patient, wherein the funneling section defines the mouth at a location that is radially recessed from the sidewall, wherein the funneling section defines one or more funneling walls that define a rounded and smooth transition from the sidewall to the surface of funneling section that defines the mouth.

Clause 38: In some examples of the implantable medical device of clause 37, the housing defines a groove that extends along one or more longitudinal axes of the one or more channels from the second major surface toward the first major surface, wherein one or more connectors extending from the hermetically sealed cavity are electrically coupled to the one or more leads within the groove.

Clause 39: In one example, an implantable medical device includes: a housing that is configured to enclose internal components including at least a processor and a power source inside a hermetically sealed cavity, wherein one or more channels that extend through the housing are each configured to receive a lead and electrically couple the lead to the internal components; and a funneling section that is configured to be securely attached to the housing and defines a mouth to the one or more channels, wherein the housing and funneling section together define a first and a second major surface and a sidewall that extends between the first and the second major surface, wherein the first major surface defines a substantially flat circle and the sidewall extends substantially perpendicular from the first major surface to the second major surface, wherein the second major surface domes away from the first major surface as the second major surface extends radially in towards a center of the implantable medical device, wherein the funneling section defines the mouth at a location that is radially recessed from the sidewall, wherein the funneling section defines one or more funneling walls that define a rounded and smooth transition from the sidewall to the surface of funneling section that defines the mouth.

Clause 40: In some examples of the implantable medical device of clause 39, the housing defines a groove that extends from the second major surface toward the first major surface along one or more longitudinal axes of the one or more channels, wherein one or more connectors electrically coupled to the internal components in the housing are electrically coupled to the one or more leads within the groove.

Clause 41: In some examples of the implantable medical device of clause 40, a first longitudinal wall of the groove through which the one or more connectors are electrically coupled to the internal components converges toward a second longitudinal wall of the groove as the first and second longitudinal wall extends from the second major surface toward the first major surface.

Clause 42: In some examples of the implantable medical device of clause 41, an angle between a plane defined by the first longitudinal wall and the first major surface is between 50° and 65°.

Clause 43: In some examples of the implantable medical device of clause 41, the second longitudinal wall through which the one or more connectors are electrically coupled to the internal components converges toward the first longitudinal wall as the second longitudinal wall extends from the second major surface toward the first major surface, wherein a first angle between a first plane defined by the first longitudinal wall and the first major surface is between 50° and 75° and a second angle between a second plan defined by the second longitudinal wall and the second major surface is between 50° and 75°.

Clause 44: In some examples of the implantable medical device of any of clauses 41-43, the implantable medical device further including a stack that defines at least a portion of one of the one or more channels and is configured to be received by the groove, wherein the stack includes a plurality of electrical conductors that extend from the channel radially out to an outer surface of the stack to electrically couple the one or more connectors to the respective lead received by the channel defined by the stack.

Clause 45: In some examples of the implantable medical device of any of clauses 39-44, the one or more channels bisect the housing such that a first side of the housing is at least 20% greater than a second side of the housing, wherein the power source is contained within the second side of the housing.

Clause 46: In one example, a method of implanting the implantable medical device of any of clauses 1-45 includes:

cutting one or more burr holes in a cranium of a patient; creating a recess in the cranium, inserting one or more leads into the burr hole and navigating the leads to one or more respective target sites in a brain of the patient; securing a bottom major surface of the implantable medical device to the recess; inserting the one or more leads into one or more channels of the implantable medical device; and securing the one or more leads within the one or more channels.

Clause 47: In some examples of the method of clause 46, one or more leads may be curled around the one or more funneling walls of the implantable medical device as the one or more leads extend out of the one or more channels in response to securing the one or more leads within the one or more channels.

Clause 48: In some examples of the method of any of clauses 46 or 47, securing the one or more leads within the one or more channels includes inserting one or more securing bolts into a respective threaded hole of each of the one or more channels.

Clause 49: In some examples of the method of any of clauses 46-48, creating the recess includes drilling a drill bit once into the cranium of the patient.

Clause 50: In one example, a method of forming the implantable medical device of any of clauses 1-45 includes: forming a housing configured to enclose internal components including at least a processor and a power source inside a cavity of the housing; securing the internal components within the cavity; forming one or more stacks configured to define at least a portion of a channel of the implantable medical device, wherein each of the one or more stacks includes one or more electrically conductive elements that extend from the portion of the channel defined by the respective stack to an outer surface of the stack; securing the stack within a groove of the housing that defines one or more openings to the cavity; electrically couple each of the one or more connectors to the internal components within the cavity; secure each of the one or more connectors at the one or more openings to hermetically seal the cavity; electrically couple the one or more connectors to the one or more conductive elements of the stack; form one or more other portions of the implantable medical device; and secure the one or more other portions of the implantable medical device to the housing.

Clause 51: In some examples of the method of clause 50, where the one or more other portion of the implantable medical device include a funneling section of the implantable medical device that defines a mouth to the one or more channels.

Clause 52: In some examples of the method of clause 50, where the one or more other portion of the implantable medical device include a tether of the implantable medical device that defines portion of the one or more channels.

Clause 53: In some examples of the method of clause 50, where the one or more other portion of the implantable medical device include a connector header of the implantable medical device that defines a connector header that defines a portion of the housing.

Clause 54: In some examples of the method of any of clauses 50-53, securing the one or more portions of the implantable medical device to the housing includes forming an overmold over both the housing and the one or more portions of the implantable medical device.

Clause 55: In some examples of the method of any of clauses 50-53, securing the one or more portions of the implantable medical device to the housing includes welding the housing to the one or more portions of the implantable medical device.

Clause 56: In some examples of the method of any of clauses 50-53, securing the one or more portions of the implantable medical device to the housing includes adhesively bonding the housing to the one or more portions of the implantable medical device.

The invention claimed is:

1. An implantable medical device comprising:
a hermetically sealed, substantially rigid housing that is configured to enclose internal components, the internal components including:
stimulation circuitry;
processing circuitry configured to cause the stimulation circuitry to deliver electrical stimulation using one or more leads received by the housing;
telemetry circuitry;
a rechargeable power source; and
a recharge coil configured to recharge the rechargeable power source,
the housing defining two major surfaces that are generally parallel to each other, the housing defining one or more channels, wherein each channel of the one or more channels is configured to receive one of the one or more leads to electrically couple the respective lead to the internal components, wherein each channel of the one or more channels extends substantially straight in to the housing along an axis generally parallel to the two major surfaces, and wherein the housing is configured to mount to a cranium of a patient such that at least one of the two major surfaces approximates a curvature of the cranium.

2. The implantable medical device of claim 1, wherein the one or more channels includes two channels, wherein the housing is substantially mirrored across a central plane of the housing that bisects the two channels.

3. The implantable medical device of claim 1, wherein an outer surface of the housing of the implantable medical device is at least partially transparent to enable visual confirmation of the one or more leads being inserted to a predetermined depth within the one or more channels from outside the housing.

4. The implantable medical device of claim 1, wherein the housing defines a groove that extends from the second major surface toward the first major surface along one or more longitudinal axes of the one or more channels, wherein one or more connectors electrically coupled to the internal components in the housing are configured to electrically couple the one or more leads within the groove, further comprising a stack that defines at least a portion of one of the one or more channels and is configured to be received by the groove, wherein the stack includes a plurality of electrical conductors each separate from a longitudinally adjacent electrical conductor by an electrical insulator, each of the plurality of electrical conductors extend from the respective channel defined by the stack radially out to an outer surface of the stack to electrically couple the one or more connectors to the respective lead received by the respective channel defined at least partially by the stack.

5. The implantable medical device of claim 1, wherein the housing includes a main chassis and one or more connector headers that each define one of the one or more channels, the one or more connector headers configured to be securely attached to the main chassis, the one or more connector headers each defining one or more windows that align with one or more windows of the main chassis when the connector headers are securely attached to the main chassis, and wherein respective connector stacks within the one or more connector headers are configured to electrically couple the one or more leads received by the one or more channels through the one or more windows to the internal components housed by the main chassis, wherein the housing includes a battery compartment to house the rechargeable power source, wherein the battery compartment is configured to be securely attached to the main chassis adjacent the one or more connector headers such that the battery compartment defines a weldable interface between itself and each of the one or more connector headers, and wherein the battery compartment is configured to align with one or more windows of the main chassis through which the rechargeable power source is electrically coupled to the internal components housed by the main chassis.

6. The implantable medical device of claim 5, wherein:
one of the two major surfaces of the housing comprises a bottom surface of the chassis and bottom surfaces of each of the one or more connector headers;
the bottom surface of the chassis and the bottom surfaces of the each of the one or more connector headers are configured to contact the cranium when the implantable medical device is secured to the cranium of the patient;
the other of the two major surface comprises a top surface of the chassis that is opposite the bottom surface of the chassis and top surfaces of the one or more connector headers that are opposite the bottom surfaces of the one or more connector headers;
the chassis defines a relatively flat plane;
each of the one or more connector headers define a set of relatively flat planes; and
the one or more connector headers are configured to be secured to the chassis such that the relatively flat plane is at an angle to each of the set of relatively flat planes, the angle approximating the curvature of the cranium such that both of the two major surfaces approximate the curvature of the cranium.

7. The implantable medical device of claim 1, wherein the two major surfaces both define generally parabolic curves arcing in a substantially similar direction along a shared axis that is in a plane that bisects the housing, the two major surfaces including a top surface and a bottom surface configured to approximate the curvature of the cranium of a patient, the bottom surface and the top surface configured to meet along the outer perimeter of the housing.

8. The implantable medical device of claim 7, wherein:
the top surface domes away from the bottom surface to create an internal cavity to store the internal components;
the one or more channels are closer to the top surface than to the bottom surface; and
the one or more leads received by the one or more channels are electrically coupled to the internal components by connectors that extend between the internal components to the one or more channels along a plane that is tangential to the one or more channels.

9. The implantable medical device of claim 1, wherein the two major surfaces define substantially similar generally parabolic curves that approximate the curvature of the cranium of a patient, and wherein a sidewall of the housing extends between the two major surfaces, further comprising one or more relatively flexible tethers extending from the housing that each define one of the one or more channels, wherein the two major surfaces includes a bottom surface that is configured to contact the cranium when the implantable medical device is secured to the cranium and a top surface, wherein the bottom surface is larger than the top surface, and wherein the sidewall is angled between the bottom surface and the top surface, wherein the recharge coil is coiled around one of the one or more channels at a distal end of one of the relatively flexible tethers.

10. The implantable medical device of claim 1, wherein the two major surfaces define substantially similar generally parabolic curves that approximate the curvature of the cranium of a patient, and wherein a sidewall of the housing extends between the two major surfaces, further comprising one or more relatively flexible tethers extending from the housing that each define one of the one or more channels, wherein the two major surfaces include a bottom surface that is configured to contact the cranium when the implantable medical device is secured to the cranium, further comprising a protrusion extending from the bottom surface that is configured to be received by a recess in the cranium of the patient, wherein the recharge coil is coiled around one of the one or more channels at a distal end of one of the relatively flexible tethers.

11. The implantable medical device of claim 10, wherein the protrusion is a substantially cylindrical protrusion, wherein the rechargeable power source is a substantially cylindrical battery that is received by the protrusion.

12. The implantable medical device of claim 1, further comprising a funneling section that is securely attached to the housing and defines a respective mouth to each of the one or more channels, wherein the housing and funneling section together define the first and second major surfaces and a sidewall that extends between the first and the second major surface, wherein the first major surface defines a substantially flat circle and the sidewall extends substantially perpendicular from the first major surface to the second major surface, wherein the second major surface domes away from the first major surface as the second major surface extends radially in towards a center of the implantable medical device to approximate the curvature of the cranium of the patient, wherein the funneling section defines the mouth at a location that is radially recessed from the sidewall, wherein the funneling section defines one or more funneling walls that define a rounded and smooth transition from the sidewall to the surface of funneling section that defines the mouth.

13. The implantable medical device of claim 12, wherein the housing defines a groove that extends along one or more longitudinal axes of the one or more channels from the second major surface toward the first major surface, wherein one or more connectors extending from the hermetically sealed cavity are electrically coupled to the one or more leads within the groove.

14. The implantable medical device of claim 1, wherein the hermetically sealed, substantially rigid housing is formed of at least one of titanium or stainless steel.

15. An implantable medical device comprising:
a hermetically sealed housing that is configured to enclose internal components including:
stimulation circuitry;
processing circuitry configured to cause the stimulation circuitry to deliver electrical stimulation using one or more leads received by the housing;
telemetry circuitry;
a rechargeable power source; and
a recharge coil configured to recharge the rechargeable power source,
wherein the housing defines two major surfaces and a sidewall that extends between the two major surfaces, wherein the two major surfaces are generally parallel to each other and define generally similar shapes, wherein the housing defines one or more channels each configured to receive a lead and electrically couple the respective lead to the internal components, each of the one or more channels extending substantially straight in to the housing along an axis generally parallel to the two major surfaces, the housing configured to be mounted to a cranium of a patient;

one or more mouths defined by the implantable medical device that provides access to the one or more channels; and one or more funneling walls that define a rounded and smooth transition from the sidewall to a surface that defines the one or more mouths.

16. The implantable medical device of claim 15, wherein the housing includes a main chassis and one or more connector headers that each defines one of the one or more channels, the one or more connector headers configured to be securely attached to the main chassis, the one or more connector headers each defining one or more windows that align with one or more windows of the main chassis, wherein respective connector stacks within the one or more connector headers electrically are configured to electrically couple the one or more leads received by the one or more channels through the one or more windows to the internal components housed by the main chassis.

17. The implantable medical device of claim 16, wherein the housing includes a battery compartment to house the rechargeable power source, the battery compartment configured to be securely attached to the main chassis adjacent the one or more connector headers such that the battery compartment defines a weldable interface between itself and each of the one or more connector headers, the battery compartment configured to align with one or more windows of the main chassis through which the rechargeable power source is electrically coupled to the internal components housed by the main chassis, wherein the rechargeable power source includes a D-shaped lithium ion battery.

18. The implantable medical device of claim 15, wherein the two major surfaces both define generally parabolic curves arcing in a substantially similar direction along a shared axis that is in a plane that bisects the housing, the two major surfaces including a top surface and a bottom surface configured to approximate the curvature of the cranium of a patient, the bottom surface and the top surface configured to meet along the outer perimeter of the housing.

19. The implantable medical device of claim 18, wherein:
the top surface is dome away from the bottom surface to create an internal cavity to store the internal components;
the one or more channels are closer to the top surface than to the bottom surface; and
connectors that extend between the internal components and the one or more channels along a plane that is tangential to the one or more channels and are configured to electrically coupled the one or more leads received by the one or more channels to the internal components.

20. The implantable medical device of claim 15, further comprising a funneling section that is securely attached to the housing and defines each of the one or more mouths to each of one or more channels, wherein the housing and funneling section together define the first and second major surfaces and a sidewall that extends between the first and the second major surface, wherein the first major surface defines a substantially flat circle and the sidewall extends substantially perpendicular from the first major surface to the second major surface, wherein the second major surface domes away from the first major surface as the second major surface extends radially in towards a center of the implantable medical device to approximate the curvature of the cranium of the patient, wherein the funneling section defines each of the one or more mouths at a location that is radially recessed from the sidewall, wherein the funneling section defines one or more funneling walls that define a rounded and smooth transition from the sidewall to the surface of the funneling section that defines each of the one or more mouths.

21. The implantable medical device of claim 20, wherein the housing defines a groove that extends along one or more longitudinal axes of the one or more channels from the second major surface toward the first major surface, wherein one or more connectors extending from the hermetically sealed cavity are electrically coupled to the one or more leads within the groove.

22. An implantable medical device comprising:
a housing that is configured to enclose internal components including at least processing circuitry and a power source inside a hermetically sealed cavity, wherein one or more channels that extend through the housing are each configured to receive a lead and electrically couple the lead to the internal components; and
a funneling section that is configured to be securely attached to the housing and defines one or more mouths to the one or more channels, wherein the housing and funneling section together define a first and a second major surface and a sidewall that extends between the first and the second major surface, wherein the first major surface defines a substantially flat circle and the sidewall extends substantially perpendicular from the first major surface to the second major surface, wherein the second major surface domes away from the first major surface as the second major surface extends radially in towards a center of the implantable medical device, wherein the funneling section defines each of the one or more mouths at locations that are radially recessed from the sidewall, wherein the funneling section defines one or more funneling walls that define a rounded and smooth transition from the sidewall to the surface of funneling section that defines each of the one or more mouths.

23. The implantable medical device of claim 22, wherein the housing defines a groove that extends from the second major surface toward the first major surface along one or more longitudinal axes of the one or more channels, wherein one or more connectors electrically coupled to the internal components in the housing are configured to electrically couple the one or more leads received by the one or more channels to the internal components.

24. The implantable medical device of claim 23, wherein a first longitudinal wall of the groove through which the one or more connectors are electrically coupled to the internal components converges toward a second longitudinal wall of the groove as the first and second longitudinal wall extends from the second major surface toward the first major surface.

25. The implantable medical device of claim 24, wherein an angle between a plane defined by the first longitudinal wall and the first major surface is between 50° and 65°.

26. The implantable medical device of claim 24, wherein the second longitudinal wall through which the one or more connectors are electrically coupled to the internal components converges toward the first longitudinal wall as the second longitudinal wall extends from the second major surface toward the first major surface, wherein a first angle between a first plane defined by the first longitudinal wall and the first major surface is between 50° and 75° and a second angle between a second plan defined by the second longitudinal wall and the second major surface is between 50° and 75°.

27. The implantable medical device of claim 24, further comprising a stack that defines at least a portion of one of the one or more channels and is configured to be received by the groove, wherein the stack is configured to electrically couple the respective lead received by the channel defined by the stack to the one or more connectors using a plurality of electrical conductors that extend from the respective channel radially out to an outer surface of the stack.

28. The implantable medical device of claim 22, wherein the one or more channels bisect the housing such that a first side of the housing is at least 20% greater than a second side of the housing, wherein the power source is contained within the second side of the housing.

* * * * *